United States Patent
Fitzgerald et al.

(10) Patent No.: US 6,900,194 B1
(45) Date of Patent: May 31, 2005

(54) USE OF SUBSTITUTED 4-BIARYLBUTYRIC AND 5-BIARYLPENTANOIC ACID DERIVATIVES AS MATRIX METALLOPROTEASE INHIBITORS FOR THE TREATMENT OF RESPIRATORY DISEASES

(75) Inventors: Mary F. Fitzgerald, Oxon (GB); Philip J. Gardiner, High Wycombe (GB); Kevin Nash, Burnham Slough (GB); Graham Sturton, Maidenhead (GB); Günter Benz, Velbert (DE); Rolf Henning, Wuppertal (DE); Karl-Heinz Schlemmer, Wuppertal (DE); Bernd Riedl, Wuppertal (DE); Helmut Haning, Wuppertal (DE); Lorenz Mayr, Weil am Rhein (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/869,668

(22) PCT Filed: Dec. 20, 1999

(86) PCT No.: PCT/EP99/10110

§ 371 (c)(1),
(2), (4) Date: Jan. 2, 2002

(87) PCT Pub. No.: WO00/40539

PCT Pub. Date: Jul. 13, 2000

(30) Foreign Application Priority Data

Dec. 30, 1998 (GB) ............................................. 9828845
Sep. 24, 1999 (GB) ............................................. 9922709

(51) Int. Cl.[7] ...................... A61K 31/33; A61K 31/695; C07D 209/02; C07D 209/04
(52) U.S. Cl. ...................... 514/183; 514/408; 514/416; 514/417; 514/243; 514/63; 548/452; 548/470; 548/472
(58) Field of Search ........................... 514/183, 63, 243, 514/417, 408, 416; 548/452, 470, 472

(56) References Cited

U.S. PATENT DOCUMENTS 5,789,434 A  *  8/1998  Kluender et al. ........... 514/414

| 5,854,277 | A | 12/1998 | Kluender |
| 5,859,047 | A | 1/1999 | Kluender |
| 5,861,427 | A | 1/1999 | Kluender |
| 5,861,428 | A | 1/1999 | Kluender |
| 5,874,473 | A | 2/1999 | Kluender |
| 5,886,022 | A | 3/1999 | Kluender |
| 5,886,024 | A | 3/1999 | Kluender |
| 5,886,043 | A | 3/1999 | Kluender |
| 6,166,082 | A | 12/2000 | Kluender |

FOREIGN PATENT DOCUMENTS

| WO | 9615096 | | 5/1996 | ........... C07C/59/88 |
| WO | 9615096 | * | 6/1996 | |
| WO | 9615099 | * | 6/1996 | |
| WO | 9743247 | | 11/1997 | ......... C07C/235/84 |
| WO | 9809940 | | 3/1998 | ......... C07C/251/48 |
| WO | 9822436 | | 5/1998 | ......... C07C/323/56 |
| WO | 9918079 | | 4/1999 | ......... C07D/231/12 |

OTHER PUBLICATIONS

Ricou et al, "MMp and TIMP in ARDS", Am. J. Respr. Crit. Care Med., 154,346–352(1996).*

Kim et al, "Miliary TB and ARDS", Int.J. Tuberc Lung Dis 7/4,359–64(Apr. 2003), also cited as PubMed Abstract, PMID:12733492.*

* cited by examiner

*Primary Examiner*—Mukund J. Shah
*Assistant Examiner*—Sudhaker B. Patel

(57) ABSTRACT

Novel 4-Biarylbutyric and 5-Biarylpentanoic Acid Derivatives, use of substituted 4-Biarylbutyric and 5-Biarylpentanoic Acid Derivatives as Matrix Metalloprotease Inhibitors for the Treatment of Respiratory Diseases, pharmaceutical compositions containing them, and a process for using them. The compounds of the invention have the generalized formula (I) $(T)_xA$—B—D—E—$CO_2H$ wherein A is an aryl or heteroaryl rings; B is an aryl or heteroaryl ring or a bond; each T is a substituent group, x is 0, 1, or 2; the group D represents (a), (b), (c), or (d); the group E represents a two or three carbon chain bearing one to three substituent groups which are independent or are involved in ring formation, possible structures being shown in the text and claims; and each of the substituents on E is an independent substituent; and include pharmaceutically acceptable salts thereof.

12 Claims, No Drawings

USE OF SUBSTITUTED 4-BIARYLBUTYRIC AND 5-BIARYLPENTANOIC ACID DERIVATIVES AS MATRIX METALLOPROTEASE INHIBITORS FOR THE TREATMENT OF RESPIRATORY DISEASES

FIELD

This invention relates to the use of enzyme inhibitors, and more particularly, to new and known matrix metalloprotease-inhibiting 4-Biarylbutyric Acids and 5-Biarylpentanoic Acids and derivatives thereof, for the prevention and treatment of respiratory diseases.

BACKGROUND

Substituted 4-Biarylbutyric and 5-Biarylpentanoic Acid Derivatives as Matrix Metalloprotease Inhibitors are described in WO 96/15096, WO 97/43237, WO 97/43238, WO 97/43239, WO 97/43240, WO 97/43245, WO 97/43247 and WO 98/22436.

The matrix metalloproteases (matrix metalloendoproteinases or MMPs) are a family of zinc endoproteinases which include, but are not limited to, interstitial collagenase (MMP-1), stromelysin (proteoglycanase, tansin, or MMP-3), gelatinase A (72 kDa-gelatinase or MMP-2), neutrophil collagenase (MMP-8), gelatinase B (95 kDa-gelatinase or MMP-9), macrophage elastase (MMP-12) and human collagenase 3 (MMP 13). These MMPs are secreted by a variety of cells including fibroblasts, chondrocytes, granulocytes and macrophages along with natural proteinatious inhibitors known as TIMPs (Tissue Inhibitor of MetalloProteinase).

All of these MMPs are capable of destroying a variety of connective tissue components of articular cartilage or basement membranes and a wide variety of extracellular matrix proteins. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (A. Ho, H. Nagase, Arch. Biochem. Biophys., 267, 211–16 (1988); Y. Ogata, J. J. Enghild, H. Nagase, J. Biol. Chem., 267, 3581–84 (1992)). Thus, a cascade of proteolytic activity can be initiated by an excess of MMP-3. It follows that specific MMP-3 inhibitors should limit the activity of other MMPs that are not directly inhibited by such inhibitors.

In addition to its ability to degrade extracellular matrix proteins MMP-12 has also been shown to hydrolyse elastin (R. P. Mecham, T. J. Broekelmann, C. J. Fliszar, S. D. Shapiro, H. G. Welgus, R. M. Senior, J. Biol. Chem., 272, 18071–18076 (1997)). This activity is shared by other MMP enzymes, specifically MMP-2 and MMP-9.

It has also been reported that MMP-3, MMP-9 and MMP-12 can cleave and thereby inactivate the endogenous inhibitors of other proteinases such as elastase (P. G. Winyard, Z. Zhang, K. Chidwick, D. R. Blake, R. W. Carrell, G. Murphy, FEBS Letts., 279, 1, 91–94 (1991); T. J. Gronski, R. L. Martin, D. K. Kobayashi, B. C. Walsh, M. C. Holman, M. Huber, H. E. Van Wart, S. D. Shapiro, J. Biol. Chem., 272, 12189–12194 (1997)). Inhibitors of these MMP enzymes could thus influence the activity of other destructive proteinases by modifying the level of their endogenous inhibitors.

Macrophages from MMP-12 knock-out mice have a diminished capacity to degrade extracellular matrix components and to penetrate reconstituted basement membranes both in vitro and in vivo (J. M. Shipley, R. L. Wesselschmidt, D. K. Kobayashi, T. J. Ley, S. D. Shapiro, PNAS, 93, 3942–3946 (1996)). These results support the hypothesis that MMP-12 is required for macrophage mediated extracellular proteolysis and tissue invasion. In addition, MMP-12 knock-out mice do not develop emphysema or show elevated macrophage levels in response to smoking, whereas wild type mice do (R. D. Hautamaki, D. K. Kobayashi R. M. Senior, S. D. Shapiro, Science, 277, 2002–2004 (1997)). Therefore there is strong evidence supporting a role of M-12, secreted by activated alveolar macrophages, in the development of pulmonary emphysema In patients with emphysema and smoking subjects both MMP-1, -8, -9 and -12 released from alveolar macrophages and neutrophils are also implicated in the pathogenesis of COPD.

By means of their proteolytic activity, matrix metalloproteases are involved in a number of respiratory diseases, e.g. the following:

asthma; chronic obstructive pulmonary disease including chronic bronchitis and emphysema; cystic fibrosis; bronchiectasis; adult respiratory distress syndrom (ARDS); allergic respiratory disease including allergic rhinitis; diseases linked to $TNF_\alpha$ production including acute pulmonary fibrotic diseases, pulmonary sarcoidosis, silicosis, coal worker's pneumoconiosis, alveolar injury.

Evidence for the involvement of matrix metalloproteases in various respiratory diseases is provided by the following references:

| | | |
|---|---|---|
| a) COPD, chronic bronchitis and emphysema | Finlay et al. | Thorax 1997, 52, 502 |
| | | Am. J. Resp. Crit Care Med. 1997, 156, 240 |
| | Cateldo et al. | Am. J. Resp. Crit. Care Med. 1998, 157, A 502 |
| | Sedura et al. | Am. J. Resp. Crit. Care Med. 1998, 157, A 568 |
| | Shapiro et al. | J. Biol. Chem. 1993, 268, 23824 |
| | Kostan et al. | Am. J. Resp. Crit. Care Med. 1998, 157, A 143 |
| | Riccobono | Eur. Resp. J. 1997, 10, 26S |
| b) bronchiectasis | Sepper et al. | Chest 1995, 107, 1641 |
| | Sepper et al. | Eur. Resp. J. 1997, 10, 278S |
| c) cystic fibrosis | Delacourt et al. | Am. J. Resp. Crit. Care Med. 1995, 152, A 764 |
| | Power et al. | Am. J. Resp. Crit. Care Med. 1994, 150, 818 |
| d) asthma | Shute et al. | Int. Arch. Allergy Immunol. 1997, 111 |
| | Ohno et al. | Am. J. Resp. Cell. Mol. Biol. 1997, 16, 212 |
| | Mantino et al. | Am. J. Resp. Cell. Mol. Biol. 1997, 17, 583 |
| | Okada et al. | Am. J. Resp. Cell. Mol. Biol. 1997, 17, 519 |
| e) ARDS | Delclaux et al. | Am. J. Physiol. 1997, 272, L442. |

In addition to chronic lung diseases a number of other conditions are thought to be mediated by excess or undesired matrix-destroying metalloprotease activity or by an imbalance in the ratio of the MMPs to the TIMPs or through the action of the release of TNF.

MMP inhibitors may also be useful in the inhibition of other mammalian metalloproteases such as the adamalysin family (or ADAMs) whose members include $TNF_\alpha$ converting enzyme (TACE) and ADAM-10, which can cause the release of TNF from cells.

SUMMARY

This invention relates to the use for the prevention and treatment of respiratory diseases of new and known compounds having matrix metallprotease inhibitory activity of the generalized formula (I):

$$(T)_xA—B—D—E—CO_2H. \qquad (I)$$

In the above generalized formula (I), $(T)_xA$ represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring, designated as the A ring or A unit. When N is employed in conjunction with either S or O in the A ring, these heteroatoms are separated by at least one carbon atom.

The substituent group(s) T are independently selected from the group consisting of halogen; alkyl; haloalkyl; haloalkoxy; alkenyl; alkynyl; —$(CH_2)_pQ$ in which p is 0 or an integer of 1–4; -alkenyl-Q in which the alkenyl moiety comprises 2–4 carbons; and alkynyl-Q in which the alkynyl moiety comprises 2–7 carbons. Q in the latter three groups is selected from the group consisting of aryl, heteroaryl, —CN, —CHO, —$NO_2$, —$CO_2R^2$, —$OCOR^2$, —$SOR^3$, —$SO_2R^3$, —$CON(R^4)_2$, —$SO_2N(R^4)_2$, —$COR^2$, —$N(R^4)_2$, —$N(R^2)COR^2$, —$N(R^2)CO_2R^3$, —$N(R^2)CON(R^4)_2$, —$CHN_4$, $OR^4$, and —$SR^4$.

In these formulae $R^2$ represents H, alkyl, aryl, heteroaryl, arylalkyl, or heteroaryl-alkyl. $R^3$ represents alkyl, aryl, heteroaryl, arylalkyl, or heteroaryl-alkyl. $R^4$ represents H; alkyl; aryl; heteroaryl; arylalkyl; heteroaryl-alkyl; alkenyl; alkynyl; alkyleneoxy, polyalkyleneoxy, alkylenethio or alkyleneamino terminated with H, alkyl, or phenyl; haloalkyl; lower alkoxycarbonyl; or acyl. When two $R^4$ groups are situated on a nitrogen, they may be joined by a bond to form a heterocycle, such as, for example, a morpholine, thiomorpholine, pyrrolidine, or piperidine ring.

Unsaturation in a moiety which is attached to Q or which is part of Q is separated from any N, O, or S of Q by at least one carbon atom. The A ring may be unsubstituted or may carry up to 2 substituents T. Accordingly, the subscript x is 0, 1, or 2.

In the generalized formula (I), B represents a bond or an optionally substituted aromatic 6-membered ring or a heteroaromatic 5–6 membered ring containing 1–2 atoms of N, O, or S. When B is a ring, it is referred to as the B ring or B unit. When N is employed in conjunction with either S or O in the B ring, these heteroatoms are separated by at least one carbon atom. There may be 0–2 substituents T on ring B.

In the generalized formula (I), D represents

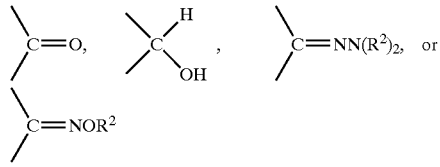

in which $R^2$ is defined as above and each $R^2$ may be the same or different.

In the generalized formula (I), E represents a chain of n carbon atoms bearing m substituents $R^6$, in which the $R^6$ groups are independent substituents, or constitute spiro or nonspiro rings. Rings may be formed in two ways: a) two groups $R^6$ are joined, and taken together with the chain atom(s) to which the two $R^6$ group(s) are attached, and any intervening chain atoms, constitute a 3–7 membered ring, or b) one group $R^6$ is joined to the chain on which this one group $R^6$ resides, and taken together with the chain atom(s) to which the $R^6$ group is attached, and any intervening chain atoms, constitutes a 3–7 membered ring. The number n of carbon atoms in the chain is 2 to 4, and the number m of $R^6$ substituents is an integer of 1–3.

Each group $R^6$ is independently selected from the group consisting of:

fluorine;

hydroxyl, with the proviso that a single carbon atom may bear no more than one hydroxyl group;

alkyl;

aryl;

heteroaryl;

arylalkyl;

heteroaryl-alkyl;

alkenyl;

aryl-substituted alkenyl;

heteroaryl-substituted alkenyl;

alkynyl;

aryl-substituted alkynyl;

heteroaryl-substituted alkynyl;

—$(CH_2)_tR^7$, wherein t is 0 or an integer of 1–5 and $R^7$ is selected from the group consisting of:

N-phthalinidoyl;

N-(1,2-naphthalenedicarboximidoyl);

N-(2,3-naphthalenedicarboximidoyl);

N-(1,8-naphthalenedicarboximidoyl);

N-indoloyl;

N-(2-pyrrolodinonyl);

N-succiniimidoyl;

N-maleimidoyl;

3-hydantoinyl;

1,2,4-urazolyl;

amido;

urethane;

urea;

nonaromatic substituted or unsubstituted heterocycles containing and connected through a N atom, and comprising one or two additional N, O, S, SO, or $SO_2$, and containing zero, one or two carbonyls, and optionally bearing a fused benzene or pyridine ring;

amino;

corresponding heteroaryl moieties in which the aryl portion of an aryl-containing $R^7$ group comprises 4–9 carbons and at least one N, O, or S heteroatom;

$(CH_2)_vZR^8$ in which v is 0 or an integer of 1–4, wherein Z represents

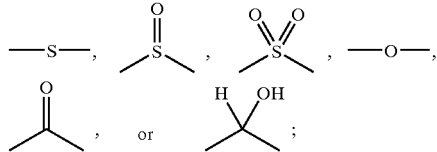

and $R^8$ is selected from the group consisting of:

alkyl;

aryl;

heteroaryl;

arylalkyl;

heteroaryl-alkyl; and

—C(O)R⁹ in which R⁹ represents alkyl of at least two carbons, aryl, heteroaryl, arylalkyl, or heteroaryl-alkyl;

and with the further provisos that
when R⁸ is —C(O)R⁹, Z is S or O;
when Z is O, R⁸ may also be alkyleneoxy or polyalkyleneoxy terminated with H, alkyl, or phenyl; and trialkylsilyl-substituted alkyl.

Furthermore, aryl or heteroaryl portions of any of the T or R⁶ groups optionally may bear up to two substituents selected from the group consisting of —(CH₂)ᵧC(R⁴)(R³)OH, —(CH₂)ᵧOR⁴, —(CH₂)ᵧSR⁴, —(CH₂)ᵧS(O)R⁴, —(CH₂)ᵧS(O)₂R⁴, —(CH₂)ᵧSO₂N(R⁴)₂, —(CH₂)ᵧN(R⁴)₂, —(CH₂)ᵧN(R⁴)COR¹², —OC(R⁴)₂O— in which both oxygen atoms are connected to the aryl ring, (CH₂)ᵧCOR⁴, —(CH₂)ᵧCON(R⁴)₂, —(CH₂)ᵧCO₂R⁴, —(CH₂)ᵧOCOR⁴, -halogen, —CHO, —CF₃, —NO₂, —CN, and —R³, in which y is 0–4. R³ and R⁴ are defined as above; in addition, any two R⁴ which are attached to one nitrogen may be joined to form a heterocycle such as morpholine, thiomorpholine, pyrrolidine, or a piperidine ring.

Pharmaceutically acceptable salts of these compounds as well as commonly used prodrugs of these compounds such as O-acyl derivatives of invention compounds which contain hydroxy groups are also within the scope of the invention.

In most related reference compounds of the prior art, the biphenyl portion of the molecule is unsubstituted, and the propanoic or butanoic acid portion is either unsubstituted or has a single methyl or phenyl group. Presence of the larger phenyl group has been reported to cause prior art compounds to be inactive as anti-inflammatory analgesic agents. See, for example, R. G. Child, et al., J. Pharm. Sci., 66, 466–476 (1977). By contrast, it has now been found that compounds which exhibit potent MMP inhibitory activity contain a substituent of significant size on the a propanoic or butanoic portion of the molecule. The biphenyl portions of the best MMP inhibitors also preferably contain a substituent on the 4' position, although when the propanoic or butanoic portions are optimally substituted, the unsubstituted biphenyl compounds of the invention have sufficient activity to be considered realistic drug candidates.

The compounds of the present invention exhibit good activity for MMP-2, MMP-3, MMP-8, MMP-9, MMP-12 and MMP-13, and a good selectivity for these MMP's over other MMP's such as MMP-1 and MMP-7.

In addition to the above-described compounds, the invention also relates to pharmaceutical compositions having matrix metalloprotease inhibitory activity, which compositions comprise a compound of the invention as described above and in more detail in the detailed description below, and a pharmaceutically acceptable carrier.

As a result of the abovementioned selectivity profile, the compounds of the present invention are especially suitable for the treatment of respiratory diseases.

Therefore, the invention also relates to a method of treating a mammal such as a human, a farm animal, or a domestic pet, to achieve an effect, in which the effect is: treatment and prevention of asthma; chronic obstructive pulmonary disease including chronic bronchitis and emphysema; cystic fibrosis; bronchiectasis; adult respiratory distress syndrome (ARDS); allergic respiratory disease including allergic rhinitis; diseases linked to TNFα production including acute pulmonary fibrotic diseases, pulmonary sarcoidosis, silicosis, coal worker's pneumoconiosis, alveolar injury; the method comprising administering an amount of a compound of the invention as described above, and in more detail in the detailed description below, which is effective to inhibit the activity of at least one matrix metalloprotease, resulting in achievement of the desired effect.

DETAILED DESCRIPTION

More particularly preferred are for the use for the prevention and treatment of respiratory diseases are compounds having matrix metalloprotease inhibitory activity of the generalized formula:

(T)ₓA—B—D—E—CO₂H  (I)

in which (T)ₓA represents a substituted or unsubstituted aromatic or heteroaromatic moiety selected from the group consisting of:

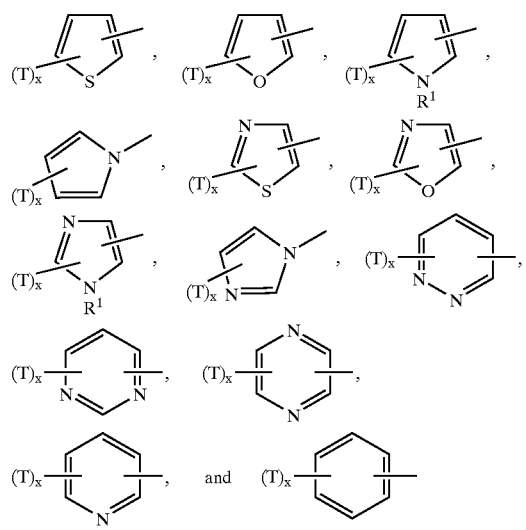

in which R¹ represents H or alkyl of 1–3 carbons.

In these structures, the aromatic ring is referred to as the A ring or A unit, and each T represents a substituent group, referred to as a T group or T unit. Substituent groups T are independently selected from the group consisting of: the halogens —F, —Cl, —Br, and —I; alkyl of 1–10 carbons; haloalkyl of 1–10 carbons; haloalkoxy of 1–10 carbons; alkenyl of 2–10 carbons; alkynyl of 2–10 carbons; —(CH₂)ₚQ in which p is 0 or an integer 1–4; -alkenyl-Q in which the alkenyl moiety comprises 2–4 carbons; and -alkynyl-Q in which the alkenyl moiety comprises 2–7 carbons. Q in each of the latter three groups is selected from the group consisting of aryl of 6–10 carbons; heteroaryl comprising 4–9 carbons and at least one N, O, or S heteroatom; —CN; —CHO; —NO₂; —CO₂R²; —OCOR²; —SOR³; —SO₂R³; CON(R⁴)₂; —SO₂N(R⁴)₂; —C(O)R²; —N(R⁴)₂; —N(R²)COR²; —N(R²)CO₂R³; —N(R²)CON(R⁴)₂; —CHN₄; —OR⁴; and —SR⁴. The groups R², R³, and R⁴ are defined as follows.

R² represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R³ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons, or heteroaryl-alkyl in which the heteroaryl portion comprises 4–9 carbons and at least one N, O, or S heteroatom and the alkyl portion contains 1–4 carbons, $R^4$ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —$(C_qH_{2q}O)_rR^5$ in which q is 1–3, r is 1–3, and $R^5$ is H provided q is greater than 1, or $R^5$ is alkyl of 1–4 carbons, or phenyl; alkylenethio terminated with H, alkyl of 1–4 carbons, or phenyl; alkyleneamino terminated with H, alkyl of 1–4 carbons, or phenyl; —$(CH_2)_sX$ in which s is 1–3 and X is halogen; —$C(O)OR^2$; or —$C(O)R^2$.

When two $R^4$ groups are situated on a nitrogen, they may be joined by a bond to form a heterocycle, such as, for example, a morpholine, thiomorpholine, pyrrolidine, or piperidine ring.

Any unsaturation in a moiety which is attached to Q or which is part of Q is separated from any N, O, or S of Q by at least one carbon atom, and the number of substituents, designated x, is 0, 1, or 2.

In the generalized formula (I), B represents a bond or an optionally substituted aromatic or heteroaromatic ring selected from the group consisting of:

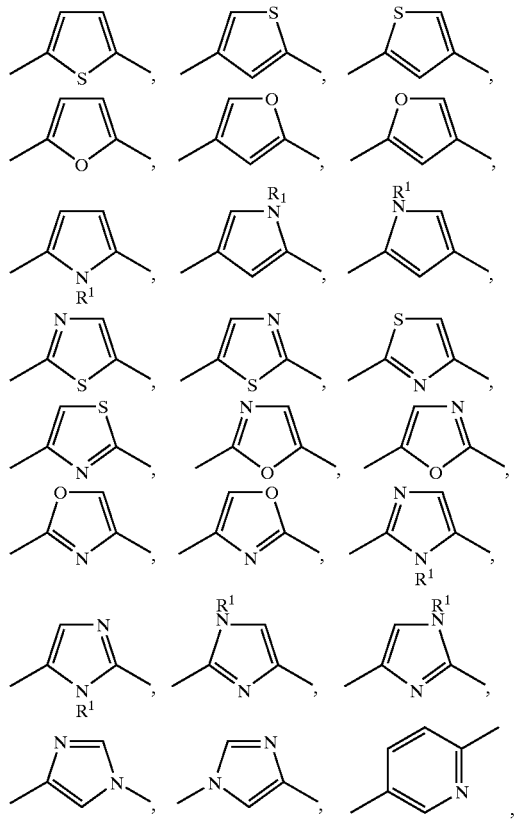

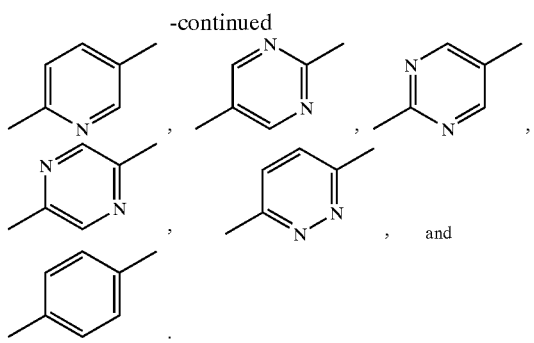

in which $R^1$ is defined as above. These rings are referred to as the B ring or B unit. There may be 0–2 substituents T on the B ring, T being defined as above.

In the generalized formula (I), D represents the moieties

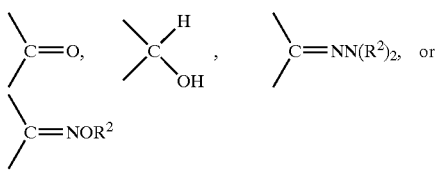

in which $R^2$ is defined as above and each $R^2$ may be the same or different.

In the generalized formula (I), E represents a chain of n carbon atoms bearing m substituents $R^6$, referred to as $R^6$ groups or $R^6$ units. The $R^6$ groups are independent substituents, or constitute spiro or nonspiro rings. Rings may be formed in two ways: a) two groups $R^6$ are joined, and taken together with the chain atom(s) to which the two R6 group(s) are attached, and any intervening chain atoms, constitute a 3–7 membered ring, or b) one group $R^6$ is joined to the chain on which this one group $R^6$ resides, and taken together with the chain atom(s) to which the $R^6$ group is attached, and any intervening chain atoms, constitutes a 3–7 membered ring. The number n of carbon atoms in the chain is 2 or 3, and the number m of $R^6$ substituents is an integer of 1–3.

Each group $R^6$ is independently selected from the group consisting of the substituents listed below as items 1)–16).

1) fluorine;
2) hydroxyl, with the proviso that a single carbon atom may bear no more than one hydroxyl group;
3) alkyl of 1–10 carbons;
4) aryl of 6–10 carbons;
5) heteroaryl comprising 4–9 carbons and at least one N, O, or S heteroatom;
6) arylalkyl in which the aryl portion contains 6–10 carbons and the alkyl portion contains 1–8 carbons;
7) heteroaryl-alkyl in which the heteroaryl portion comprises 4–9 carbons and at least one N, O, or S heteroatom, and the alkyl portion contains 1–8 carbons;
8) alkenyl of 2–10 carbons;
9) aryl-alkenyl in which the aryl portion contains 6–10 carbons and the alkenyl portion contains 2–5 carbons;
10) heteroaryl-alkenyl in which the heteroaryl portion comprises 4–9 carbons and at least one N, O, or S heteroatom and the alkenyl portion contains 2–5 carbons;

11) alkynyl of 2–10 carbons;

12) aryl-alkynyl in which the aryl portion contains 6–10 carbons and the alkynyl portion contains 2–5 carbons;

13) heteroaryl-alkynyl in which the heteroaryl portion comprises 4–9 carbons and at least one N, O, or S heteroatom and the alkynyl portion contains 2–5 carbons;

14) —(CH$_2$)$_t$R$^7$ in which t is 0 or an integer of 1–5 and R$^7$ is selected from the group consisting of

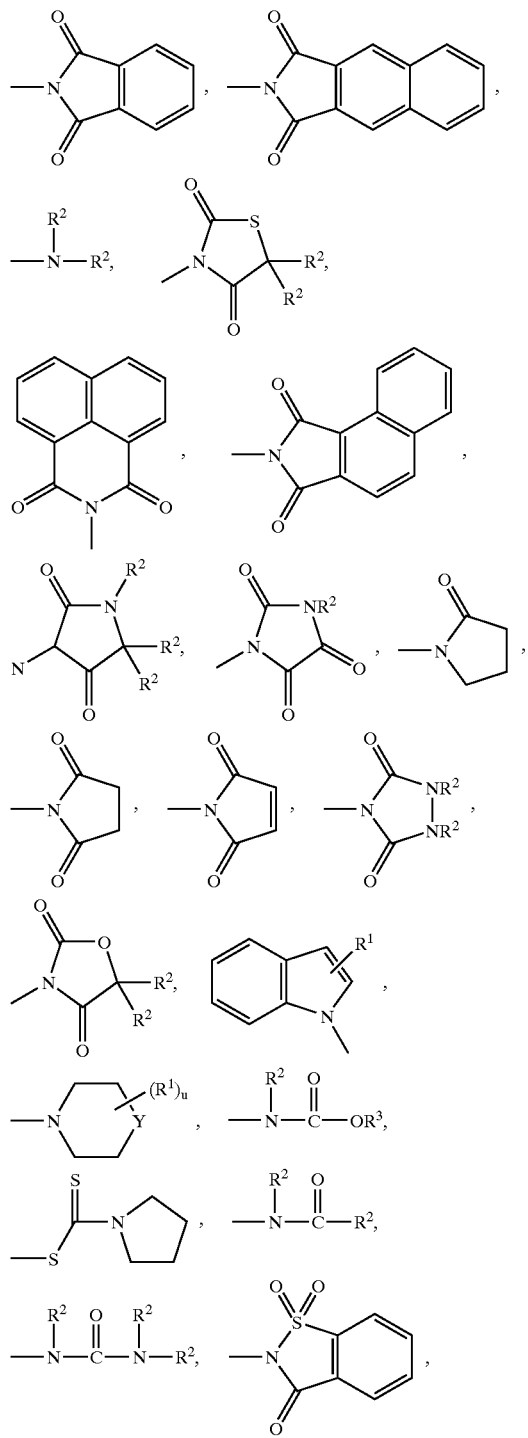

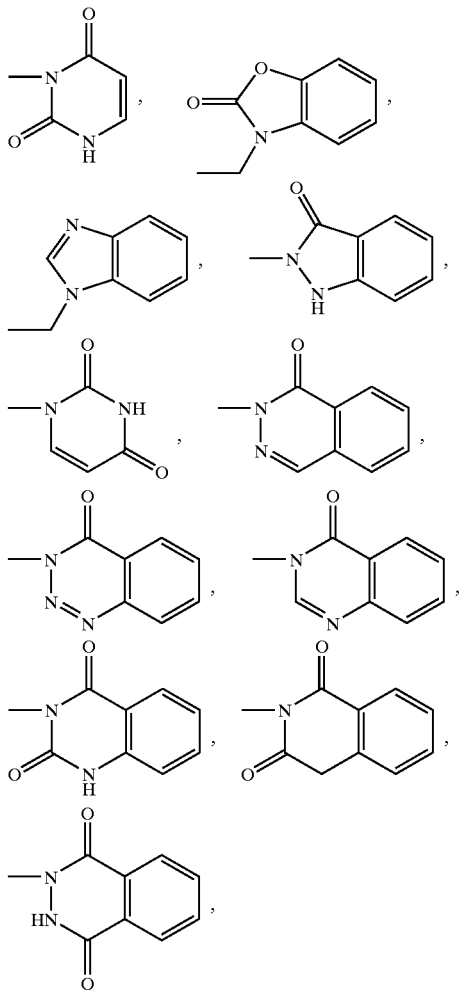

as well as corresponding heteroaryl moieties in which the aryl portion of an aryl-containing R$^7$ group comprises 4–9 carbons and at least one N, O, or S heteroatom. In such R$^7$ groups, Y represents O or S; R$^1$, R$^2$, and R$^3$ are as defined above; and u is 0, 1, or 2;

15) —(CH$_2$)$_v$ZR$^8$ in which v is 0 or an integer of 1 to 4; Z represents —S—, —S(O)—, —SO$_2$—, —O—, carbonyl, or —CH(OH)—; and R$^8$ is selected from the group consisting of: alkyl of 1 to 12 carbons; aryl of 6 to 10 carbons; heteroaryl comprising 4–9 carbons and at least one N, O, or S heteroatom; arylalkyl in which the aryl portion contains 6 to 12 carbons and the alkyl portion contains 1 to 4 carbons; heteroaryl-alkyl in which the aryl portion comprises 4–9 carbons and at least one N, O, or S heteroatom and the alkyl portion contains 1–4 carbons; —C(O)R$^9$ in which R$^9$ represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons, with the provisos that when R$^8$ is —C(O)R$^9$, Z is —S— or —O—;

when Z is —O—, R$^8$ may also be —(C$_q$H$_{2q}$O)$_r$R$^5$ in which q, r, and R$^5$ are as defined above;

16) —(CH$_2$)$_w$Si(R$^{10}$)$_3$ in which w is an integer of 1 to 3, and R$^{10}$ represents alkyl of 1 to 4 carbons.

In addition, aryl or heteroaryl portions of any of the T or $R^6$ groups optionally may bear up to two substituents selected from the group consisting of —$(CH_2)_yC(R^4)(R^3)$OH, —$(CH_2)_yOR^4$), —$(CH_2)_ySR^4$), —$(CH_2)_yS(O)R^4$), —$(CH_2)_yS(O)_2R^4$), —$(CH_2)_ySO_2N(R^4))_2$, —$(CH_2)_yN(R^4))_2$, —$(CH_2)_yN(R^4))COR^3$, —$OC(R^4))_2O$— in which both oxygen atoms are connected to the aryl ring, —$(CH_2)_y$ $COR^4$, —$(CH_2)_yCON(R^4))_2$, —$(CH_2)_yCO_2R^4$), —$(CH_2)_y$ $OCOR^4$), -halogen, —CHO, —$CF_3$, —$NO_2$, —CN, and —$R^3$, in which y is 0–4; $R^3$ is defined as above; $R^4$ is defined as above and in addition, any two $R^4$ which are attached to one nitrogen may be joined to form a heterocycle, such as a morpholine, thiomorpholine, pyrrolidine, or piperidine ring.

Pharmaceutically acceptable salts of these compounds as well as commonly used prodrugs of these compounds such as O-acyl derivatives of these compounds are also within the scope of the invention.

In the compounds of the invention, the following are preferred.

The substituent group T, when it is on the ring A, is preferably halogen, 1-alkynyl-Q, or an ether $OR^4$ wherein $R^4$ is preferably alkyl of 1–12 carbons or arylalkyl in which the aryl portion is 6–10 carbons and the alkyl portion contains 1–4 carbons. Most preferably, T is halogen, or —C≡C—$(CH_2)_tOH$ in which t is an integer of 1–5, and when T is $OR^4$, $R^4$ is alkyl of 1–6 carbons, or benzyl.

The subscript x, which defines the number of T substituents, is preferably 1 or 2, most preferably 1, and this substituent T is preferably on the 4-position of ring A.

The A ring is preferably a phenyl or thiophene ring, most preferably phenyl. The A ring preferably bears at least one substituent group T, preferably located on the position furthest from the position of the A ring which is connected to the B ring.

The B moiety of generalized formula (I) is a bond or a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such groups may be, but are not limited to, moieties such as lower alkyl, lower alkoxy, CN, $NO_2$, halogen, etc. The B moiety is preferably a 1,4-phenylene or 2,5-thiophene ring, most preferably 1,4-phenylene.

The D unit is most preferably a carbonyl or a —CHOH— group.

The group $R^6$ is preferably:
1) arylalkyl wherein the aryl portion contains 6–10 carbons and the alkyl portion contains 1–8 carbons;
2) —$(CH_2)_tR^7$ wherein t is 0 or an integer of 1–5 and $R^7$ is an imidoyl group fused to an aromatic residue, or the 1,2,3-benzotriazin-4(3H)-one-3-yl group; or
3) —$(CH_2)_vZR^8$ wherein v is 0 or an integer of 1–4, Z is S or O, and $R^8$ is aryl of 6–10 carbons or arylalkyl wherein the aryl portion contains 6 to 12 carbons and the alkyl portion contains 1 to 4 carbons.

The group $R^6$ is most preferably one of the following, and in these, any aromatic moiety is preferably substituted:
1) arylalkyl wherein the aryl portion is phenyl and the alkyl portion contains 1–4 carbons;
2) —$(CH_2)_tR^7$ wherein t is an integer of 1–3, and $R^7$ is N-phthalimidoyl, 1,2,3-benzotriazin-4(3H)-one-3-yl, N-(1,2-naphthalenedicarboximidoyl), N-(2,3-naphthalenedicarboximidoyl), or N-(1,8-naphthalenedicarboximidoyl); or
3) —$(CH_2)_vZR^8$ wherein v is an integer of 1–3, Z is S, and $R^8$ is phenyl.

It is to be understood that as used herein, the term "alkyl" means straight, branched, cyclic, and polycyclic materials. The term "haloalkyl" means partially or fully halogenated alkyl groups such as —$(CH_2)_2Cl$, —$CF_3$ and —$C_6F_{13}$, for example.

In one of its embodiments, the invention relates to compounds of generalized formula (I) in which at least one of the units A, B, T, and $R^6$ comprises a hetero-aromatic ring. Preferred heteroaromatic ring-containing compounds are those in which the heteroaryl groups are heteroaryl of 4–9 carbons comprising a 5–6 membered heteroaromatic ring containing O, S; or $NR^1$ when the ring is 5-membered, and N when said ring is 6-membered. Particularly preferred hetero-aromatic ring-containing compounds are those in which at least one of the A and B units comprises a thiophene ring. When A unit is thiophene, it is preferably connected to B unit at position 2 and carries one substituent group T on position 5. When B Unit is thiophene, it is preferably connected through positions 2 and 5 to D and A units respectively.

In another embodiment, the invention relates to compounds of generalized formula (I), in the E unit of which n is 2 and m is 1. These compounds thus possess two carbon atoms between the D unit and carboxyl group, and carry one substituent on this two carbon chain.

In another of its embodiments, the invention relates to compounds of generalized formula (I) in which the A ring is a substituted or unsubstituted phenyl group, the B ring is phenylene, and aryl portions of any aryl containing T and $R^6$ moieties contain only carbon in the rings. These compounds thus contain no heteroaromatic rings.

In another of its embodiments, the invention relates to compounds of generalized formula (I) in which m is 1 and $R^6$ is an independent substituent. These compounds are materials which contain only a single substituent $R^6$ on the E unit, and this substituent in not involved in a ring.

Preferred compounds of general formula (I) in which $R^6$ is —$(CH_2)_tR^7$ have t as an integer of 1–5. Preferred compounds of general formula (I) in which $R^6$ is —$(CH_2)_vZR^8$ have v as an integer of 1–4 and Z as —S— or —O—. Preferred compounds of general formula (I) in which $R^6$ is alkyl contain 4 or more carbons in said alkyl and those in which $R^6$ is arylalkyl contain 2–3 carbons in the alkyl portion of said arylalkyl.

In another of its embodiments, the invention relates to compounds of generalized formula (I) in which the number of substituents m on the E unit is 2 or 3; and when m is 2, both groups $R^6$ are independent substituents, or together constitute a spiro ring, or one group $R^6$ is an independent substituent and the other constitutes a spiro ring; and when m is 3, two groups $R^6$ are independent substituents and one group $R^6$ constitutes a ring, or two groups $R^6$ constitute a ring and one group $R^6$ is an independent substituent, or three groups $R^6$ are independent substituents. This subset therefore contains compounds in which the E unit is di- or trisubstituted, and in the disubstituted case any rings formed by one or both $R^6$ groups are spiro rings, and in the trisubstituted case, the $R^6$ groups may form either spiro or nonspiro rings.

In another of its embodiments, the invention relates to compounds of generalized formula (I) in which the number of substituents m on the E unit is 1 or 2; and when m is 1, the group $R^6$ constitutes a nonspiro ring; and when m is 2, both groups $R^6$ together constitute a nonspiro ring or one group $R^6$ is an independent substituent and the other constitutes a nonspiro ring. This subset therefore contains compounds in which the E unit carries one or two substituents $R^6$, and at least one of these substituents is involved in a nonspiro ring.

More particularly, representative compounds of generalized formula (I) in which one or more of the substituent groups $R^6$ are involved in formation of nonspiro rings have E units of the following structures:

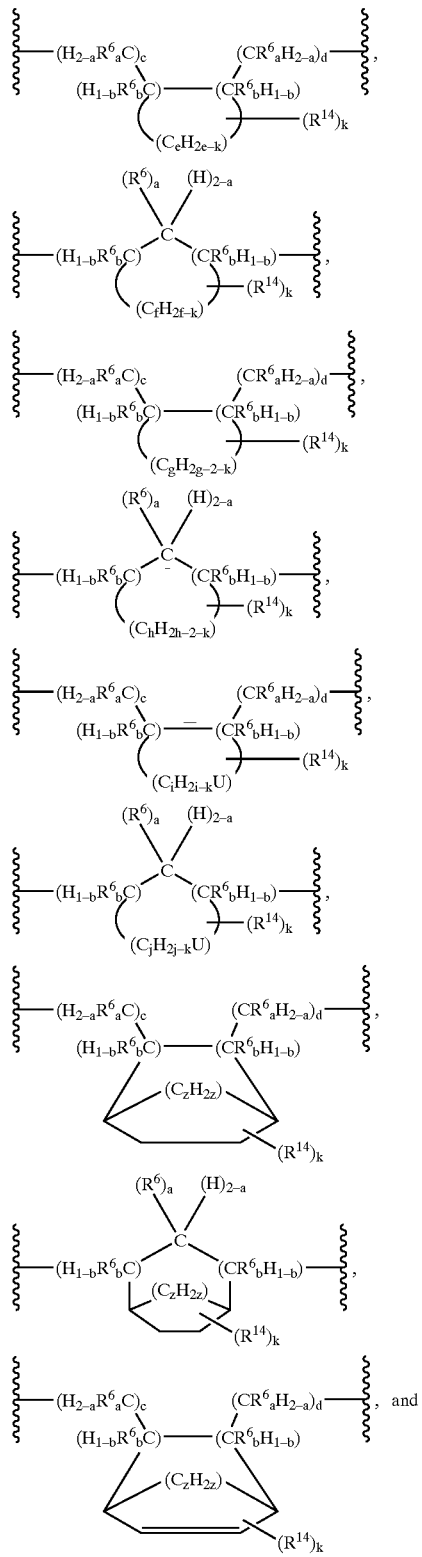

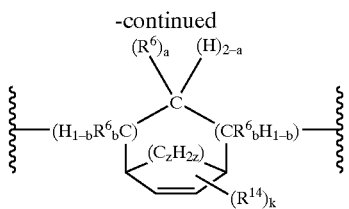

in which a is 0, 1, or 2; b is 0 or 1; c is 0 or 1; d is 0 or 1; c+d is 0 or 1; e is 1–5; f is 1–4; g is 3–5; h is 2–4; i is 0–4; j is 0–3; k is 0–2; the total number of groups $R^6$ is 0, 1, or 2; U represents O, S, or $NR^1$; and z is 1 or 2; Each group $R^{14}$ is independently selected from the group consisting of: alkyl of 1–9 carbons; arylalkyl in which the alkyl portion contains 1–7 carbons and the aryl portion contains 6–10 carbons; alkenyl of 2–9 carbons; aryl-substituted alkenyl in which the alkenyl portion contains 2–4 carbons and the aryl portion contains 6–10 carbons; alkynyl of 2–9 carbons; aryl-substituted alkynyl in which the alkynyl portion contains 2–4 carbons and the aryl portion contains 6–10 carbons; aryl of 6–10 carbons; $-COR^2$; $-CH(OH)R^2$; $-CO_2R^3$; $-CON(R^2)_2$; $-(CH_2)_tR^7$ in which t is 0 or an integer of 1–4; and $-(CH_2)_vZR^8$ in which v is 0 or an integer of 1 to 3, and Z represents $-S-$, S(O), $SO_2$, or $-O-$. $R^1$, $R^7$, and $R^8$ have been defined above.

Other preferred compounds of generalized formula (I) in which one or more of the substituent groups $R^6$ are involved in formation of nonspiro rings have E units of the following structures:

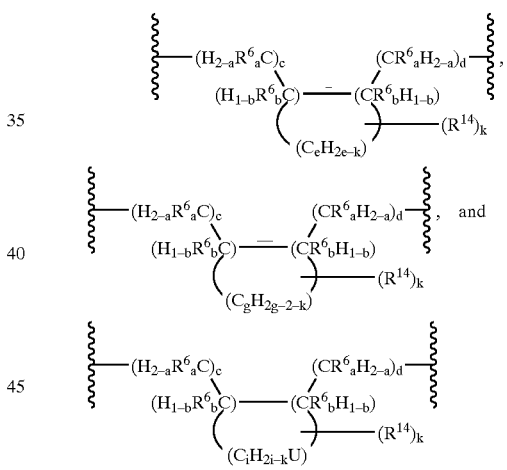

in which a, b, c, d, (c+d), e, g, i, k, the total number of groups $R^6$, U, and $R^{14}$ are as defined above.

Other preferred compounds for the use for the prevention and treatment of respiratory diseases of generalized formula (I), in which one or more of the substituent groups $R^6$ are involved in formation of nonspiro rings have the formula

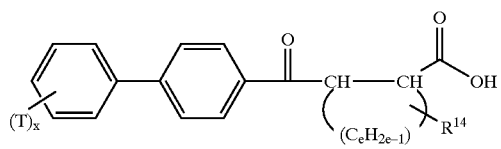

in which the subscript x is 1 or 2; one substituent T is located on the 4-position of the A ring, relative to the point of attachment between the A and B rings; e is 2 or 3; and $R^{14}$ is as defined above.

More preferred compounds are those shown in table 1:
TABLE 1
| No. | Structure |
|---|---|
| C-I | 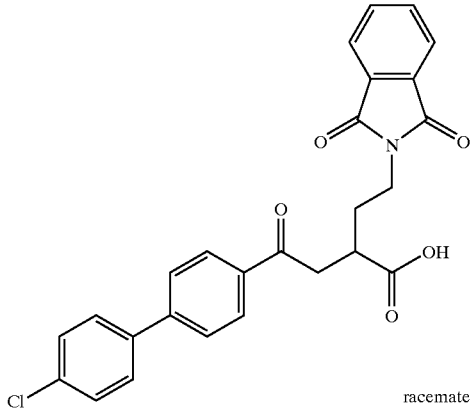 racemate |
| C-II | 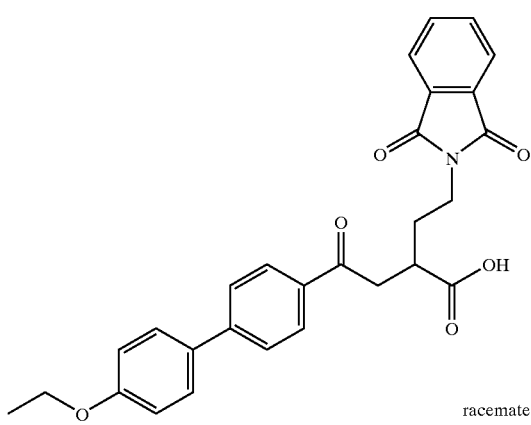 racemate |
| C-III | 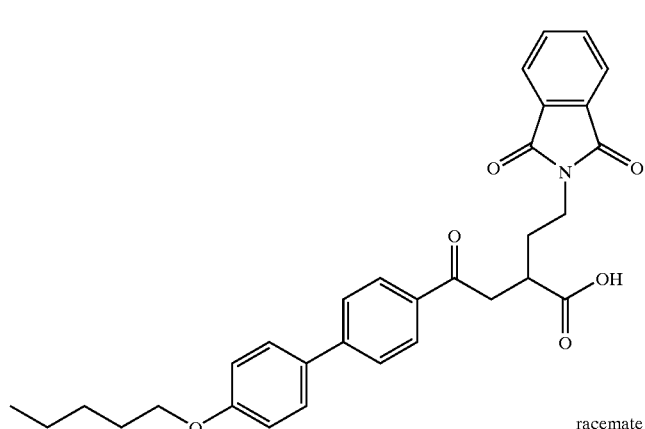 racemate |

TABLE 1-continued
| No. | Structure |
|---|---|
| C-IV | 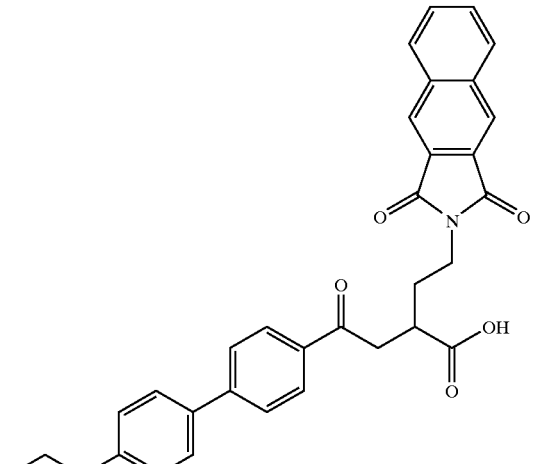<br>racemate |
| C-V | 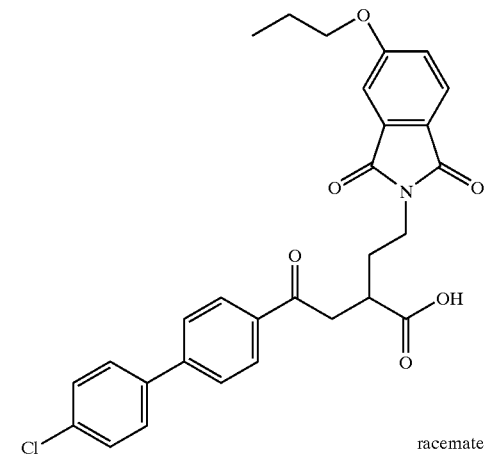<br>racemate |
| C-VI | 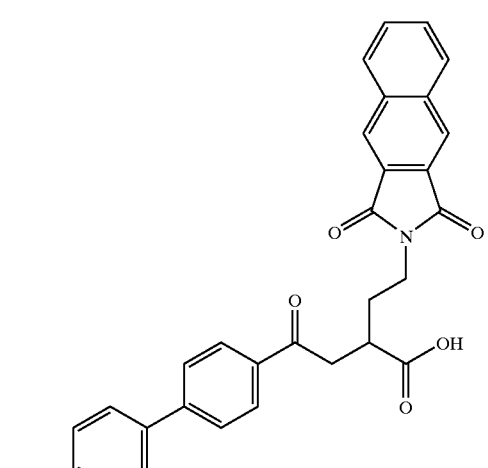<br>racemate |

TABLE 1-continued
| No. | Structure |
|---|---|
| C-VII | 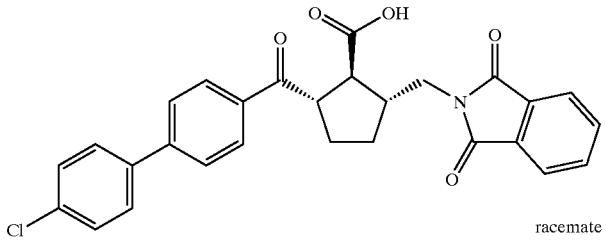 racemate |
| C-VIII | 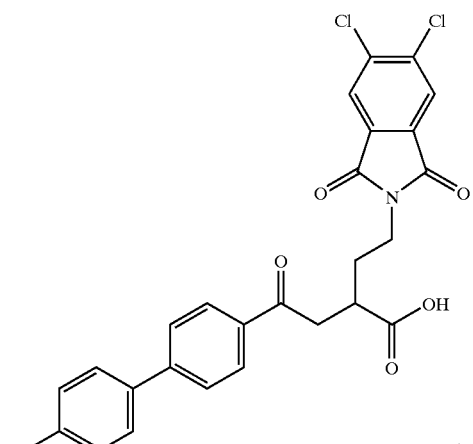 racemate |
| C-IX | 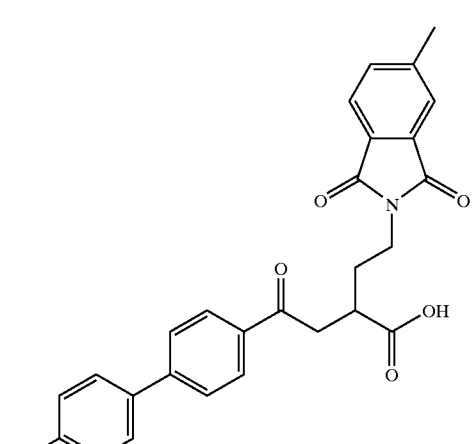 racemate |
| C-X | 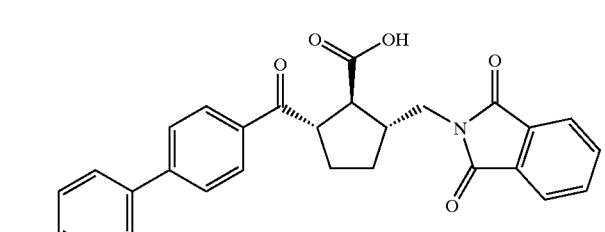 1S-enant. to C-VII |

TABLE 1-continued
| No. | Structure |
|---|---|
| C-XI | 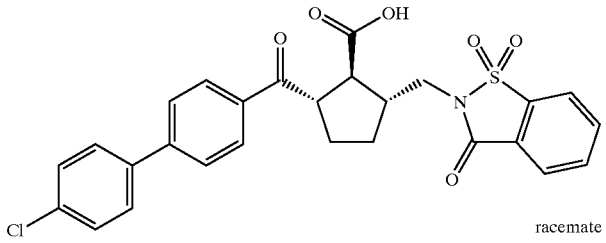<br>racemate |
| C-XII | 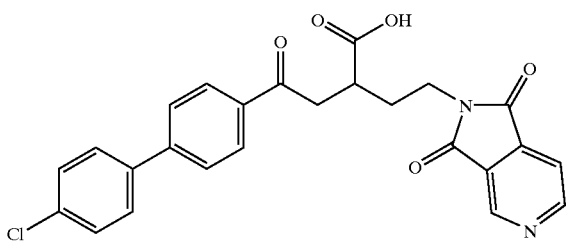<br>racemate |
| C-XIII | 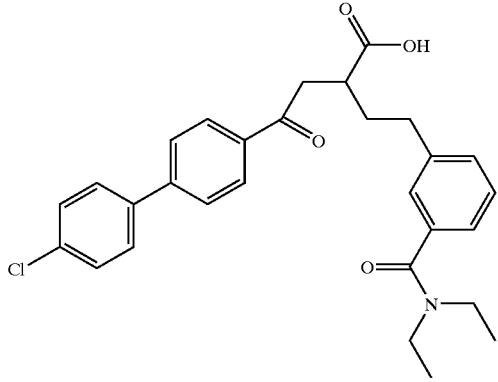<br>racemate |
| C-XIV | 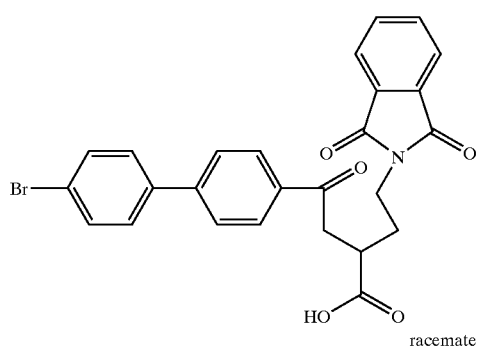<br>racemate |

TABLE 1-continued
| No. | Structure |
|---|---|
| C-XV | 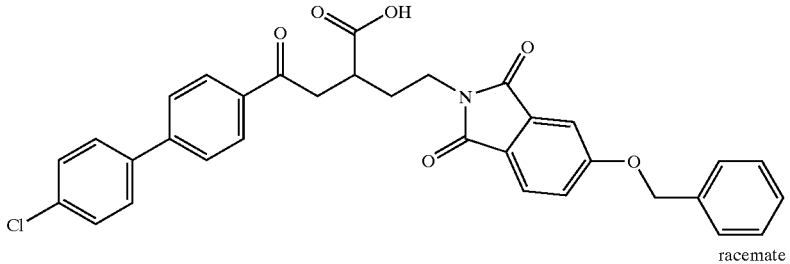<br>racemate |
| C-XVI | 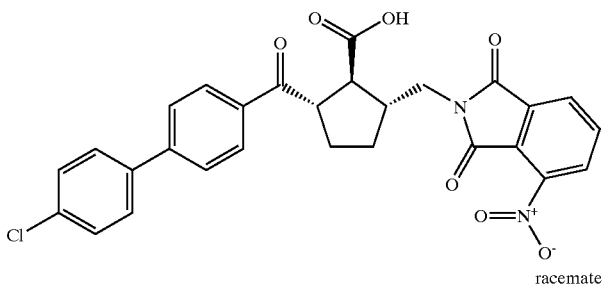<br>racemate |
| C-XVII | 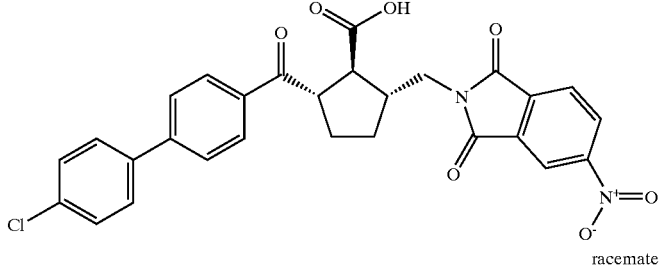<br>racemate |
| C-XVIII | 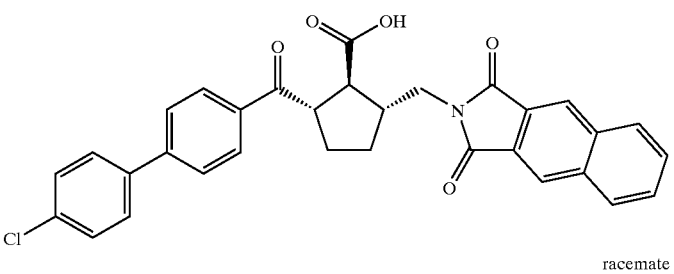<br>racemate |
| C-XIX | 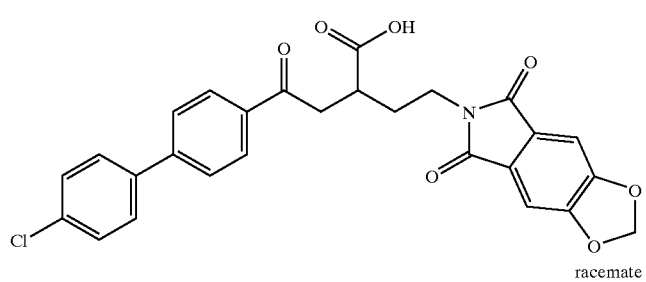<br>racemate |

TABLE 1-continued
| No. | Structure |
|---|---|
| C-XX | 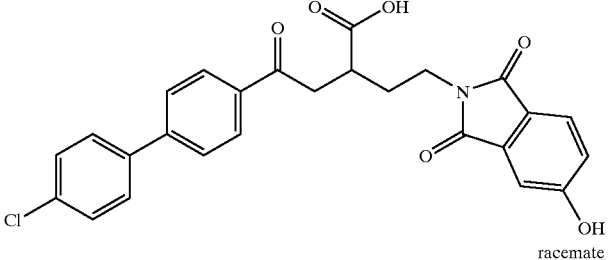<br>racemate |
| C-XXI | 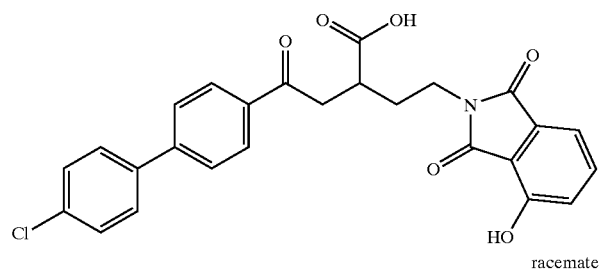<br>racemate |
| C-XXII | 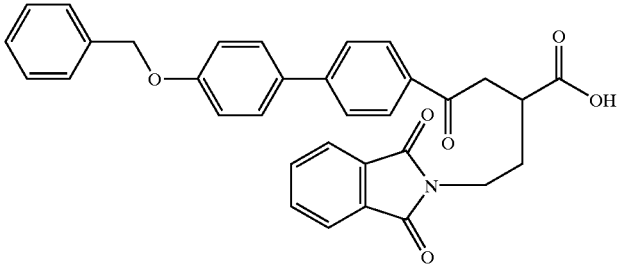<br>racemate |
| C-XXIII | 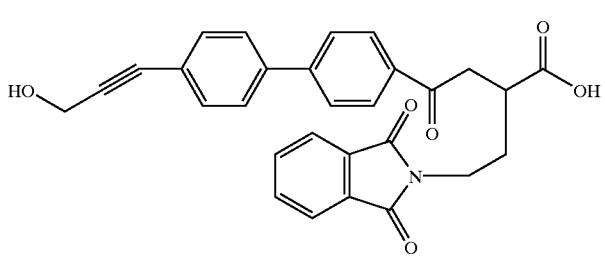<br>racemate |
| C-XXIV | 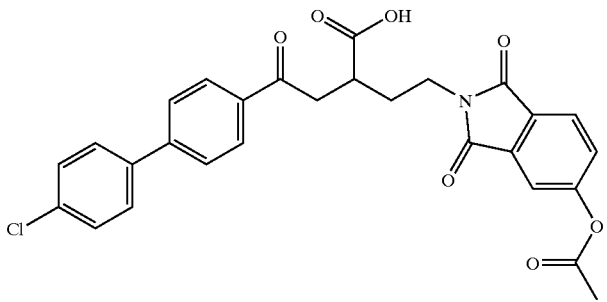<br>racemate |

TABLE 1-continued
| No. | Structure |
|---|---|
| C-XXV | 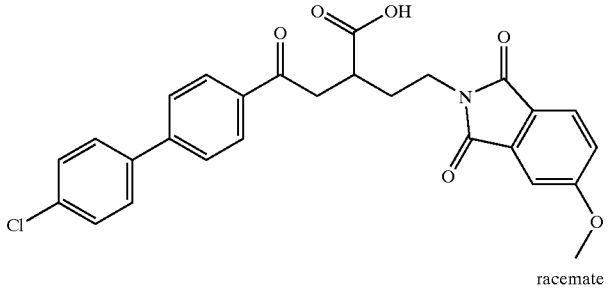<br>racemate |
| C-XXVI | 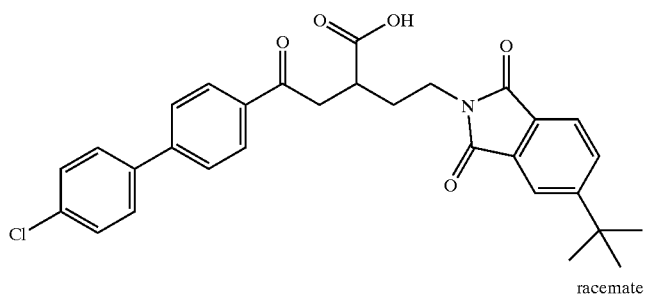<br>racemate |
| C-XXVII | 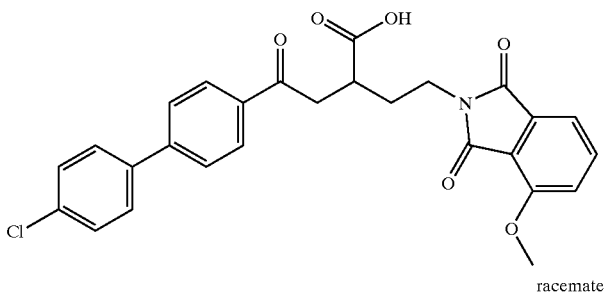<br>racemate |
| C-XXVIII | 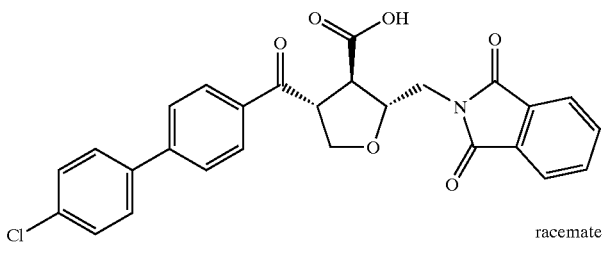<br>racemate |
| C-XXIX | 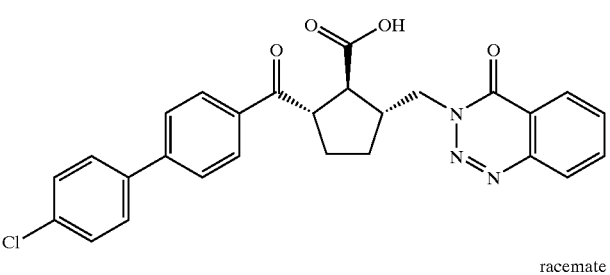<br>racemate |

TABLE 1-continued
| No. | Structure |
|---|---|
| C-XXX | 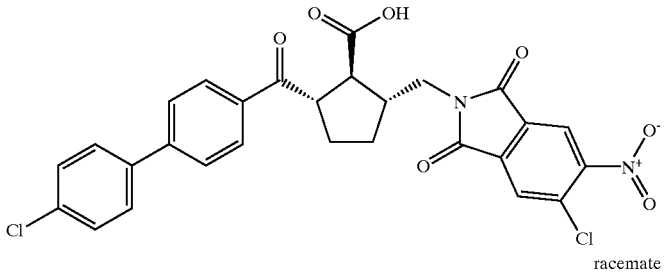 racemate |
| C-XXXI | 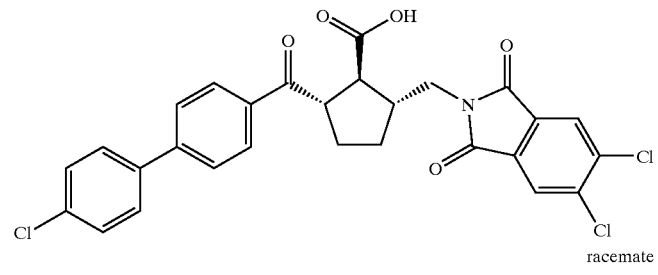 racemate |
| C-XXXII | 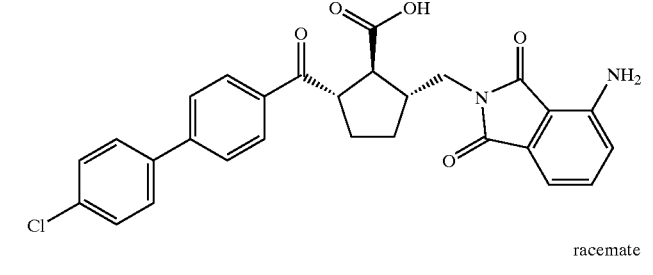 racemate |
| C-XXXIII | 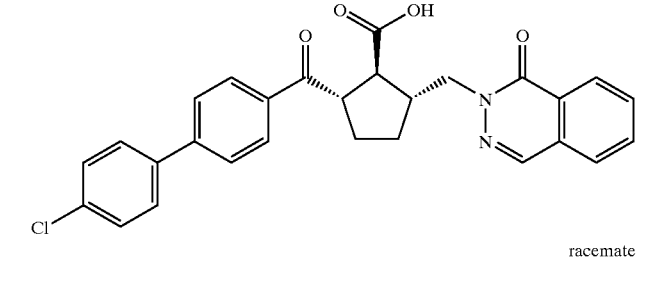 racemate |
| C-XXXIV | 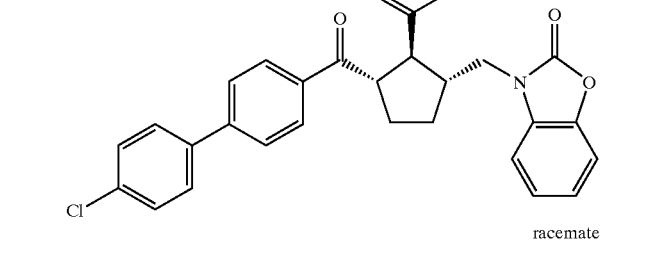 racemate |

TABLE 1-continued

| No. | Structure |
|---|---|
| C-XXXV | 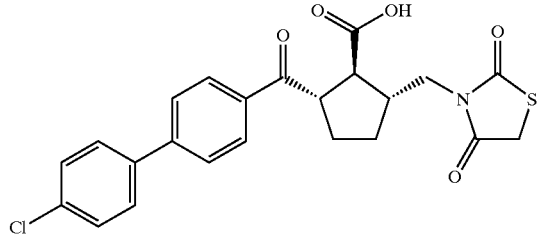 racemate |
| C-XXXVI | 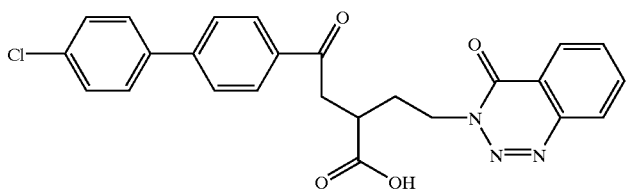 racemate |
| C-XXXVII | 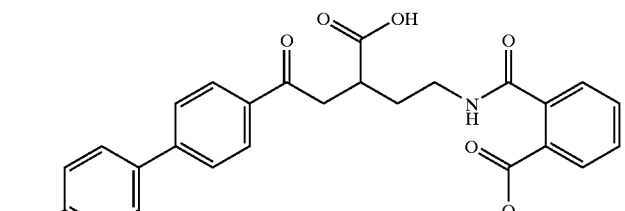 racemate |
| C-XXXVIII | 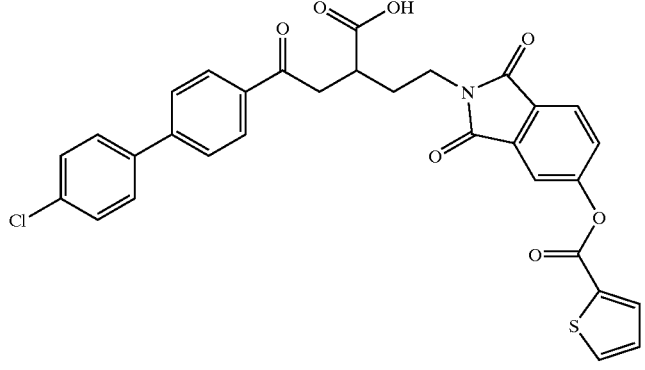 racemate |
| C-XXXIX | 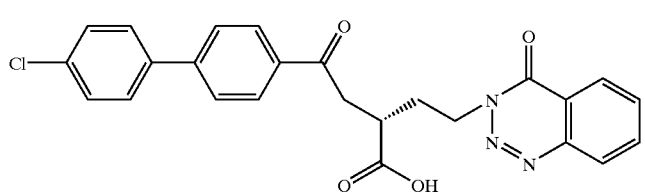 1S-enant. to C-XXXVI |

In the above structures, the term "racemate" in case of the cyclopentane derivatives refers to the trans, trans-diastereomer, that is, e.g. for examples C-VII, C-XI, C-XVI to C-XVIII and C-XXIX to C-XXXV a 1S/R, 2S/R, 5R/S relationship.

Especially preferred is the use of the following compound:

(+)-4-(4'-chloro[1,1'-biphenyl]-4-yl)-2-[2-(1,3-dioxo-1,3-dihydro-2H-isoindol-2-yl)ethyl]-4-oxobutanoic acid

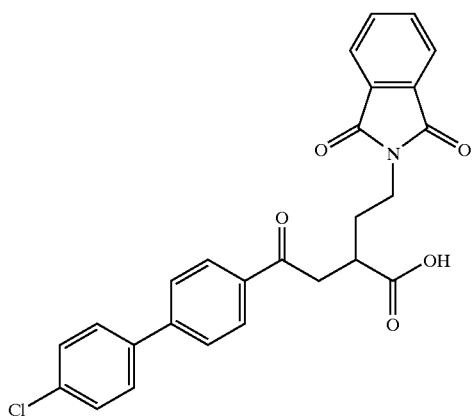

In another aspect of the invention the following new compounds of the general formula (I')

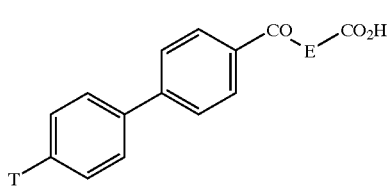

are provided, wherein CO—E—CO$_2$H represents a 3-carboxyl-5-R$^7$-pentan-1-on-1-yl-residue and the substituents T and R$^7$ have the meaning indicated in the following table:

TABLE 2

| T | R$^1$ | racemate, (+)- or (−)-entantiomer |
|---|---|---|
| OEt | [phthalimide] | (+) ; |
| OEt | [phthalimide] | (−) ; |
| OAc | [phthalimide] | rac ; |
| OH | [phthalimide] | rac ; |

TABLE 2-continued

| T | R$^1$ | racemate, (+)- or (−)-entantiomer |
|---|---|---|
| Cl | [4,6-dimethoxy-N-methylphthalimide] | rac ; |
| Br | [N-methylphthalimide] | (+) ; |
| Br | [N-methylphthalimide] | (−) ; |
| Cl | [methylenedioxy-N-methylphthalimide] | (+) ; |
| Cl | [methylenedioxy-N-methylphthalimide] | (−) ; |
| CN | [3-methyl-benzo[d][1,2,3]triazin-4(3H)-one] | rac or |
| OCF$_3$ | [3-methyl-benzo[d][1,2,3]triazin-4(3H)-one] | rac . |

Especially preferred is the following compound:
(+)-2-[2-(1,3-dioxo-1,3-dihydro-2H-isoindol-2-yl)ethyl-4-(4'-ethoxy[1,1'-biphenyl]-4-yl)-4-oxobutanic acid

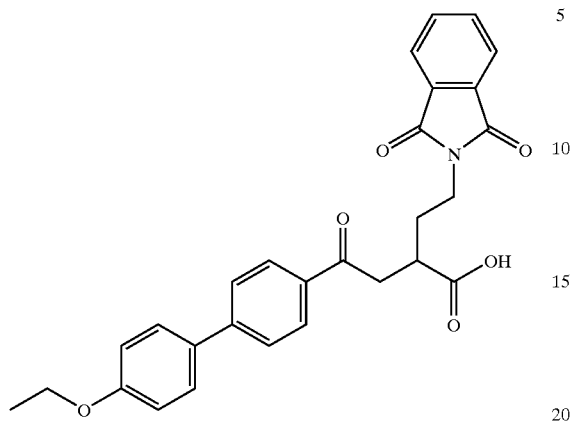

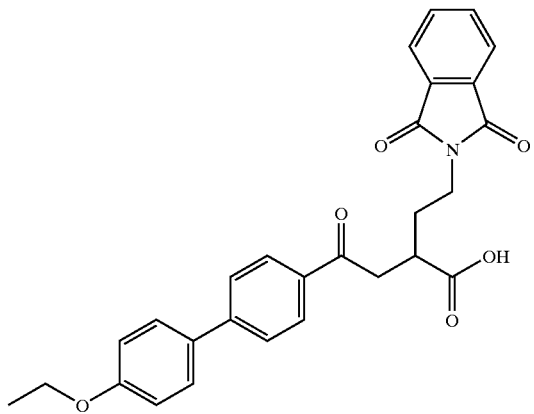

In another aspect of the invention, use of compounds of the general formula (I')

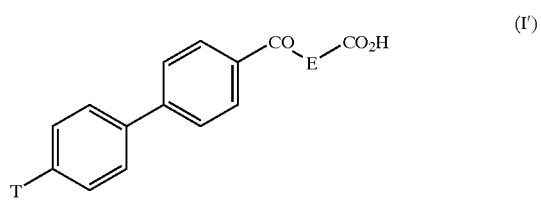

(I')

wherein

T is ($C_1$–$C_4$)-alkoxy, chloride, bromide, fluoride, acetoxy, hydroxy, cyano, trifluoromethyl or trifluoromethoxy, CO—E—$CO_2H$ represents a 3-carboxyl-5-$R^7$-pentan-1-on-1-yl- or a 2-carboxyl-3-($R^7$-methyl)-cyclopentan-1-yl)carbonyl-residue, and $R^7$ represents a group of the formula

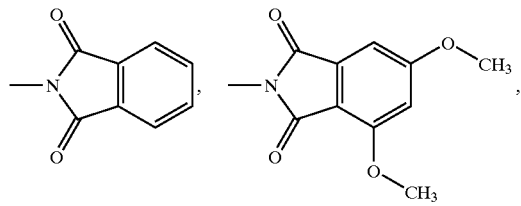

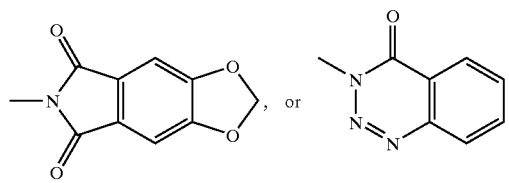

and their salts, is a preferred embodiment.

Especially preferred is the use of the following compound:
(+)-2-[2-(1,3-dioxo-1,3-dihydro-2H-isoindol-2-yl)ethyl]-4-(4'-ethoxy[1,1'-biphenyl]-4-yl)-4-oxobutanoic acid, General Preparative Methods:

The compounds of the invention may be prepared by use of known chemical reactions and procedures as described in details in WO 96/15096, WO 97/43237, WO 97/43238, WO 97/43239, WO 97/43240, WO 97/43245, WO97/43247 and WO 98/22436. Nevertheless, the following general preparative methods are presented to aid the reader in synthesizing the inhibitors. General methods A through K may be used to prepare appropriately substituted 4-biaryl-4-oxobutanoic acids, 4-aryl-4-oxobutanoic acids, 5-biaryl-5-oxopentanoic acids, or 5-aryl-5-oxopentanoic acids. These general methods are also found in WO 9615096 (23 May, 1996) along with exemplary preparations of the keto acids. The choice of a specific synthetic method is dictated by the proviso that the conditions used do not effect undesired changes in the T or $R^6$ moieties of the compounds prepared.

All variable groups of these methods are as described in the generic description if they are not specifically defined below. The variable subscript n is independently defined for each method. When a variable group with a given symbol (i.e. $R^6$ or T) is used more than once in a given structure, it is to be understood that each of these groups may be independently varied within the range of definitions for that symbol. As defined above, the compounds of the invention contain as the E unit a chain of 2 or 3 carbon atoms bearing 1 to 3 substituents $R^6$ which are not defined as H. By contrast, it is to be noted that in the general method schemes below, the $R^6$ groups are used as if their definition includes H, to show where such $R^6$ groups may exist in the structures, and for ease in drawing. No change in the definition of $R^6$ is intended by this non-standard usage, however. Thus, only for purposes of the general method schemes below, $R^6$ may be H in addition to the moieties set forth in the definition of $R^6$. The ultimate compounds contain 1 to 3 non-hydrogen groups $R^6$.

General Method A—The key intermediates in which the rings A and B are substituted phenyl and phenylene respectively are conveniently prepared by use of a Friedel-Crafts reaction of a substituted biphenyl II with an activated acyl-containing intermediate such as the succinic or glutaric anhydride derivative III or acid chloride IV in the presence of a Lewis acid catalyst such as aluminum trichloride in an aprotic solvent such as 1,1,2,2-tetrachloroethane. The well known Friedel-Crafts reaction can be carried out with many alternative solvents and acid catalysts as described by E. Berliner, *Org. React.*, 5, 229 (1949) and H. Heaney, *Comp. Org. Synth.*, 2, 733 (1991).

Method A

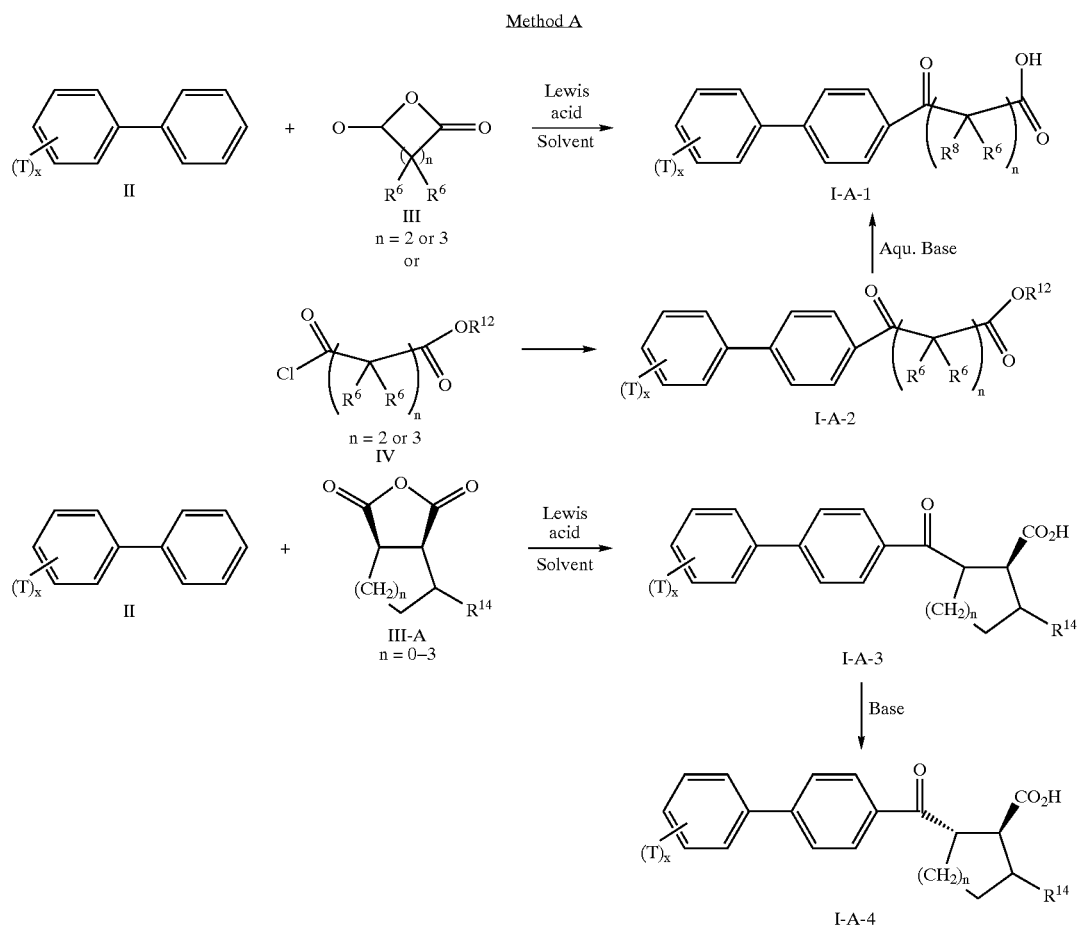

If the anhydride III is monosubstituted or multiplesubstituted in an unsymmetrical way, the raw product I-A often exists as a mixture of isomers via attack of the anhydride from either of the two carbonyls. The resultant isomers can be separated into pure forms by crystallization or chromatography using standard methods known to those skilled in the art.

When they are not commercially available, the succinic anhydrides III can be prepared via a Stobbe Condensation of a dialkyl succinate with an aldehyde or ketone (resulting in side chain $R^6$), followed by catalytic hydrogenation, hydrolysis of a hemiester intermediate to a diacid and then conversion to the anhydride III by reaction with acetyl chloride or acetic anhydride. Alternatively, the hemiester intermediate is converted by treatment with thionyl chloride or oxalyl chloride to the acid chloride IV in which $R^{12}$ is lower alkyl. For a review of the Stobbe condensation, including lists of suitable solvents and bases see W. S. Johnson and G. H. Daub, *Org. React.*, 6, 1 (1951). This method, as applied to the preparation of III ($R^6$=H, isobutyl and H, n-pentyl), has been described by D. Wolanin, et al., U.S. Pat. No. 4,771,038, Sep. 13, 1988.

Method A is especially useful for the preparation of cyclic key intermediates such as I-A-3 in which two $R^6$ groups are connected in a methylene chain to form a 4–7 membered ring. Small ring (3–5 member) anhydrides are readily available only as cis isomers which yield cis invention compounds I-A-3. The trans compounds I-A-4 are then prepared by treatment of I-A-3 with a base such as DBU in THF.

The substituted four member ring starting material anhydrides such as III-A-1 are formed in a photochemical 2+2 reaction as shown below. This method is especially useful for the preparation of compounds in which $R^{14}$ is acetoxy or acetoxy-methylene. After the subsequent Friedel-Crafts reaction the acetate can be removed by basic hydrolysis and the carboxyl protected by conversion to 2-(tri-methylsilyl) ethyl ester. The resultant intermediate with $R^{14}$=CH$_2$OH can be converted to key intermediates with other $R^{14}$ groups by using procedures described in General Method K.

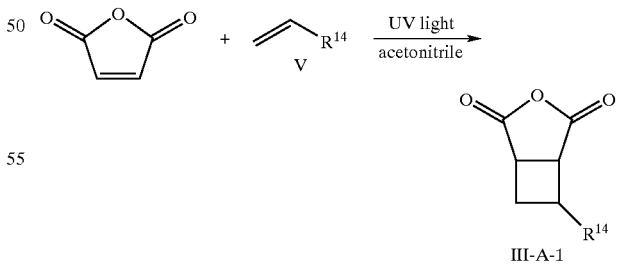

The Friedel Crafts method is also useful when double bonds are found either between C-2 and C-3 of a succinoyl chain (from maleic anhydride or 1-cyclopentene-1,2-dicarboxylic anhydride, for example) or when a double bond is found in a side chain, such as in the use of itaconic anhydride as starting material to yield products in which two $R^6$ groups as found on one chain carbon together form an exo-methylene (=CH$_2$) group. Subsequent uses of these compounds are described in Methods D and E.

General Method B—Alternatively key intermediates can be prepared via a reaction sequence involving monoalkylation of a dialkyl malonate VI with an alkyl halide to form intermediate VII, followed by alkylation with a halomethyl biphenyl ketone VIII to yield intermediate IX. Compounds of structure IX are then hydrolyzed with aqueous base and then heated to decarboxylate the malonic acid intermediate and yield I-B-2 (Method B-1). By using one equivalent of aqueous base the esters I-B-2 with $R^{12}$ as alkyl are obtained, and using more than two equivalents of base the acid compounds ($R^{12}$=H) are obtained. Optionally, heat is not used and the diacid or acid-ester I-B-1 is obtained.

Intermediates VIII are formed from biphenyls II in a Friedel-Craft reaction with haloacetyl halides such as bromoacetyl bromide or chloroacetyl chloride. Alternatively, the biphenyl can be reacted with acetyl chloride or acetic anhydride and the resultant product halogenated with, for example, bromine to yield intermediates VIII (X=Br).

Method B has the advantage of yielding single regio isomers whereas Method A yields mixtures. Method B is especially useful when the side chains $R^6$ contain aromatic or heteroaromatic rings that may participate in intramolecular acylation reactions to give side products if Method A were to be used. This method is also very useful when the $R^6$ group adjacent to the carboxyl of the final compound contains heteroatoms such as oxygen, sulfur, or nitrogen, or more complex functions such as imide rings.

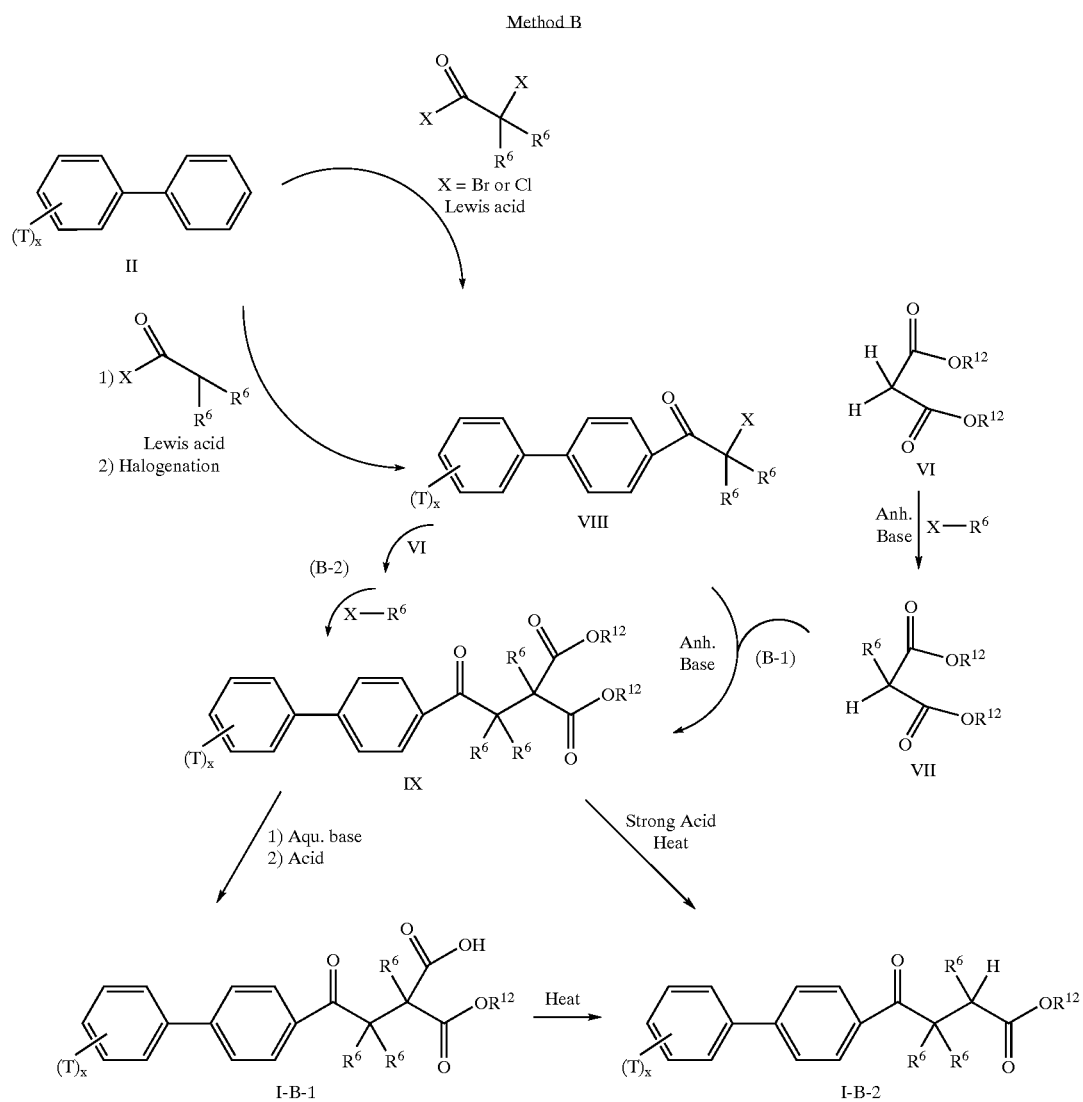

Method B

Alternatively, the diester intermediate IX can be heated with a strong acid such as concentrated hydrochloric acid in acetic acid in a sealed tube at about 110° C. for about 24 hr to yield I-B-2 ($R^{12}$=H).

Alternatively, the reaction of VI with VIII can be conducted before that with the alkyl halide to yield the same IX (Method B-2).

General Method C—Especially useful is the use of chiral HPLC to separate the enantiomers of racemic key intermediate mixtures (see, for example, D. Arlt, B. Boemer, R Grosser and W. Lange, Angew. Chem. Int. Ed. Engl. 30 (1991) No. 12). The key intermediates are prepared as pure enantiomers by use of a chiral auxiliary route—see, for example: D. A. Evans, Aldrichimica Acta, 15(2), 23 (1982) and other similar references known to one skilled in the art.

C-1. Acid halide X is reacted with the lithium salt of chiral auxiliary XI (R is often isopropyl or benzyl) to yield intermediate XII, which in turn is alkylated at low temperatures (typically under −50° C.) with halo-tert-butylacetyl compound XIII to yield pure isomer XIV. The use of opposite chirality XI yields opposite chirality XIV. Conversion of XIV to the enantiomerically pure diacid XV is accomplished by treatment with lithium hydroxide/hydrogen peroxide in THF/water, followed by acids such as trifluoroacetic acid. The compound XV is then converted to enantiomerically pure anhydride III-A by treatment with acetyl chloride. The use of a Friedel-Crafts reaction as in method A then converts III-A to I-C-1.

C-2. Biphenyl starling material II may also first be reacted in a Friedel-Crafts reaction as earlier described with succinic anhydride followed by Fisher esterification with a lower alcohol such as methanol in the presence of a strong acid such as sulfuric acid to form acyl derivative I-C-2. The carbonyl group of this material is then blocked as a ketal such as that formed by treatment with 1,2-bistrimethyl-silyloxyethane in the presence of a catalyst such as trimethyl-silyltriflate in a suitable solvent. Many other ketal derivatives and reaction conditions familiar to those skilled in the art can also be used in this step. Basic hydrolysis of the ester followed by reaction of the resultant I-C-3 with XI in the presence of an amide coupling agent such as 1-(3-dimethylaminopropyl)-3-ethylcarbodiimide yields amide I-C-4. Reaction of this chiral amide with an alkylating agent such as alkyl or arylalkyl triflate or halide yields enantiomerically enriched product I-C-5 which can be converted to ketal acid I-C-6 by treatment with a weak base such as lithium hydroxide/hydrogen peroxide and then to keto acid I-C-7 by treatment with an acid. These deblocking steps can be conducted in either order.

Method C-1

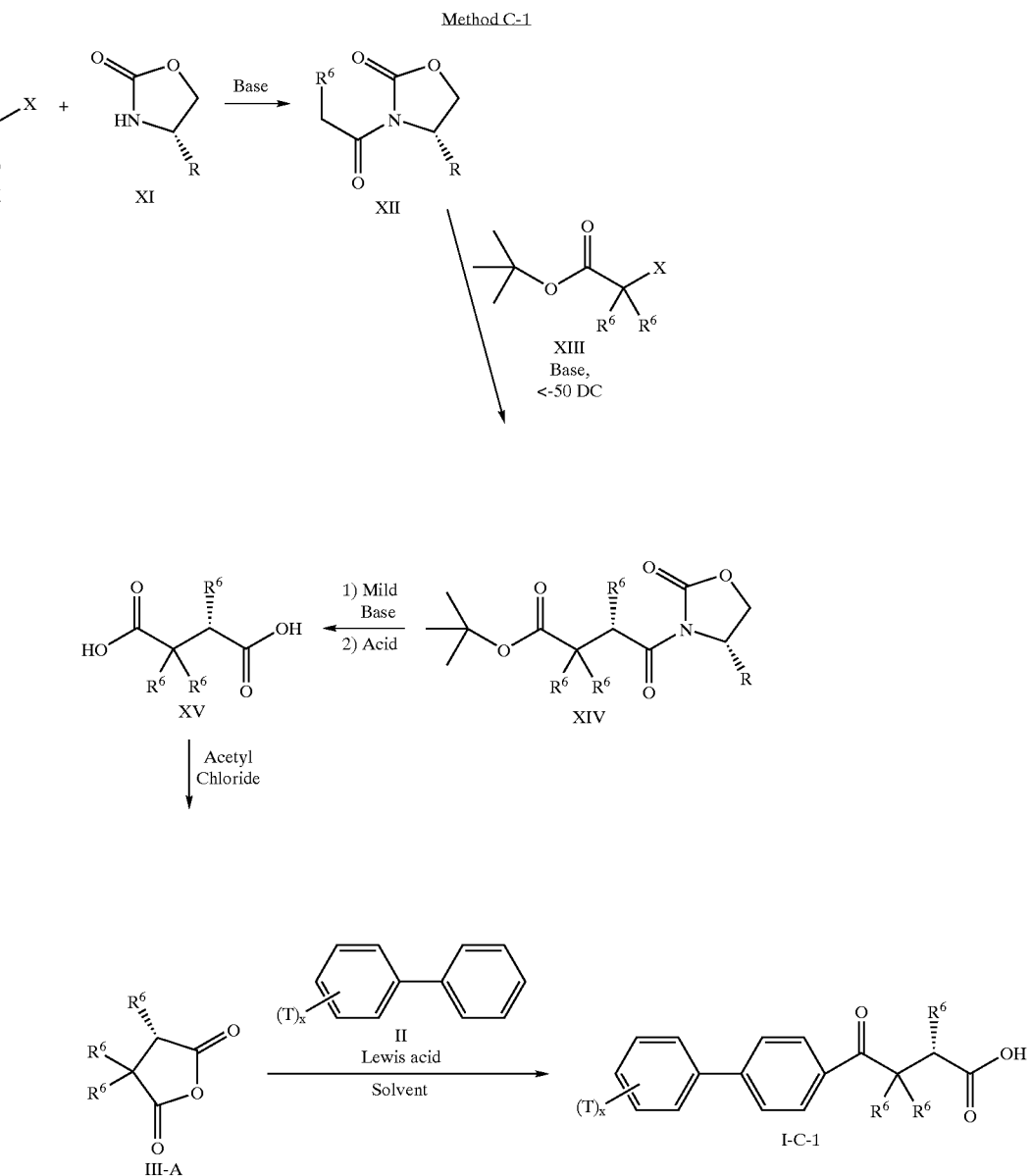

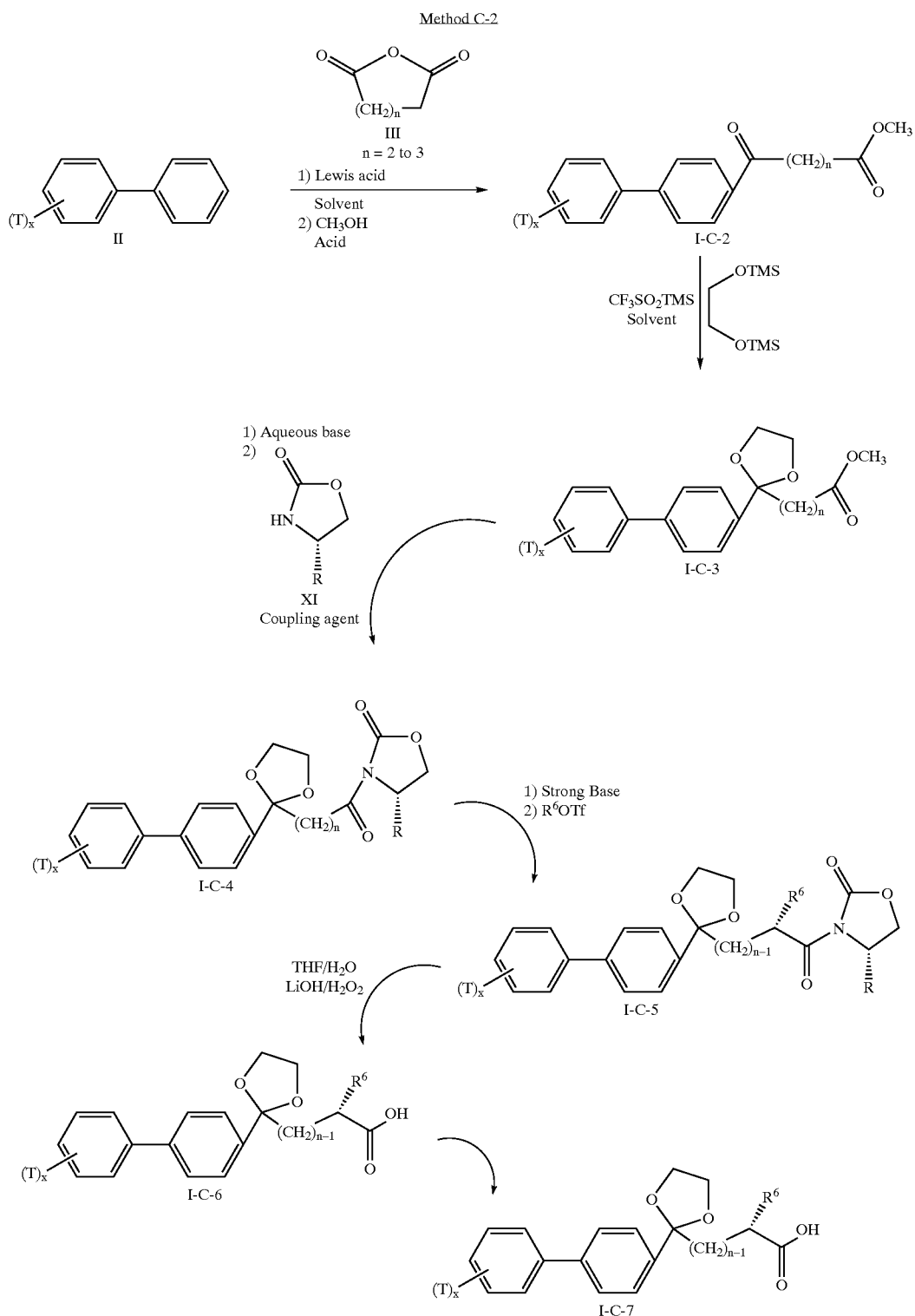

Method C-2

General Method D—Key intermediates in which $R^6$ are alkyl- or aryl- or heteroaryl- or acyl- or heteroarylcarbonyl-thiomethylene are prepared by methods analogous to those described in the patent publication WO 90/05719. Thus substituted itaconic anhydride XVI (n=1) is reacted under Friedel-Crafts conditions to yield acid I-D-1 which can be separated by chromatography or crystallization from small amounts of isomeric I-D-5. Alternatively, I-D-5 are obtained by reaction of key intermediates I-D-4 (from any of Methods A through C) with formaldehyde in the presence of a base.

Compounds I-D-1 or I-D-5 are then reacted with a mercapto derivative XVII or XVIII in the presence of a catalyst such as potassium carbonate, ethyldiiso-butylamine, tetrabutylammonium fluoride or free radical initiators such as azobisisobutyronitrile (AIBN) in a solvent such as dimethylformamide or tetrahydrofurane to yield key intermediates I-D-2, I-D-3, I-D-6 or I-D-7.

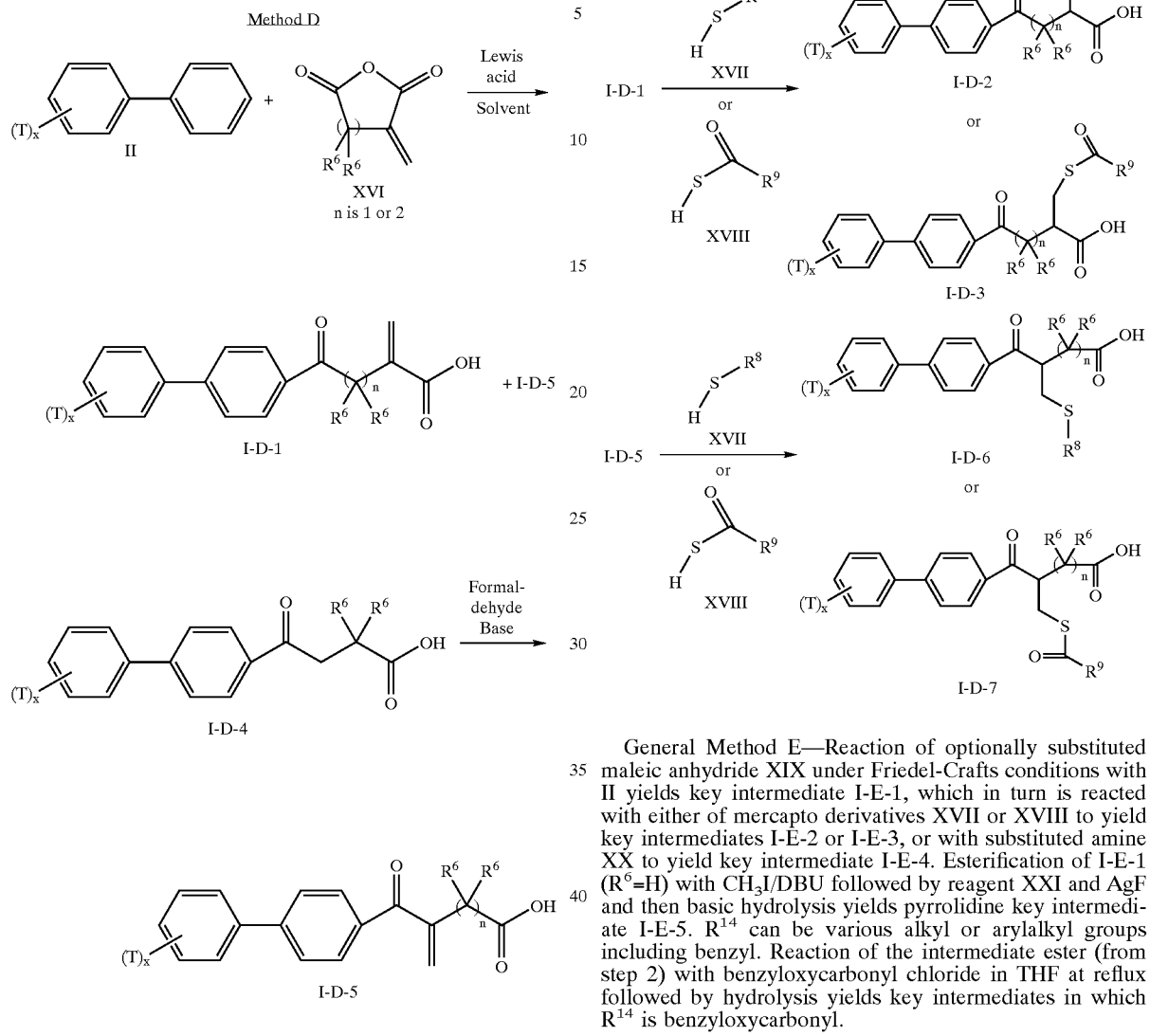

General Method E—Reaction of optionally substituted maleic anhydride XIX under Friedel-Crafts conditions with II yields key intermediate I-E-1, which in turn is reacted with either of mercapto derivatives XVII or XVIII to yield key intermediates I-E-2 or I-E-3, or with substituted amine XX to yield key intermediate I-E-4. Esterification of I-E-1 ($R^6$=H) with $CH_3I$/DBU followed by reagent XXI and AgF and then basic hydrolysis yields pyrrolidine key intermediate I-E-5. $R^{14}$ can be various alkyl or arylalkyl groups including benzyl. Reaction of the intermediate ester (from step 2) with benzyloxycarbonyl chloride in THF at reflux followed by hydrolysis yields key intermediates in which $R^{14}$ is benzyloxycarbonyl.

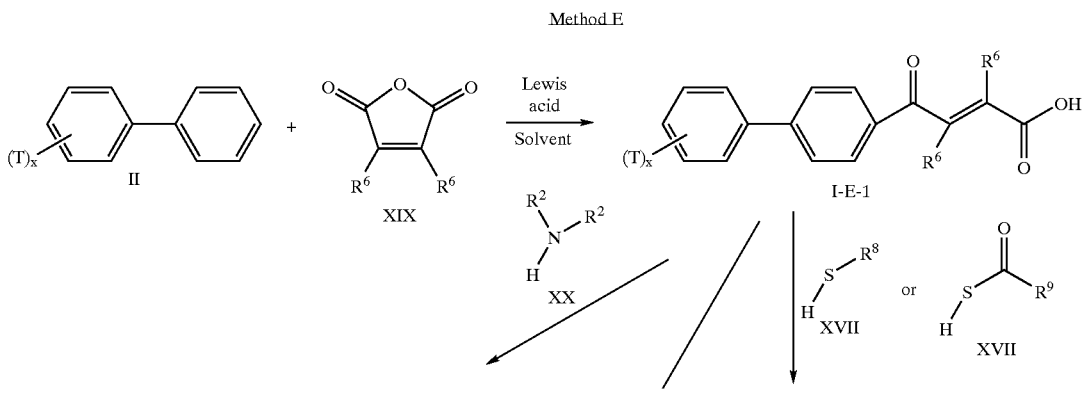

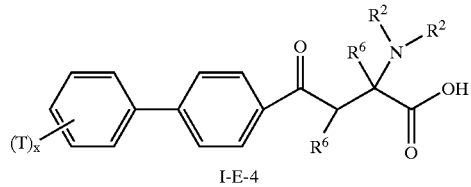

I-E-4

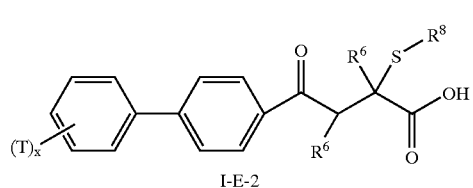

I-E-2

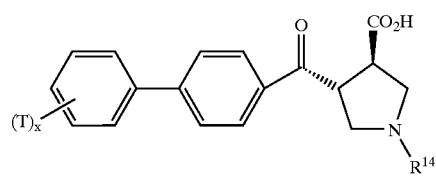

I-E-5

1) CH₃I, DBU
2) TMS-CH₂-N(R¹⁴)-CH₂-CN  AgF
   XXI
3) NaOH

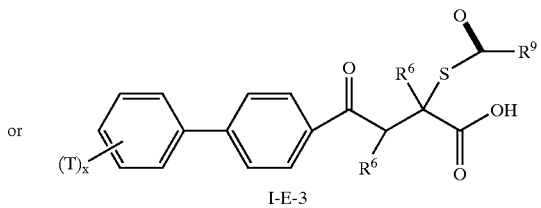

or

I-E-3

General Method F—Biaryl key intermediates such as those of this application may also be prepared by Suzuki or Stille cross-coupling reactions of aryl or heteroaryl metallic compounds in which the metal is zinc, tin, magnesium, lithium, boron, silicon, copper, cadmium or the like with an aryl or heteroaryl halide or triflate (trifluoromethane-sulfonate) or the like. In the equation below either Met or X is the metal and the other is the halide or triflate. Pd(com) is a soluble complex of palladium such as tetrakis(triphenylphosphine)-palladium(0) or bistriphenylphosphine)palladium(II) chloride. These methods are well known to those skilled in the art. See, for example, A. Suzuki, Pure Appl. Chem., 66, 213–222 (1994); A. Suzuki, Pure Appl. Chem., 63, 419–422 (1991); and V. Farina and G. Roth, "Metal-Organic Chemistry" Volume 5 (Chapter 1), 1994.

The starting materials XXIII (B=1,4-phenylene) are readily formed using methods analogous to those of methods A, B or C but using a halobenzene rather than a biphenyl as starting material. When desired, the materials in which X is halo can be converted to those in which X is metal by reactions well known to those skilled in the art such as treatment of a bromo intermediate with hexamethylditin and palladium tetrakistriphenylphosphine in toluene at reflux to yield the trimethyltin intermediate. The starting materials XXIII (B=heteroaryl) are most conveniently prepared by method C but using readily available heteroaryl rather than biphenyl starting materials. The intermediates XXII are either commercial or easily prepared from commercial materials by methods well known to those skilled in the art.

These general methods are useful for the preparation of key intermediates for which Friedel-Crafts reactions such as those of Methods A, B, C, D or E would lead to mixtures with various biaryl acylation patterns. Method F is also especially useful for the preparation of key intermediates in which the aryl groups A or B contain one or more heteroatoms (heteroaryls) such as those compounds that contain thiophene, furan, pyridine, pyrrole, oxazole, thiazole, pyrimidine or pyrazine rings or the like instead of phenyls.

Method F

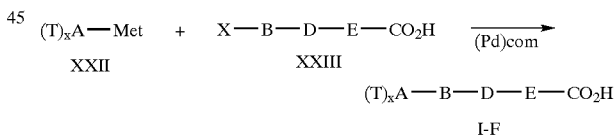

T, x, A, B, E and D as in Structure I

Met=Metal and X=Halide or Triflate or

Met=Halide or Triflate and X=Metal

General Method G—When the $R^6$ groups of method F form together a 4–7 membered carbocyclic ring as in Intermediate XXV below, the double bond can be moved out of conjugation with the ketone group by treatment with two equivalents of a strong base such as lithium diisopropylamide or lithium hexamethylsilylamide or the like followed by acid quench to yield compounds with the structure XXVI. Reaction of XXVI with mercapto derivatives using methods analogous to those of General Method D then leads to key intermediate I-G-1 or I-G-2.

Method G

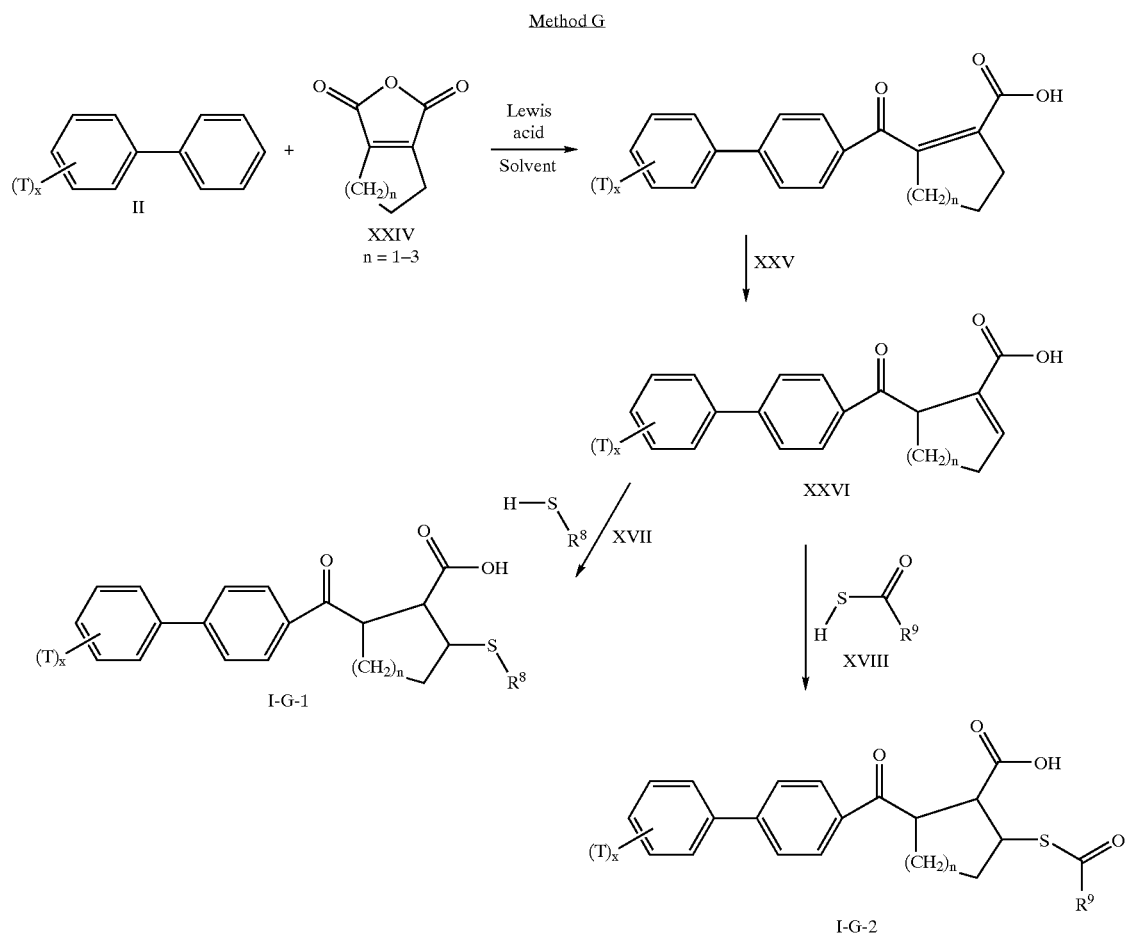

General Method H—Key intermediates in which two $R^6$ groups form a 4–7 member carbocyclic ring as in I-H below and $R^{14}$ is alkyl or arylalkyl are prepared according to method H. Starting material XXVII is reacted with two equivalents of a strong base such as lithium diisopropylamide (LDA) followed by an alkyl or arylalkyl halide ($R^{14}X$) to yield intermediate XXVIII. This material is then reduced to the alcohol with a reducing agent capable of selective reduction of the ketone such as sodium borohydride, followed by dehydration with triphenylphosphine/diethyl azodicarboxylate (DEAD) in a suitable solvent such as THF at reflux to yield XXIX. Hydrolysis of the ester with aqueous base followed by amide formation with $R^{12}ONHR^{12}$ is ($C_1$–$C_4$)-alkyl, but usually $CH_3$) in the presence of a coupling agent such as dicyclohexyldiimide (DCC) yields XXX. Other acyl activating groups well known to those skilled in the art such as acid chlorides or mixed anhydrides could be used instead of XXX. Substituted biphenyl halide XXXI is reacted with an alkyl lithium such as two equivalents of t-butyl lithium to yield lithiated biphenyl XXXII which is then reacted with activated acyl compound XXX. The resultant intermediate XXXIII is then treated with diethylaluminum cyanide to yield intermediate XXXIV which is then hydrolyzed with aqueous acid to yield key intermediate I-H which is purified by chromatography on silica gel to afford pure isomers.

Method H

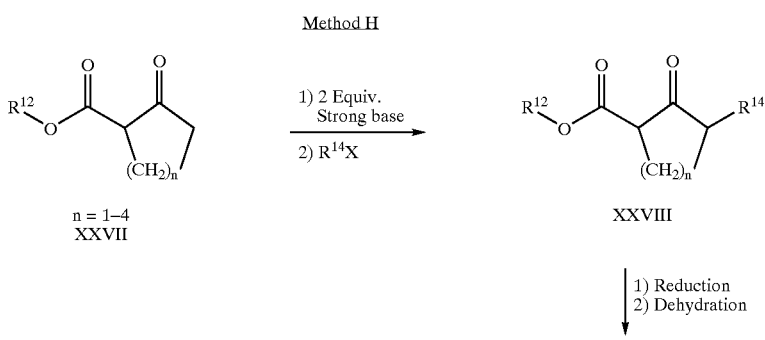

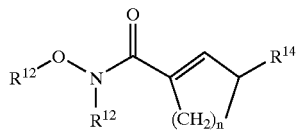

XXX

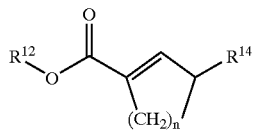

XXIX

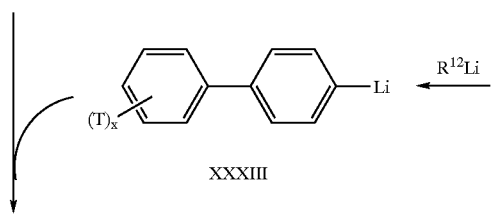

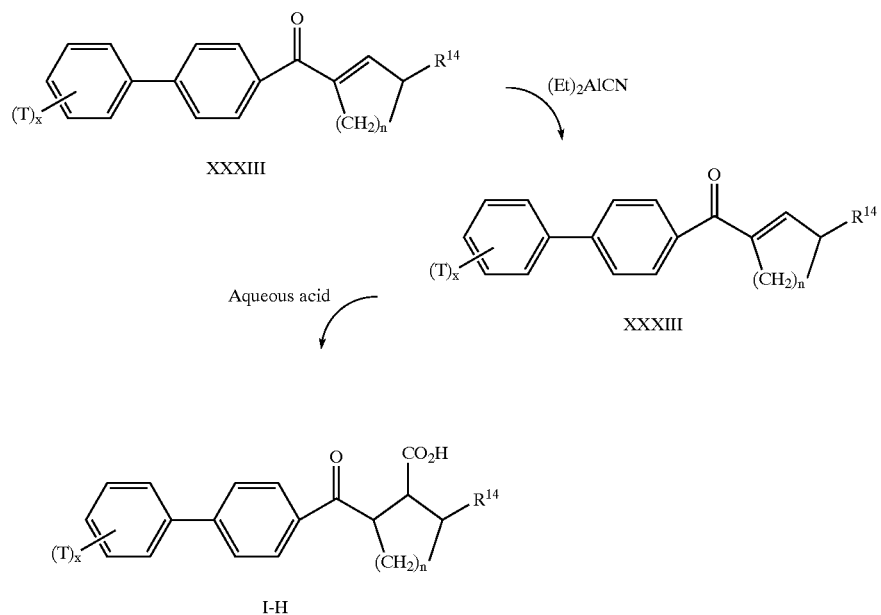

General Method I—Key intermediates in which two R6 groups together form a pyrrolidine ring are prepared according to method I. Starting material XXXV (L-pyroglutaminol) is reacted under acid catalysis with benzaldehyde XXXVI (may be substituted) to yield bicyclic derivative XXXVII. A double bond is then introduced using phenylselenenyl methodology well known to those skilled in the art to yield XXXVIII, which, in turn, is reacted with a vinylcopper (I) complex to yield conjugate addition product XXXIX. Such reactions in which Lig can be, for example, another equivalent of vinyl group or halide are well known to those skilled in the art. Hydride reduction (lithium aluminum hydride or the like) of XXXIX followed by standard blocking with, for example, t-butyldimethylsilylchloride yields XXXX which in turn is reacted with an optionally substituted benzylchloroformate XXXXI to yield XXXXII. Ozonolysis of this intermediate followed by reductive workup (dimethylsulfide, zinc/acetic acid or the like) leads to aldehyde XXXXIII. Reaction of this aldehyde with a biphenyl organometallic such as XXXII yields alcohol XXXXIV. Deblocking of the silyl group with, for example, tetrabutylammonium fluoride followed by oxidation with, for example, pyridiniumdichromate or the like yields key intermediate 1-I-1 in which $R^{14}$ is a carbobenzyloxy group.

Alternatively the carbobenzyloxy group is removed by reaction with hydrogen and a catalyst such as palladium on carbon to yield the unsubstituted key intermediate 1-I-2 optionally followed by N-alkylation to yield key intermediate 1-I-3. These final steps are well known to those skilled in the art. Alternatively the intermediate XXXX can be directly treated with ozone followed by the other steps of this method to yield 1-I-3, in which $R^{14}$ is optionally substituted benzyl rather than as in 1-I-1.

This method is especially useful to prepare single enantiomers because starting material XXXV is available as either the isomer as drawn or as D-pyroglutaminol to yield enantiomeric products.

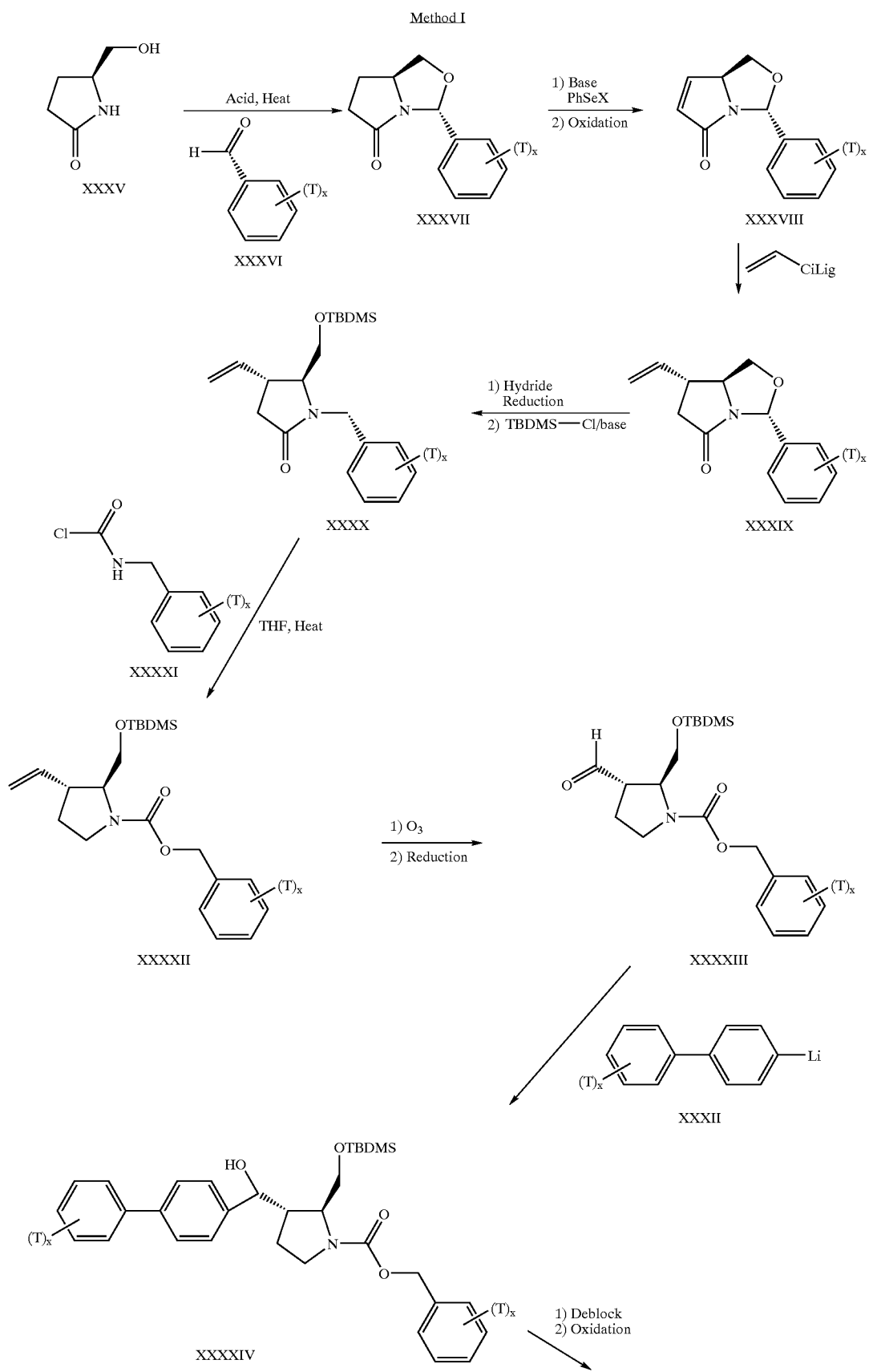

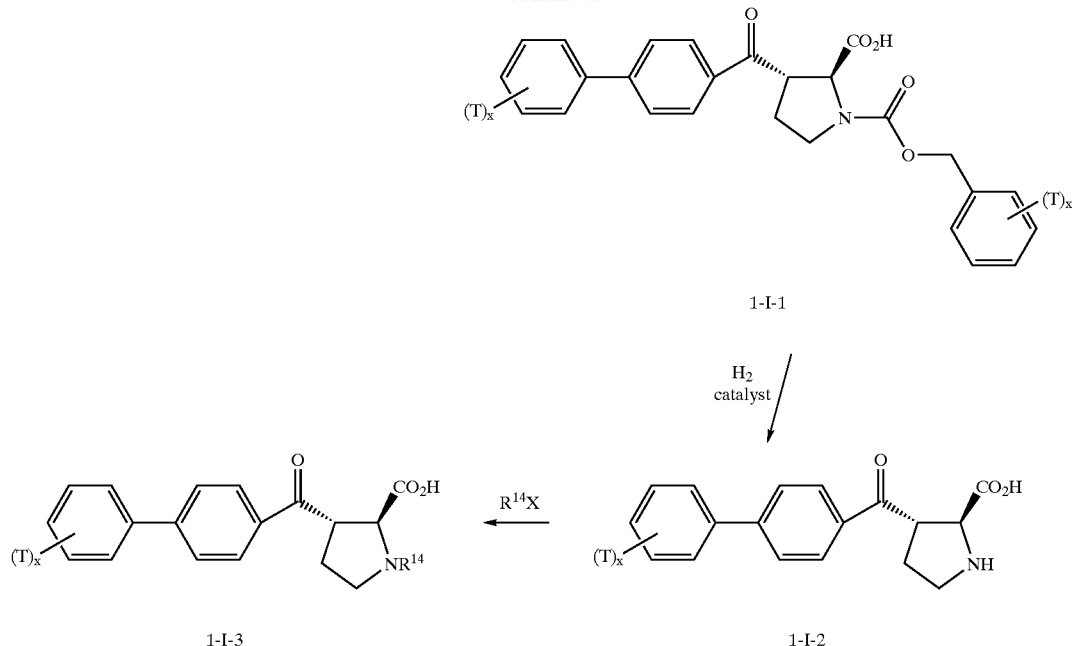

General Method J—The key intermediates in which E represents a substituted chain of 3 carbons are prepared by method J. Intermediates XXXXVII, if not available from commercial sources, are prepared by reaction of an activated biphenylcarboxylic acid derivative XXXXV with substituted acetic acid XXXXVI which has been converted to its bis-anion with two equivalents of a strong base such as LDA followed by heating to decarboxylate the intermediate keto acid. Product XXXXVII is then treated with methylenemalonate derivative XXXXVIII in the presence of a strong base such as sodium hydride to yield substituted malonate XXXXIX. This malonate can be further alkylated under conditions familiar to those skilled in the art to yield L which in turn is treated with acid and then heated to yield key intermediate 1-J-1, Alternatively the final alkylation can be omitted to yield products in which the $R^6$ adjacent to the carboxyl is H. Alternatively XXXXVII can be alkylated with 3-halopropionate ester LI in the presence of base such as LDA to yield ester 1-J-2 which can then be hydrolyzed with aqueous base to yield key intermediate 1-J-3 upon treatment with acid. This method is especially useful if any of the groups $R^6$ contain aromatic residues.

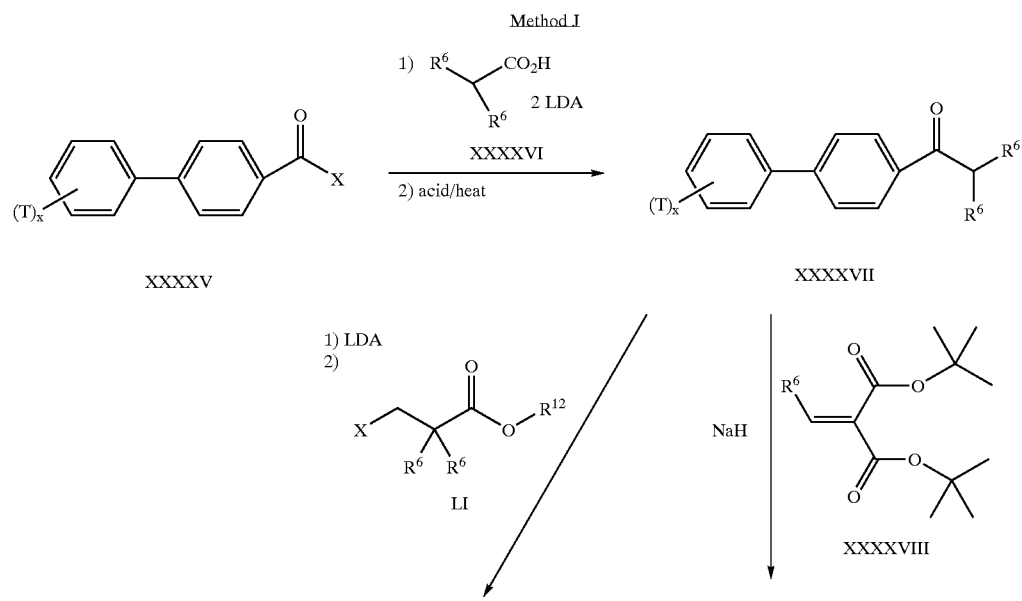

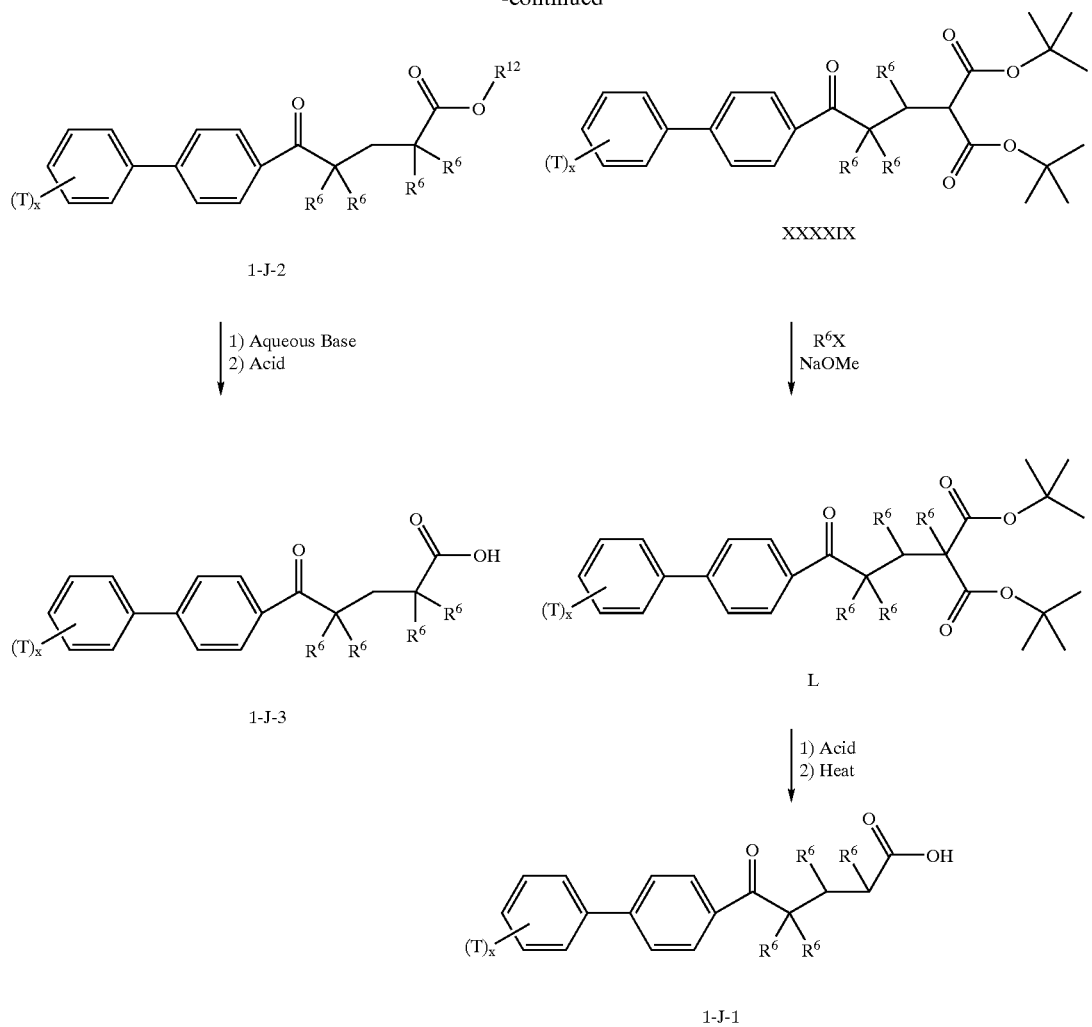

Method K—The key intermediates in which two $R^6$ groups are joined to form a substituted 5-member ring are most conveniently prepared by method K. In this method acid LII (R=H) is prepared using the protocols described in *Tetrahedron*, Vol. 37, Suppl., 1981, 411. The acid is protected as an ester (R=benzyl or 2-(trimethylsilyl)ethyl) by use of coupling agents such as 1-(3-dimethylaminopropyl)-3-ethylcarbodiimide hydrochloride and procedures well known to those skilled in the art. Substituted bromobiphenyl LIII is converted to its Grignard reagent by treatment with magnesium which is then reacted with LII to yield alcohol LIV. Alcohol LIV is eliminated via base treatment of its mesylate by using conditions well known to those skilled in the art to yield olefin LV. Alternatively LIII is converted to a trimethyltin intermediate via initial metallation of the bromide with n-butyllithium at low temperature (−78° C.) followed by treatment with chlorotrimethyltin and LII is converted to an enoltriflate by reaction with 2-[N,N-bis(trifluoromethylsulfonyl)-amino]-5-chloropyridine in the presence of a strong aprotic base. The tin and enoltriflate intermediates are then coupled in the presence of a $Pd°$ catalyst, CuI and $AsPh_3$ to yield directly intermediate LV. Ozonolysis of LV (workup with methyl sulfide) yields aldehyde LVI. Alternatively treatment with $OsO_4$ followed by $HIO_4$ converts LV to LVI.

Conversion of intermediate LVI to key intermediate I-K is accomplished in several ways depending on the identity of side chain function X. Reaction of LVI with Wittig reagents followed by hydrogenation yields products in which X is alkyl, aryl or arylalkyl. Reduction of aldehyde LVI with LAH yields alcohol I-K (X=OH). The alcohol is converted to phenyl ethers or N-phthalimidoyl compounds by use of the appropriate starting materials and Mitsunobu conditions well known to those skilled in the art; see O. Mitsunobu, Synthesis, 1 (1981). Alternatively the alcohol of I-K (X=OH) is converted to a leaving group such as tosylate (X=OTs) or bromide (X=Br) by conditions well known to those skilled in the art and then the leaving group is displaced by sulfur or azide nucleophiles to yield products with X=thioether or azide which in turn is reduced and acylated to yield amides (X=NHAcyl). Direct acylation of the alcohol I-K (X=OH) yields key intermediates in which X=OAcyl and reaction of the alcohol with various alkyl halides in the presence of base yields alkyl ethers (X=$OR^2$). In each case a final step is removal of acid blocking group R to yield acids (R=H) by using conditions which depend on the stability of R and X, but in all cases well known to those skilled in the art such as removal of benzyl by base hydrolysis or of 2-(trimethylsilyl)ethyl by treatment with tetrabutylammonium fluoride.

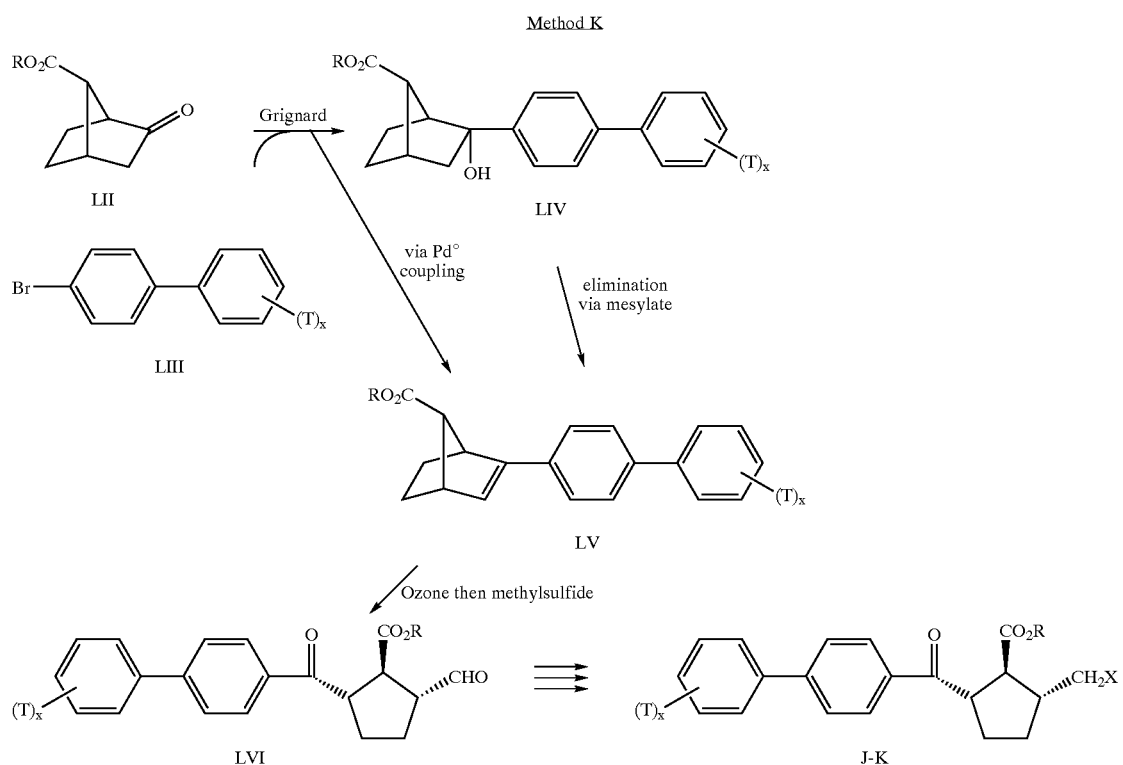

Method K

Suitable pharmaceutically acceptable salts of the compounds of the present invention that contain an acidic moiety include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethyl-piperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

Suitable pharmaceutically acceptable salts of the compounds of the present invention that contain a basic moiety include addition salts formed with organic or inorganic acids. The salt forming ion derived from such acids can be halide ions or ions of natural or unnatural carboxylic or sulfonic acids, of which a number are known for this purpose. Examples include chlorides, acetates, tartrates, or salts derived from amino acids like glycine or the like. The physiologically acceptable salts such as the chloride salts and the amino acid salts can be used medicinally as described below and are preferred.

These and other salts which are not necessarily physiologically acceptable are useful in isolating or purifying a product acceptable for the purposes described below.

The salts are produced by reacting the acid form of the invention compound with an equivalent of the base supplying the desired basic ion or the basic form of the invention compound with an equivalent of the acid supplying the desired acid ion in a medium in which the salt precipitates or in aqueous medium and then lyophilizing. The free acid or basic form of the invention compounds can be obtained from the salt by conventional neutralization techniques, e.g., with potassium bisulfate, hydrochloric acid, sodium hydroxide, sodium bicarbonate, etc.

The compounds of the present invention are expected to inhibit the matrix metalloproteases MMP-2, MMP-3, MMP-8, MMP-9, MMP-12, MMP-13, and the related protease TACE, as well as the release of TNFα in vivo, and are therefore expected to be useful for treating or preventing the conditions referred to in the background section. As other MMPs not listed above share a high degree of homology with those listed above, especially in the catalytic site, it is deemed that compounds of the invention should also inhibit such other MMPs to varying degrees.

Varying the substituents on the biaryl portions of the molecules, as well as those of the $R^6$ groups of the claimed compounds, is expected to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The compounds of the present invention exhibit good activity for MMP-2, MMP-3, MMP-8, MMP-9, MMP-12 and MMP-13, and a good selectivity for these MMP's over other MMP's such as MMP-1 and MMP-7.

As a result of the abovementioned selectivity profile, the compounds of the present invention are especially suitable for the treatment of respiratory diseases.

The method of treating matrix metalloprotease-mediated or TNFα release-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 $\mu$m) such as those comprising cellulose, polyacrylate or polycarbophil, in conjunction with suitable absorption enhancers such as phospholipids or acylcarnitines. Available systems include those developed by DanBiosys and Scios Nova.

Oral delivery may be achieved by incorporation of the drug into tablets, coated tablets, dragées, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azocrosslinked polymers that are degraded by colon specific bacterial azoreductasas, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art Alternatively, the requisite amount may be calculated, based on a determination of the amount of target enzyme which must be inhibited in order to treat the condition. It is expected that the compounds of the invention generally will be administered in doses in the range of 0.01–100 mg per kg of body weight per day.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

Biological Protocols

Inhibitory activities of the compounds of the invention against matrix metallo-proteases and production of TNFα may be determined as described below.

P218 Quenched Fluorescence Assay for MMP Inhibition:

This assay is adapted from the one described by Knight et al., FEBS Letters, 296, 263–266 (1992) for MMP-3 and a related substrate. The rate of hydrolysis of the synthetic substrate H-MCA-Pro-Lys-Pro-Leu-Ala-Leu-DPA-Ala-Arg-NH$_2$ (P218) by the respective MMPs is monitored fluorometrically, using an excitation wavelength of 340 nm and an emission wavelength of 395 nm, in the presence or absence of the test compounds. The substrate is made up initially in 100% DMSO to a concentration of $1 \times 10^{-2}$ M, then diluted in assay buffer to a final concentration of 20 $\mu$M. Test compounds (10 mM in DMSO) are diluted in assay buffer at an initial concentration of 0.3–1000 nM. These are diluted to a final concentration in the assay from 0.03 nM to 100 nM. The reaction is initiated by the addition of substrate at a final concentration of 20 $\mu$M. The total assay volume in a 96 well microtitre plate is 150 $\mu$l, Cleavage of the substrate between the Leu-Ala residues allows the fluorescence of the MCA group to be detected on a fluorometer (Cytofluor II) following excitation at 340 nm and emission at 395 nm. Change in fluorescence is continually monitored for a 40 min period.

The $K_i$'s are calculated using the method described by Williams and Morrison, Methods in Enzymology, 63, 437–467 (1979) to measure $K_{i\ apparent}$ for tight binding inhibitors, and is summarised as follows:

$$[I]_0/(1-v_i/v_0) = K_{i\ apparent} \times v_i/v_0 + [E]_0$$

$[I]_0$ and $[E]_0$ are inhibitor and enzyme concentrations, and $v_i/v_0$ are reaction velocities with/without inhibitor. $[I]_0$ is equal to $IC_{50}$ when $v_i$ is half $v_0$, so that:

$$IC_{50} = 0.5 \times [E]_0 + K_{i\ apparent}$$

$IC_{50}$'s are determined at each enzyme concentration using Xlfit software. $K_{i\ apparent}$ is then determined graphically from the plot of $IC_{50}$ versus MMP concentration, using the intercepts to estimate $K_{i\ apparent}$. Thus, intercept values at $IC_{50} = 0$ and $[E]_0 = 0$ are equal to $-2 \times K_{i\ apparent}$ and $K_{i\ apparent}$, respectively. $IC_{50}$ values are calculated using % inhibition values at each enzyme concentration, ensuring data is taken from the linear part of the reaction rate curves. The $K_i$ can then be calculated from the equation:

$$K_i = K_{i\ apparent}/(1+S)/K_m$$

where S=substrate concentration and $K_m$=dissociation constant.

The assay conditions are modified as follows for each of the MMPs used:

MMP-1 (Human Gingival Fibroblast Interstitial Collagenase)

Pro-MMP-1 was supplied by Jack Windsor [Windsor et al., *J. Biol. Chem.* 269 (42), 26201–26207 (1994)]. The pro enzyme was activated by incubating in 1:20 Trypsin/1 mM AEBSF for 10 min at 25° C.

$K_m$ value: 30 µM

Assay Buffer: The assay is carried out in buffer containing 50 mM HEPES, 10 mM $CaCl_2$, pH 7.0.

Enzyme concentrations for $IC_{50}$ determinations: 0.1 µg/ml

Enzyme concentrations for $K_i$ determinations: 0.1–0.8 µg/ml

MMP-2 (Gelatinase A)

Gelatinase A (MMP-2) is prepared using a vaccinia expression system according to the method of R. Fridman et al., *J. Biol. Chem.*, 267, 15398 (1992).

Assay Buffer; The assay is carried out in buffer containing 50 mM Tris, 150 mM NaCl, 10 mM $CaC_2$, 0.005% Brij-35 at pH 7.0.

Enzyme concentrations for $IC_{50}$ determinations: 0.078 µg/ml

MMP-3 (Stromelysin)

Preparation of Recombinant Truncated Pro-stromelysin (MMP-3):

Truncated Pro-stromelysin-257 is expressed in a soluble form in *E. coli* as described by Marcy et al., Biochemistry, 30, 6476–6483, 1991 (see also Cancer Treat. Res. 61, 21–41 (1992)). Soluble truncated prostromelysin is purified by a modification of the monoclonal antibody affinity chromatography method described by Housley et al., J. Biol. Chem., 268, 4481–87, 1993.

Assay Buffer: The assay is carried out in buffer containing 50 mM HEPES, 10 mM $CaCl_2$, pH 7.0.

Enzyme concentrations for $IC_{50}$ determinations; 0.8 µg/ml

MMP-7 (Matrilysin)

Catalytic domain expressed in *E. coli* using the pET 14 vector, provided by Dr Steve Shapiro, Jewish Hospital at the Washington University Medical Center, St. Louis, Mo., USA.

Assay Buffer: The assay is carried out in buffer containing 50 mM HEPES, 10 mM $CaCl_2$, pH 7.0.

Enzyme concentrations for $IC_{50}$ determinations: 0.3 µg/ml

MMP-8 (Neutrophil Collagenase)

Active recombinant truncated form ($met^{80}$-$gly^{242}$) was obtained according to the protocol of Knauper, Eur. J. Biochem. 189, 296–300 (1990).

Assay Buffer: The assay is carried out in buffer containing 50 mM HEPES, 10 mM $CaCl_2$, pH 7.0.

Enzyme concentrations for $IC_{50}$ determinations: 9.4 µg/ml.

MMP-9 (Gelatinase B)

MMP-9 is isolated modifying the previously described procedures of Hibbs et al. (J. Biol. Chem., 260, 2493–2500, 1984) and Wilhelm et al. (J. Biol. Chem., 264, 17213–17221, 1989). Briefly, polymorphonuclear leukocytes (PMN) preparations are isolated as described above from 3 or more units of freshly drawn whole blood. Cells are resuspended in phosphate buffered saline (PBS) containing 100 ng/ml phorbol myristate acetate (PMA) in the presence of 50 mM di-isopropylfluorophospate (DFP), 1 µg/ml leupeptin and aprotinin, and 1 mg/ml catalase for 1 hr at 37° C. Supernatants are collected by centrifugation (300×g) and the samples are frozen at −70° C. All chromatographic methods are performed at 4° C. Thawed samples are concentrated 5-fold using an Amicon chamber equipped with a YM-10 membrane. The concentrate is pressure dialyzed against 0.02M Tris-HCl, 0.1 M NaCl, 1 mM $CaCl_2$, 1 µM $ZnCl_2$, 0.001% Brij-35, 0.02% sodium azide ($NaN_3$), pH 7.5 and applied to DEAE ion exchange chromatography resin which is previously equilibrated with the same buffer at a flow rate of 0.4 ml/min. The column is extensively washed with the same buffer and gelatinase is eluted as 4 ml fractions from the column with 0.02M Tris-HCl, 0.5 M NaCl, 1 mM $CaCl_2$, 1 µM $ZnCl_2$, 0.001% Brij-35, 0.02% $NaN_3$, pH 7.5. Gelatinase containing fractions are observed by gelatin zymography (see below), loaded onto a gelatin agarose affinity resin and washed with the same buffer. Gelatinase activity is eluted at a flow rate of 1 ml/min from the column as 1 ml fractions with 0.02M Tris-HCl, 1 M NaCl, 1 mM $CaCl_2$, 1 µM $ZnCl_2$, 0.001% Brij-35, 0.02% $NaN_3$, pH 7.5 containing 10% dimethyl sulfoxide (DMSO). The fractions containing gelatinase activity are pooled and dialyzed against 0.005M Tris-HCl, 5 mM NaCl, 0.5 mM $CaCl_2$, 0.1 µM $ZnCl_{2,\ 0.001}$% Brij-35, pH 7.4. The protein content associated with material is determined with a micro-BCA assay (Pierce, Rockford, Ill.), lyophilized and reconstituted to a desired working concentration (100 µg/ml). Recombinant human pro-MMP-9 is also expressed in baculovirus.

$K_m$ value: 22 µM

Assay Buffer: The assay is carried out in buffer containing 50 mM HEPES, 150 mM NaCl, 10 mM CaCl, 0.005% Brij-35, pH 7.0.

Enzyme concentrations for $IC_{50}$ determinations: 0.38 µg/ml

Enzyme concentrations for $K_i$ determinations: 0.38–1.00 µg/ml

MMP-12 (Macrophage Elastase)

MMP-9 is isolated according to the following procedure: Human GenePool cDNA libraries from human lung, spleen, and brain were obtained from Invitrogen (Groningen, The Netherlands). HPLC-purified oligonucleotides were purchased from BioTez (Berlin, Germany), *E. coli* strain DH5α from Life Technologies (Heidelberg, Germany), strain BL21 (DE3) from Novagen (Heidelberg, Germany). Pfu DNA-Polymerase and pBlueScriptII-KS(+) were from Stratagene (Heidelberg, Germany). DNA plasmid and DANN gel isolation kits were purchased from Qiagen (Hilden, Germany). All restriction enzymes and DNA modifying enzymes were ordered from New England Biolabs (Schwalbach, Germany). HiTrapQ (5 ml) was from Pharmacia Biotech (Freiburg, Germany). Vydac C4-RP HPLC columns (214TP54: 300 Å, 5 µm, 4.6×250 mm; 214TP1022: 300 Å, 10 µm, 22×250 mm) were from Promochem (Wesel, Germany). Fluorogenic substrate P218 was purchased from Polypeptide Laboratories (Wolfenbüttel, Germany). Ultrapure urea was purchased from Schwarz-Mann (Cleveland, Ohio). Ready-to-use NuPAGE 10% Bis-Tris Polyacrylamide SDS-PAGE gels and NuPAGE 20×MOPS running buffer were obtained from Novex (Frankfurt/Main, Germany) 10% AMPA and all other chemicals were from Sigma (Deisenhofen, Germany).

Molecular Cloning of MMP-12: The CDS for human MMP-12 (GenBank accession number: L23808; SwissProt accession number: P39900) was cloned by PCR out of the human normal spleen cDNA library with the gene-specific primers Oligo-428 (forward primer with BamH1-site underlined: 5'-aaa ttt aaa gga tcc gcc acc atg aag ttt ctt cta ata ctg ctc ctg-3') and Oligo-431 (reverse primer with EcoR1-site underlined: 5'-aaa ttt aaa gaa ttc att aac aac caa acc agc tat tgc ttt tca-3'). Removal of an internal EcoR1-site was done by PCR-mutagenesis with Oligo-434 (mutated base underlined: 5'-gcc tcc tga atg tgt agt cca gaa ctc gtc ctc atc gaa atg tgc atc-3'. The PCR reaction (100 μl volume) was carried out with Pfu DNA-polymerase in a Perkin Elmer GeneAmp 2400 PCR system with 25 cycles of denaturation (94° C., 1 min), annealing (60° C., 1 min) and extension (72° C., 2 min). The PCR product was gel purified by electrophoresis on 0.8% agarose/EthBr gels, separated from the agarose gel with the QiaEx2 DNA-isolation kit, cleaved with the restriction endonucleases BamH1/EcoR1, and purified again. This material was ligated into the cloning vector pBlueScriptII-KS(+), which was previously digested with BamH1 and EcoR1-cut and dephosphorylated with calf intestine alkaline phosphatase. The recombinant plasmid (PMYZ180) was transformed into E. coli strain DH5α. Plasmid DNA from several clones was isolated with the Qiagen plasmid preparation kit and analyzed by restriction digest. The DNA sequence of the MMP-12 complete CDS was determined by the dideoxy sequencing with dye terminator chemistry on an ABI 377 sequencer. Sequence analysis and all subsequent bioinformatic work was done with the software package Lasergene from DNAStar (Madison, Wis.). Sequence analysis of construct pMYZ 180 (4369 bp) identified silent mutations in the CDS of MMP-12 at positions 802 (G→A), 1402 (T→C), 1429 (C→T) and 2002 (T→C), which left the amino acid sequence of the protein unaffected.

Construction of Expression Vectors: In order to test the best strategy for both protein expression and protein purification, several different expression constructs with either full-length or partial sequences of the MMP-12 gene plus various affinity tags for purification were generated by PCR, The following constructs were made:

pMYZ187: The coding sequence for full-length human MMP-12 was cleaved via BamH1/EcoR1 digest out of pMYZ180, ligated into BamH1/EcoR1 cleaved pET-28a, and the complete coding sequence of final construct was verified by double-stranded DNA-sequencing.

pMYZ188: The coding sequence for full-length human MMP-12 was cleaved via BamH1/EcoR1 digest out of pMYZ180, ligated into BamH1/EcoR1 cleaved pET-32a, and the complete coding sequence of final construct was verified by double-stranded DNA-sequencing.

pMYZ189: The coding sequence for full-length human MMP-12 was cleaved via BamH1/EcoR1 digest out of pMYZ180, ligated into BamH1/EcoR1 cleaved pMYZ173 (a derivative of pET28a with an aminoterminal tag of the GB1 domain), and the complete coding sequence of final construct was verified by double-stranded DNA-sequencing.

pMYZ194: The coding sequence for amino acids 1–279 of human MMP-12 was amplified via PCR with primers Oligo-428 (forward primer with BamH1-site underlined: 5'-aaa ttt aaa gga tcc gcc acc atg aag ttt ctt cta ata ctg ctc ctg-3') and Oligo-486 (reverse primer with EcoR1-site underlined: 5'-ttt aaa ttt gaa ttc att atg gtt ctg aat tgt cag gat ttg gca-3') out of pMYZ180, cleaved with BamH1/EcoR1, ligated into BamH1/EcoR1 cleaved pET-28a, and the complete coding sequence of final construct was verified by double-stranded DNA-sequencing.

pMYZ195: The coding sequence for amino acids 1–264 of human MMP-12 was amplified via PCR with primers Oligo-428 (forward primer with BamH1-site underlined: 5'-aaa ttt aaa gga tcc gcc acc atg aag ttt ctt cta ata ctg ctc ctg-3') and Oligo-487 (reverse primer with EcoR1-site underlined: 5'-ttt aaa ttt gaa ttc att agt ctc cat aca ggg act gaa tgc cac-3') out of pMYZ180, cleaved with BamH1/EcoR1, ligated into BamH1/EcoR1 cleaved pET-28a, and the complete coding sequence of final construct was verified by double-stranded DNA-sequencing.

pMYZ198: The coding sequence for amino acids 1–279 of human MMP-12 was amplified via PCR with primers Oligo-428 (forward primer with BamH1-site underlined: 5'-aaa ttt aaa gga tcc gcc acc atg aag ttt ctt cta ata ctg ctc ctg-3') and Oligo-486 (reverse primer with EcoR1-site underlined: 5'-ttt aaa ttt gaa ttc att atg gtt ctg aat tgt cag gat ttg gca-3') out of pMYZ180, cleaved with BamH1/EcoR1, ligated into BamH1/EcoR1 cleaved pET-32a, and the complete coding sequence of final construct was verified by double-stranded DNA-sequencing.

pMYZ199: The coding sequence for amino acids 1–264 of human MMP-12 was amplified via PCR with primers Oligo-428 (forward primer with BamH1-site underlined: 5'-aaa ttt aaa gga tcc gcc acc atg aag ttt ctt cta ata ctg ctc ctg-3') and Oligo-487 (reverse primer with EcoR1-site underlined: 5'-ttt aaa ttt gaa ttc att agt ctc cat aca ggg act gaa tgc cac-3') out of pMYZ180, cleaved with BamH1/EcoR1, ligated into BamH1/EcoR1 cleaved pET-32a, and the complete coding sequence of final construct was verified by double-stranded DNA-sequencing.

pMYZ200: The coding sequence for amino acids 1–279 of human MMP-12 was amplified via PCR with primers Oligo-428 (forward primer with BamH1-site underlined: 5'-aaa ttt aaa gga tcc gcc acc atg aag ttt ctt cta ata ctg ctc ctg-3') and Oligo-486 (reverse primer with EcoR1-site underlined: 5'-ttt aaa ttt gaa ttc att atg gtt ctg aat tgt cag gat ttg gca-3') out of pMYZ180, cleaved with BamH1/EcoR1, ligated into BamH1/EcoR1 cleaved pMYZ173, and the complete coding sequence of final construct was verified by double-stranded DNA-sequencing.

pMYZ201: The coding sequence for amino acids 1–264 of human MMP-12 was amplified via PCR with primers Oligo-428 (forward primer with BamH1-site underlined: 5'-aaa ttt aaa gga tcc gcc acc atg aag ttt ctt cta ata ctg ctc ctg-3') and Oligo-487 (reverse primer with EcoR1-site underlined: 5'-ttt aaa ttt gaa ttc att agt ctc cat aca ggg act gaa tgc cac-3') out of pMYZ180, cleaved with BamH1/EcoR1, ligated into BamH1/EcoR1 cleaved pMYZ173, and the complete coding sequence of final construct was verified by double-stranded DNA-sequencing.

pMYZ215: The coding sequence for amino acids 17–279 of human MMP-12 was amplified via PCR with primers Oligo-513 (forward primer with Nde1-site underlined: 5'-aaa ttt aaa cat atg ctt ccc ctg aac agc tct aca agc ctg-3') and Oligo-486 (reverse primer with EcoR1-site underlined: 5'-ttt aaa ttt gaa ttc att atg gtt ctg aat tgt cag gat ttg gca-3') out of pMYZ180, cleaved with Nde1/EcoR1, ligated into Nde1/EcoR1 cleaved pET-28a, and the complete coding sequence of final construct was verified by double-stranded DNA-sequencing.

pMYZ216: The coding sequence for amino acids 17–264 of human MMP-12 was amplified via PCR with primers Oligo-513 (forward primer with Nde1-site underlined: 5'-aaa ttt aaa cat atg ctt ccc ctg aac agc tct aca agc ctg-3') and Oligo-487 (reverse primer with EcoR1-site underlined: 5'-ttt aaa ttt gaa ttc att agt ctc cat aca ggg act gaa tgc cac-3') out of pMYZ180, cleaved with Nde1/EcoR1, ligated into Nde1/EcoR1 cleaved pET-28a, and the complete coding sequence of final construct was verified by double-stranded DNA-sequencing.

pMYZ217: The coding sequence for amino acids 17–279 of human MMP-12 was amplified via PCR with primers Oligo-514 (forward primer with Nco1-site underlined: 5'-aaa ttt aaa gcc atg gct ctt ccc ctg aac agc tct aca agc ctg-3') and Oligo-486 (reverse primer with EcoR1-site underlined: 5'-ttt aaa ttt gaa ttc att atg gtt ctg aat tgt cag gat ttg gca-3') out of pMYZ180, cleaved with Nco1/EcoR1, ligated into Nco1/EcoR1 cleaved pET-32a, and the complete coding sequence of final construct was verified by double-stranded DNA-sequencing.

pMYZ218: The coding sequence for amino acids 17–264 of human MMP-12 was amplified via PCR with primers Oligo-514 (forward primer with Nco1-site underlined: 5'-aaa ttt aaa gcc atg gct ctt ccc ctg aac agc tct aca age ctg-3') and Oligo-487 (reverse primer with EcoR1-site underlined: 5'-ttt aaa ttt gaa ttc att agt ctc cat aca ggg act gaa tgc cac-3') out of pMYZ180, cleaved with Nco1/EcoR1, ligated into Nco1/EcoR1 cleaved pET-32a, and the complete coding sequence of final construct was verified by double-stranded DNA-sequencing.

pMYZ219: The coding sequence for amino acids 17–279 of human MMP-12 was amplified via PCR with primers Oligo-515 (forward primer with BamH1-site underlined: 5'-aaa ttt aaa gga tcc ctt ccc ctg aac age tct aca age ctg-3') and Oligo-486 (reverse primer with EcoR1-site underlined: 5'-ttt aaa ttt gaa ttc att atg gtt ctg aat tgt cag gat ttg gca-3') out of pMYZ180, cleaved with BamH1/EcoR1, ligated into BamH1/EcoR1 cleaved pMYZ173, and the complete coding sequence of final construct was verified by double-stranded DNA-sequencing.

pMYZ220: The coding sequence for amino acids 17–264 of human MMP-12 was amplified via PCR with primers Oligo-515 (forward primer with BamH1-site underlined: 5'-aaa ttt aaa gga tcc ctt ccc ctg aac agc tct aca agc ctg-3') and Oligo-487 (reverse primer with EcoR1-site underlined: 5'-ttt aaa ttt gaa ttc att agt ctc cat aca ggg act gaa tgc cac-3') out of pMYZ180, cleaved with BamH1/EcoR1, ligated into BamH1/EcoR1 cleaved pMYZ173, and the complete coding sequence of final construct was verified by double-stranded DNA-sequencing.

pMYZ227: The coding sequence for amino acids 100–279 of human MMP-12 was amplified via PCR with primers Oligo-533 (forward primer with Nde1-site underlined: 5'-aaa ttt aaa cat atg ttc agg gaa atg cca ggg ggg ccc gta tgg-3') and Oligo-486 (reverse primer with EcoR1-site underlined: 5'-ttt aaa ttt gaa ttc att atg gtt ctg aat tgt cag gat ttg gca-3') out of pMYZ180, cleaved with Nde1/EcoR1, ligated into Nde1/EcoR1 cleaved pET-29a, and the complete coding sequence of final construct was verified by double-stranded DNA-sequencing.

pMYZ228: The coding sequence for amino acids 100–264 of human MMP-12 was amplified via PCR with primers Oligo-533 (forward primer with Nde1-site underlined: 5'-aaa ttt aaa cat atg ttc agg gaa atg cca ggg ggg ccc gta tgg-3') and Oligo-487 (reverse primer with EcoR1-site underlined: 5'-ttt aaa ttt gaa ttc att agt ctc cat aca ggg act gaa tgc cac-3') out of pMYZ180, cleaved with Nde1/EcoR1, ligated into Nde1/EcoR1 cleaved pET-28a, and the complete coding sequence of final construct was verified by double-stranded DNA-sequencing.

Bacterial Expression: Batches of one liter of LB medium (10 g tryptone, 5 g yeast extract, 10 g NaCl) containing ampicillin (200 μg/ml) or kanamycin (100 μg/ml) were inoculated with 20 ml each of overnight culture of E. coli BL21 (DE3) cells with the appropriate expression vector. Cells were cultured at 37° C. to an OD600 of about 0.8 before induction with IPTG (1 mM final concentration). Incubation was continued at 37° C. for 4 hours before harvesting by centrifugation. Cell pellets were frozen immediately and kept at −20° C. until use. Aliquots (100 μl) were taken from each cell culture and analyzed for protein expression on 10% SDS-PAGE gels.

Protein Purification: Frozen cell pellets from 1 liter bacterial cells were thawed, dissolved in 50 ml Tris/HCl, pH 8.0 with 15% glycerol, sonicated with 4 pulses a 10 sec and centrifuged for 30 min at 20,000 rpm with a JA-20 rotor. After removal of the supernatant, the inclusion bodies in the pellet were dissolved over night at room temperature with 50 ml 8M urea, 50 mM Tris/HCl, pH 8.0 upon gentle shaking. The next day, the solution was centrifuged for 30 min at 20,000 rpm with a JA-20 rotor and the supernatant used for further purification. Batches of 5–10 ml were applied to a 5 ml HiTrapQ ion exchange column running in 8M urea, 50 mM Tris/HCl, pH 8.0 (buffer A). After sample loading and washing of the column, protein was eluted by increasing the salt concentration with a solution of 8M urea, 50 mM Tris/HCl, pH 8.0+1.0 M NaCl (buffer B) in a linear gradient of 0–50% buffer B within 40 column volumes. Fractions with protein elution at around 30% buffer B were tested for purity by denaturing SDS-PAGE and mass spectrometry, and the fractions containing MMP-12 were pooled together. From this solution, 5–10 ml batches were taken, acidified to a final concentration of 10% acetic acid, and injected onto a preparative C4-RP-HPLC column (Vydac 214TP1022: 300 Å, 10 μm, 22×250 mm) with a flow rate of 10 ml/min on a Waters HPLC chromatography workstation. Starting buffer was $H_2O$/0.1% TFA (buffer A), and elution buffer was 90% $CH_3CN$/10% $H_2O$/0.1% TEA (buffer B). The pure protein eluted as a single peak at around 35% buffer B and the protein containing fractions were again analyzed by denaturing SDS-PAGE and mass-spectrometry. Pooled fractions with MMP-12 protein were frozen in liquid $N_2$ and freeze-dried for 3–5 days. Lyophilized protein was stored at −20° C.

$K_m$ value: 5.4 μM

Assay Buffer: The assay is carried out in buffer containing 50 mM HEPES and 10 mM $CaCl_2$, pH 7.0.

Enzyme concentrations for $IC_{50}$ determinations: 0.3 μg/ml

Enzyme concentrations for $K_i$ determinations: 0.044–0.98 μg/ml

MMP-13 (Human Collagenase 3)

Rat pro-MMP-13 was obtained according to the protocol of Roswit, Arch. Biochem. Biophys. 225, 285–295 (1983) and activated by incubating in 1:10 Trypsin.

Assay Buffer: The assay is carried out in buffer containing 20 mM Tris pH 7.5, 250 mM NaCl, 5 mM $CaCl_2$, 0.05% $NaN_3$, 0.005% Brij Enzyme concentrations for $IC_{50}$ determinations: 0.3 μg/ml $IC_{50}$-values of selected compounds are given in the following table 3. The compound numbers refer to the compounds as depicted in table 1:

| Compound No. | IC$_{50}$ MMP-12 [nM] |
|---|---|
| C-III | 2.8 |
| C-V | 1.7 |
| C-XVIII | 1.0 |
| C-XXII | 1.6 |
| C-XXX | 4.5 |

The following data illustrate the selectivity of examples of the invention for MMP-2, MMP-3, MMP-8, MMP-9, MMP-12 and MMP-13. The example numbers refer to the examples as described in the experimental part:

TABLE 4

| Example | Species | Potency [K$_i$, nM] vs. MMP-x ||||||| 
| | | 1 | 2 | 3 | 7 | 8 | 9 | 12 | 13 |
|---|---|---|---|---|---|---|---|---|---|
| 4 | rat | | | | | | | | 296* |
|   | human | 639 | 0.5 | 3.7 | >3000 | 7.5 | 0.7 | 0.3 | 5.6 |
| 2 | rat | | | | | | | | 69* |
|   | human | >3000 | 3.2* | 60* | 38% inh. at 30 nM | 21.6* | 1.2 | 0.03 | 70* |

*IC$_{50}$ [nM]

In vitro Functional Tests
1. Human alveolar macrophages

Human alveolar macrophages were obtained by bronchoscopy of healthy smoking volunteers. Cells were spun and resuspended at 2×10$^6$/ml. Trafficking of alveolar macrophages (+or −lipopolysaccharide 2.5 μg.ml) across an artificial basement membrane (Matrigel) was induced by human MCP-1 (5 ng/ml) over a 48–98 h period. (1α,2β,5β)-2-{[4'-chloro(1,1'-biphenyl)-4-yl]carbonyl}-5-[(1,3-dihydro-1,3-dioxo-2H-isoindol-2-yl)methyl]-cyclopentane carboxylic acid inhibited the MCP-1-induced trafficking of human alveolar macrophages across this artificial basement membrane (IC$_{50}$≦1 μM).

2. Murine peritoneal macrophages

Murine macrophages were obtained from mice 5 days after an intraperitoneal injection of thioglycollate. Cells were spun and resuspended at 2×10$^6$/ml. Trafficking of peritoneal macrophages across an artificial basement membrane (Matrigel) was induced by murine MCP-1 (5 ng/ml) over a 48–98 h period. (1α,2β,5β)-2-{[4'-chloro(1,1'-biphenyl)-4-yl]carbonyl}-5-[(1,3-dihydro-1,3-dioxo-2H-isoindol-2-yl)methyl]-cyclopentane carboxylic acid inhibited the trafficking of murine peritoneal macro-phages across this artificial basement membrane (IC$_{50}$≦1 μM).

LPS Induced TNFα Production in Mice

The in vivo inhibitory properties of selected compounds can be determined using a murine LPS induced TNFα production in vivo model. BALB/c mice (Charles River Breeding Laboratories; Kingston, N.Y.) in groups of ten are treated with either vehicle or compound. After one hour, endotoxin (E. coli lipopolysaccharide (LPS) 100 mg) is administered intraperitoneally (i.p.). After 90 min, animals are euthanized by carbon dioxide asphyxiation and plasma is obtained from individual animals by cardiac puncture into heparinized tubes, The samples are clarified by centrifugation at 12,500×g for 5 min at 4° C. The supernatants are decanted to new tubes, which are stored as needed at −20°

C. TNFα levels in sera are measured using a commercial murine TNF ELISA kit (Genzyme).

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

Abbreviations:

DMF: N,N-Dimethylformamide

RT: room temperature

THF: Tetrahydrofuran

PREPARATION EXAMPLES

Example 1

2-[2-(1,3-Dioxo-1,3-dihydro-2H-isoindol-2-yl)ethyl]-4-(4'-ethoxy[1,1'-biphenyl]-4-yl)-4-oxobutanoic acid

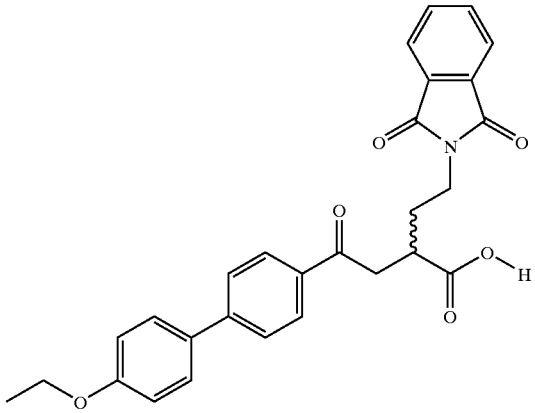

Intermediate 1A
4-Ethoxy-1,1'-biphenyl

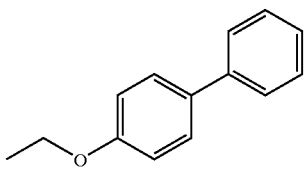

Iodoethane (68.7 g, 35,57 mL, 440.6 mmol) was added to a suspension of 50 g (170.2 mmol) of 4-hydroxy-1,1'-biphenyl and 40.6 g (293.75 mmol) K$_2$CO$_3$ in 600 mL acetone. The resulting reaction mixture was stirred under reflux for 16 hours. After cooling to room temperature the acetone was removed under reduced pressure, the residue was dissolved in ethyl acetate and extracted with water. The aqueous layers where extracted 3 times with ethyl acetate, the combined organic phases dried ($Na_2SO_4$) and evaporated to yield 56 g of the desired compound as a colorless solid.

Yield: 56 g (96%).

$^1$H-NMR ($d_6$-DMSO): 7.55–7.65 (m, 4H), 7.42 (t, J=8 Hz, 2H), 7.3 (t, J=8 Hz, 1H), 6.95–7.05 (m, 2H), 4.07 (q, J=7 Hz, 2H), 1.35 (t, J=7 Hz, 3H).

Intermediate 1B

2-Bromo-1-(4'-ethoxy[1,1'-biphenyl]-4-yl)-1-ethanone

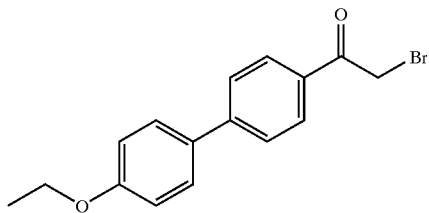

A solution of 56 g (282 mmol) of Intermediate 1A in 1.5 L $CH_2Cl_2$ was cooled to 0° C. and placed under argon. Bromoacetyl bromide (85.5 g, 36,8 mL, 423 mmol) was added, and then $AlCl_3$ (37.41 g, 280.53 mmol) was added in portions over 60 min. After the addition was complete, the mixture was stirred for 20 h, warming to RT. The mixture was then poured slowly into a stirred mixture of 2 kg ice/500 ml conc. HCl. The organic layer was separated, washed with 2N HCl and water, dried ($Na_2SO_4$) and evaporated. The crude product was purified by recrystallization (acetonitril) to give 49.3 g (54%) white solid.

$^1$H-NMR ($d_6$-DMSO): 8.08 (d, J=8 Hz, 2H), 7.81 (d, J=8 Hz, 2H), 7.73 (d, J=8 Hz, 2 Hz), 7.06 (d, J=8 Hz, 2H), 4.95 (s, 2H), 4.1 (q, J=7 Hz, 2H), 1:36 (t, J=7 Hz, 3H).

Intermediate 1C

Di(tert-butyl) 2-[2-(1,3-dioxo-1,3-dihydro-2H-isoindol-2-yl)ethyl]-2-[2-(4'-ethoxy-1,1'-biphenyl-4-yl)-2-oxoethyl] malonate

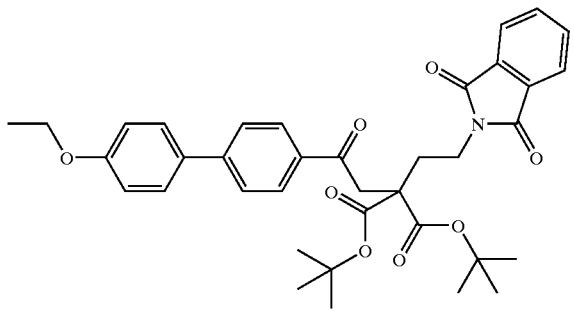

A solution of Intermediate 5F (3.2 g, 10 mmol) in 50 mL DMF was added dropwise to a suspension of NaH (500 mg, 12.5 mmol) in 20 mL DMF and stirred for 30 min at RT. Intermediate 1B (3.9 g, 10 mmol) in 30 ml DMF was added slowly and the resulting mixture was stirred for 4 h at RT. The reaction was quenched with saturated $NH_4Cl$ solution, extracted twice with diethyl ether, washed with saturated $NaHCO_3$, water and brine, dried ($Na_2SO_4$) and evaporated. The crude product was purified using flash chromatography (hexane/ethyl acetate: 1/1).

Yield: 4.96 g (71%).

$^1$H-NMR ($d_6$-DMSO): 8.02 (d, J=8 Hz, 2H), 7.68–7.81 (m, 8H), 7.05 (d, J=8 Hz, 2H), 4.1 (q, J=7 Hz, 2H), 3.72 (s, 2H), 3.55–3.65 (m, 2H), 2.26–2.87 (m, 2H), 1.33–1.4 (m, 18H).

Example 1

2-[2-(1,3-Dioxo-1,3-dihydro-2H-isoindol-2-yl)ethyl]-4-(4'-ethoxy[1,1'-biphenyl]-4-yl)-4-oxobutanoic acid

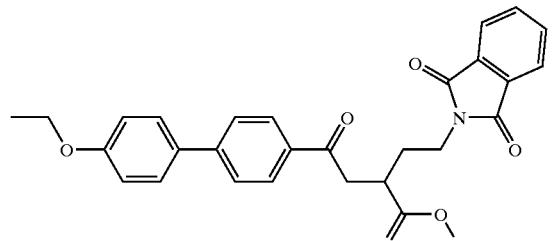

2.2 g (3.51 mmol) of Intermediate 1C was added in one portion to a cooled (0° C.) 1:1 mixture of $CH_2Cl_2$ and trifluoroacetic acid. The reaction mixture was stirred overnight at RT, evaporated and dried under vacuum. The residue was dissolved in 5 mL dioxane and heated for 5 h under reflux. The rection mixture was evaporated, the residue triturated with diethyl ether, stirred for 15 min and filtered. The remaining solid was dried under vacuum.

Yield: 1.21 g (73%).

$^1$H-NMR ($d_6$-DMSO): 12.28 (s, 1H), 8.02 (d, J=8 Hz, 2H), 7.67–7.9 (m, 8H), 7.05 (d, I=8 Hz, 2H), 4.1 (q, J=7 Hz, 2H), 3.72 (t, J=7.5 Hz, 2H), 3.49 (dd, J=17.5 Hz, J=8 Hz, 2H), 3.28 (dd, J=17.5 Hz, J=5 Hz, 2H), 2.78–2.95 (m, 1H), 1.76–2.13 (m, 2H), 1.38 (t, J=7 Hz, 3H).

The racemate of Example 1 was separated into its pure enantiomers via chiral HPLC using a commercially available 5 µm Kromasil KR 100-5-CHI-DMB phase. A solvent mixture consisting of 50% iso-hexane and 50% of a tert-butylmethyl ether/dichloromethane/glacial acetic acid mixture (480:40:1) was employed at a constant flow rate of 25 ml/min.

Example 2

(+)-2-[2-(1,3-Dioxo-1,3-dihydro-2H-isoindol-2-yl)ethyl]-4-(4'-ethoxy[1,1'-biphenyl]-4-yl)-4-oxobutanoic acid Faster eluting enantiomer:

Yield: 374 mg (42%).

$[\alpha]^{23}_D$+6.33° (c=0.47 in THF).

Example 3

(−)-2-[2-(1,3-Dioxo-1,3-dihydro-2H-isoindol-2-yl)ethyl]-4-(4'-ethoxy[1,1'-biphenyl]-4-yl)-4-oxobutanoic acid Slower eluting enantiomer:

Yield: 321 mg (36%).

$[\alpha]^{23}_D$−5.6° (c=0.5 in THF).

Example 4

(+)-4-(4'-Chloro[1,1'-biphenyl]4-yl)-2-[2-(1,3-dioxo-1,3-dihydro-2H-isoindol-2-yl)ethyl]-4-oxobutanoic acid

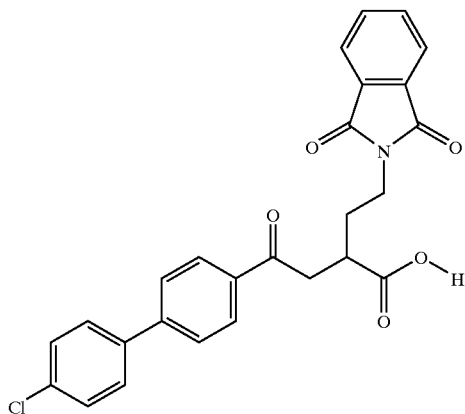

The compound of Example 4 was prepared according to the procedure given for Example 268 in WO 96/15096. [α]$_D^{23}$+5.55° (c=0.525 in THF).

Example 5

(rac)-4-[4'-(Acetyloxy)[1,1'-biphenyl]-4-yl]-2-[2-(1,3-dioxo-1,3-dihydro-2H-isoindol-2-yl)-ethyl]-4-oxobutanoic acid Intermediate 5A 4'-(2-Bromoacetyl)[1,1'-biphenyl]-4-yl acetate

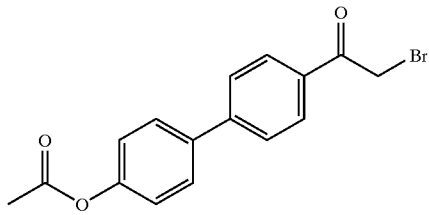

A solution of 50 g (236 mmol) of [1,1'-biphenyl]-4-yl acetate in 500 ml dichloromethane was placed under argon and cooled to 0° C. Bromoacetyl bromide (31.6 ml, 363 mmol) was added, followed by aluminium chloride (94.3 g, 707 mmol) which was added in portions under vigorous stirring over 30 min. The resulting mixture was stirred at 0° C. for a further 30 min and at room temperature overnight. The mixture was then slowly poured into 500 ml of cold 10% HCl and extracted three times with dichloromethane. The organic layer was dried over Na$_2$SO$_4$, filtered and evaporated. The residue was triturated with 1:1 diisopropyl ether/isopropanol, filtered, and the remaining solid dried under vacuum.

Yield: 73.3 g (93.4%).

$^1$H-NMR (CDCl$_3$): δ=2.34 (s, 3H), 4.48 (s, 2H), 7.21 (m, 2H), 7.66 (m, 4H), 8.08 (m, 2H).

Intermediate 5B 2-(Benzyloxy)-1-ethanol

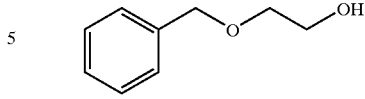

Ethylene glycol (742.5 g, 11.96 mol) was added to a solution of sodium hydroxide pellets (475.2 g, 11.88 mol) in 450 ml of water kept at 80° C. Benzyl chloride (302.8 g, 2.39 mol) was then added at 65° C., and the resulting suspension was vigorously stirred at 120° C. overnight. After cooling to room temperature, the mixture was poured into ice-water and extracted five times with diethyl ether. The combined organic layers were washed with brine, dried over Na$_2$SO$_4$, filtered and evaporated. The remaining residue was then distilled under vacuum and the relevant fractions (bp. 95–125° C. at 0.1–1 mbar) collected.

Yield: 175 g (48.1%) of a colourless liquid.

$^1$H-NMR (CDCl$_3$): δ=2.09 (tr, 1H), 3.60 (m, 2H), 3.77 (m, 2H); 4.56 (s, 2H) 7.35 (m, 5H).

Intermediate 5C

Benzyl 2-chloroethyl ether

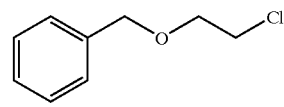

Thionyl chloride (41.2 ml, 567.6 mmol) was slowly added to a mixture of Intermediate 5B (90 g, 80% purity, 473.1 mmol) and N,N-dimethyl aniline (76.5 ml, 597.5 mmol) while keeping the reaction temperature at 50° C. by ice-water cooling. After stirring at 50° C. for 1 h, further portions of N,N-dimethyl aniline (15.3 ml, 119.5 mmol) and thionyl chloride (8.2 ml, 113.5 mmol) were added, and the mixture was stirred at 50° C. for another 2 h and at room temperature overnight. The solution was then poured into a mixture of ice-water (200 ml) and conc. HCl (100 ml) and extracted three times with dichloromethane. The combined organic layers were washed twice with 10% HCl and twice with water, dried over Na$_2$SO$_4$, filtered and evaporated. The remaining residue was then distilled under vacuum (water pump) and the relevant fractions collected.

Yield: 69.1 g (85.6%) of a colourless liquid.

$^1$H-NMR (CDCl$_3$): δ=3.69 (m, 4H), 4.59 (s, 2H), 7.35 (m, 5H).

Intermediate 5D

Di(tert-butyl) 2-[2-(benzyloxy)ethyl]malonate

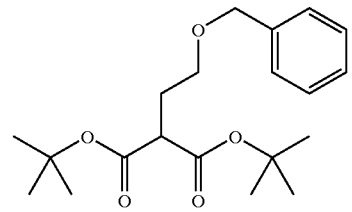

Di(tert-butyl) malonate (151.4 g, 686 mmol) was added dropwise at 50° C. to a suspension of potassium tert-butylate (77 g, 686 mmol) in 500 ml of tert-butanol. Sodium iodide (10.33 g) was then added, followed by dropwise addition of Intermediate 5C (117.1 g, 686 mmol) at 40–50° C. The resulting thick suspension was stirred at 70° C. for two days. During this time, two further portions of potassium tert-butylate (15.4 g each, 70 mmol) were added. The mixture was then poured into ice-water and extracted three times with diethyl ether. The organic layers were dried over Na₂SO₄, filtered and evaporated. The crude product was finally purified by column chromatography using a cyclohexane/ethyl acetate gradient (70:1→15:1).

Yield: 134 g (55.8%) of a colourless oil.

¹H-NMR (DMSO-d₆): δ=1.38 (s, 18H), 1.96 (q, 2H), 3.31 (tr, 1H), 3.41 (tr, 2H), 4.43 (s, 2H), 7.31 (m, 5H).

Intermediate 5E

Di(tert-butyl) 2-(2-hydroxyethyl)malonate

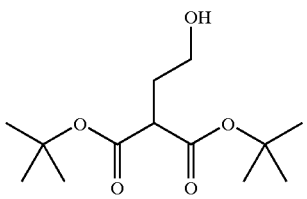

A solution of Intermediate 5D (46.58 g, 132.9 mmol) in 300 ml ethanol was hydrogenated at atmospheric pressure in the presence of 10% palladium on charcoal (2.0 g). After stirring for 3 h at room temperature, another 1.0 g portion of palladium catalyst was added, and stirring was continued at room temperature overnight. The mixture was then filtered through celite, evaporated, and the crude product purified by column chromatography using a dichloromethane/methanol gradient (70:1→30:1).

Yield; 23.3 g (67.2%) of a pale yellow oil.

¹H-NMR (CDCl₃): δ=1.47 (s, 18H), 1.96 (tr, 1H), 2.08 (q, 2H), 3.36 (tr, 1H), 3.72 (q, 1H).

Intermediate 5F

Di(tert-butyl) 2-[2-(1,3-dioxo-1,3-dihydro-2H-isoindol-2-yl)ethyl]malonate

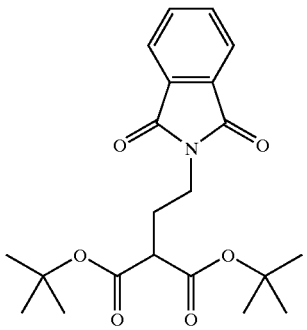

To a stirred solution of Intermediate 5E (30.0 g, 115.2 mmol) in 255 ml of dry THF were added successively phthalimide (21.4 g, 144.1 mmol), triphenyl phosphine (35.1 g, 132.5 mmol) and, at 0° C., diethyl azodicarboxylate (22.1 g, 126.8 mmol). The resulting solution was stirred overnight while warming up to room temperature, then diluted with ethyl acetate and washed twice with water and with brine. The organic phase was dried over Na₂SO₄, filtered and evaporated. The crude product was finally purified by column chromatography using a cyclohexane/dichloromethane/ethyl acetate gradient (7:1:1→5:1:1).

Yield: 10.02 g (22.3%) of a white solid.

¹H-NMR (DMSO-d₆): δ=1.37 (s, 18H), 2.03 (q, 2H), 3.30 (tr, 1H), 3.63 (tr, 2H), 7.85 (m, 4H).

Intermediate 5G

Di(tert-butyl) 2-{2-[4'-(acetyloxy)[1,1'-biphenyl]-4-yl]-2-oxoethyl}-2-[2-(1,3-dioxo-1,3-dihydro-2H-isoindol-2-yl)ethyl]malonate

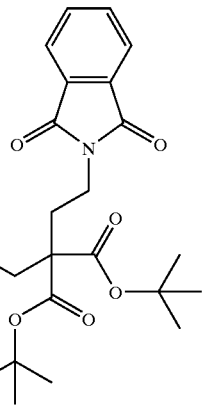

Under argon, a solution of Intermediate 5F (6.5 g, 16.69 mmol) in 60 ml of dry THF was added dropwise at 0° C. to a suspension of sodium hydride (0.51 g, 80% suspension in mineral oil, 16.86 mmol) in 30 ml of dry THF. After stirring at 30–40° C. for 30 min, the mixture was recooled to 0° C., and a solution of Intermediate 5A (5.6 g, 16.86 mmol) in 60 ml of dry THF was added dropwise. The mixture was then stirred overnight while warming up to room temperature. Further portions of sodium hydride (0.1 g, 3.4 mmol) and Intermediate 5A (1.12 g, 3.4 mmol) were added at 0° C., and stirring was continued at room temperature for another 3 h. The reaction mixture was quenched by addition of saturated ammonium chloride solution (100 ml) and brine (200 ml), and extracted twice with ethyl acetate. The organic phase was dried over Na₂SO₄, filtered and evaporated. The crude product was finally purified by column chromatography using a dichloro-methane/ethyl acetate gradient (50:1→30:1).

Yield: 4.41 g (41.2%) of an off-white solid.

¹H-NMR (DMSO-d₆): δ=1.38 (s, 18H), 2.32 (m, 5H), 3.61 (tr, 2H), 3.73 (s, 2H), 7.28 (d, 2H), 7.81 (m, 8H), 8.04 (d, 2H).

Example 5

(rac)-4-[4'-(Acetyloxy)[1,1'-biphenyl]-4-yl]-2-[2-(1,3-dioxo-1,3-dihydro-2H-isoindol-2-yl)ethyl]-4-oxobutanoic acid

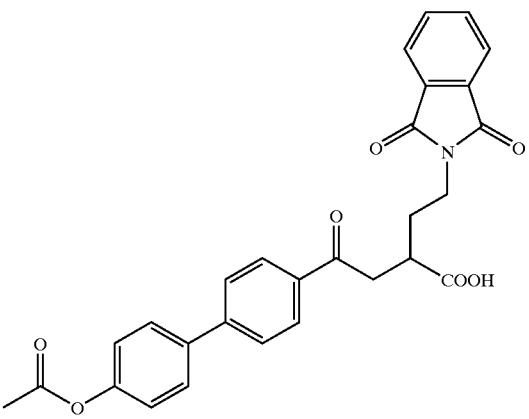

Intermediate 5G (400 mg, 0.62 mmol) was dissolved at 0° C. in a mixture of dichloromethane (5 ml) and trifluoroacetic acid (5 ml). After stirring at room temperature for 1.5 h, 10 ml of toluene were added, and the reaction mixture was evaporated. The residue was dried under vacuum, then re-dissolved in 20 ml of dioxane, and the solution heated under reflux for 6 h. The mixture was evaporated to dryness, the residue triturated with diethyl ether, filtered, and the remaining solid dried under vacuum to give the final product Yield: 261 mg (86.2%) of an off-white solid.

$^1$H-NMR (DMSO-$d_6$): δ=1.95 (m, 2H), 2.31 (s, 3H), 2.89 (m, 1H), 3.38 (m, 2H), 3.72 (tr, 2H), 7.28 (d, 2H), 7.84 (m, 8H), 8.07 (d, 2H), 12.33 (br s, 1H).

Example 6

(rac)-2-[2-(1,3-Dioxo-1,3-dihydro-2H-isoindol-2-yl) ethyl]-4-(4'-hydroxy[1,1'-biphenyl]-4-yl)-4-oxobutanoic acid Intermediate 6A Di(tert-butyl) 2-[2- (1,3-dioxo-1,3-dihydro-2H-isoindol-2-yl)ethyl]-2-[2-(4'-hydroxy-[1,1'-biphenyl]-4-yl)-2-oxoethyl]malonate

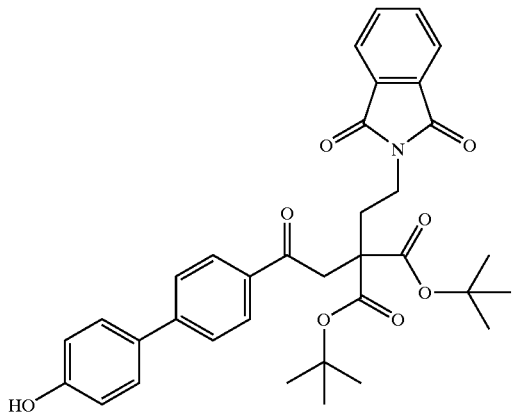

Finely powdered, anhydrous potassium carbonate (2.15 g, 15.58 mmol) was added to a solution of Intermediate 5G (2.0 g, 3.12 mmol) in 90 ml of a THF/methanol/ethanol mixture (30:50:10). The resulting suspension was vigorously stirred at room temperature for 45 min, then diluted with ethyl acetate and filtered. The filtrate was concentrated under vacuum to half of its original volume, diluted again with ethyl acetate, and then poured into an ice-cold pH 4 buffer solution. The aqueous phase was extracted twice with ethyl acetate, and the combined organic layers were dried over Na$_2$SO$_4$, filtered and evaporated. After drying under vacuum, 700 mg (approx. 1.1 mmol) of the residue (which contained some ring-opened material) were dissolved in 20 ml of dichloromethane, and 1-hydroxy-1H-benzotriazol hydrate (189 mg, 1.23 mmol) and N'-(3-dimethylaminopropyl)-N-ethylcarbodiimide hydrochloride (229 mg, 1.18 mmol) were added at 0° C. The reaction mixture was stirred at room temperature for 3 days, then diluted with dichloromethane, and washed twice with pH 4 buffer solution and with saturated sodium hydrogencarbonate solution. The organic phase was dried over Na$_2$SO$_4$, filtered and evaporated. The crude product was finally purified by column chromatography using a dichloromethane/methanol gradient (100:1→80:1).

Yield: 494 mg (71%) of a white solid.

$^1$H-NMR (DMSO-$d_6$): δ=1.38 (s, 18H), 2.31 (m, 2H), 3.60 (m, 2H), 3.70 (s, 2H), 6.90 (d, 2H), 7.61 (d, 2H), 7.78 (m, 6H), 8.00 (d, 2H), 9.76 (s, 1H).

Example 6

(rac)-2-[2-(1,3-Dioxo-1,3-dihydro-2H-isoindol-2-yl) ethyl]-4-(4'-hydroxy[1,1'-biphenyl]-4-yl)-4-oxobutanoic acid

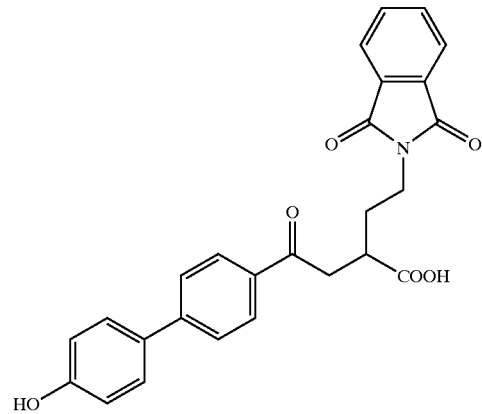

Intermediate 6A (490 mg, 0.82 mmol) was dissolved at 0° C. in a mixture of dichloromethane (7.5 ml) and trifluoroacetic acid (7.5 ml). After stirring at room temperature for 30 min, 7 ml of toluene were added, and the reaction mixture was evaporated. The residue was dried under vacuum, then re-dissolved in 15 ml of dioxane, and the solution heated under reflux for 4.5 h. After cooling to room temperature, diethyl ether (15 ml) was added to the reaction mixture, and the precipitated product collected by filtration. The filtrate was evaporated to dryness, the residue triturated with diethyl ether, containing a few drops of methanol, and filtered again to give a second crop of the final product.

Yield: 299 mg (82.6%) of a white solid.

$^1$H-NMR (DMSO-$d_6$): δ=1.94 (m, 2H), 2.87 (m, 1H), 3.38 (m, 2H), 3.70 (tr, 2H), 6.89 (d, 2H), 7.61 (d, 2H), 7.75 (d, 2H), 7.85 (m, 4H), 8.01 (d, 2H), 9.76 (br s, 1H), 12.30 (br s, 1H).

Example 7

(rac)-4-(4'-Chloro[1,1'-biphenyl]-4-yl)-2-[2-(4,6-dimethoxy-1,3-dioxo-1,3-dihydro-2H-isoindol-2-yl) ethyl]-4-oxobutanoic acid Intermediate 7A 2-Bromo-1-(4'-chloro[1,1'-biphenyl]-4-yl)-ethanone

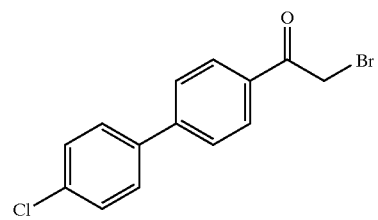

This intermediate was prepared as described in the indicated reference WO 96/15096.

Intermediate 7D

Di(tert-butyl) 2-[2-(4,6-dimethoxy-1,3-dioxo-1,3-dihydro-2H-isoindol-2-yl)ethyl]malonate

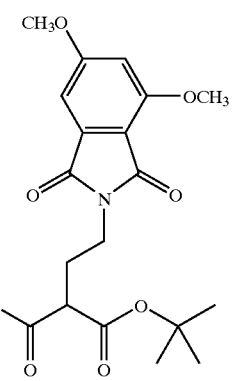

To a stirred solution of Intermediate 5E (8.4 g, 32.2 mmol) in 100 ml of dry THF were added successively 3,5-diethoxyphthalimide (10.0 g, 48.3 mmol), triphenyl phosphine (11.1 g, 41.8 mmol) and, at 0° C., diethyl azodicarboxylate (6.7 g, 38.6 mmol). The resulting solution was stirred overnight while warming up to room temperature. After filtration, the filtrate was diluted with ethyl acetate and washed twice with water and with brine. The organic phase was dried over Na$_2$SO$_4$, filtered and evaporated. The crude product was finally purified by column chromatography using a dichloromethane/ethyl acetate gradient (70:1→30:1).

Yield: 2.69 g (18.6%) of a white solid.

$^1$H-NMR (DMSO-d$_6$): δ=1.38 (s, 18H), 1.97 (q, 2H), 3.23 (tr, 1H), 3.54 (tr, 2H), 3.92 (s, 6H), 6.89 (d, 1H), 6.97 (d, 1H).

Intermediate 7C

Di(tert-butyl) 2-[2-(4'-chloro[1,1'-biphenyl]-4-yl)-2-oxoethyl]-2-[2-(4,6-dimethoxy-1,3-dioxo-1,3-dihydro-2H-isoindol-2-yl)ethyl]malonate

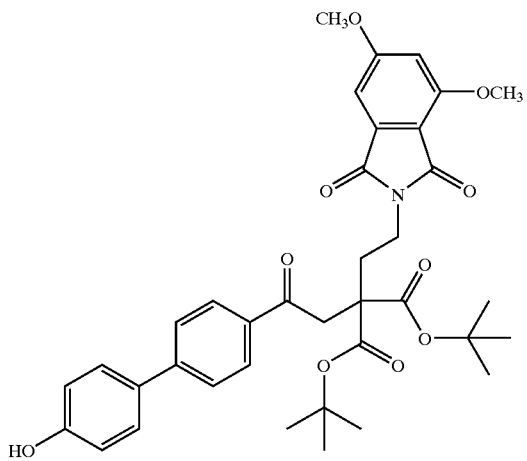

Under argon, a solution of Intermediate 7B (2.69 g, 5.98 mmol) in 30 ml of dry THF was added dropwise at 0° C. to a suspension of sodium hydride (0.18 g, 80% suspension in mineral oil, 6.04 mmol) in 20 ml of dry THF. After stirring at 30–40° C. for 30 min, the mixture was re-cooled to 0° C., and a solution of Intermediate 3A (1.87 g, 6.04 mmol) in 20 ml of dry THF was added dropwise. The mixture was then stirred overnight while warming up to room temperature. Further portions of sodium hydride (36 mg, 1.2 mmol) and Intermediate 7A (374 mg, 1.2 mmol) were added at 0° C., and stirring was continued at room temperature for three days. The reaction mixture was quenched by addition of saturated ammonium chloride solution (40 ml) and brine (80 ml), and extracted twice with ethyl acetate. The organic phase was dried over Na$_2$SO$_4$, filtered and evaporated. The crude product was finally purified by column chromatography using a dichloro-methane to dichloromethane/ethyl acetate (20:1) gradient.

Yield: 1.51 g (37.2%) of a white solid.

R$_F$=0.51 (dichloromethane/ethyl acetate 20:1);

=0.59 (cyclohexane/ethyl acetate 1:1).

ESI-MS: m/z=678 [M+H]$^+$, 622 ([M+H]$^+$–C$_4$H$_8$), 566 ([M+H]$^+$–2×C$_4$H$_8$), 548 ([M+H]$^+$–2×C$_4$H$_8$/–H$_2$O).

Example 7

4-(4'-Chloro[1,1'-biphenyl]-4-yl)-2-[2-(4,6-dimethoxy-1,3-dioxo-1,3-dihydro-2H-isoindol-2-yl)ethyl]oxobutanoic acid

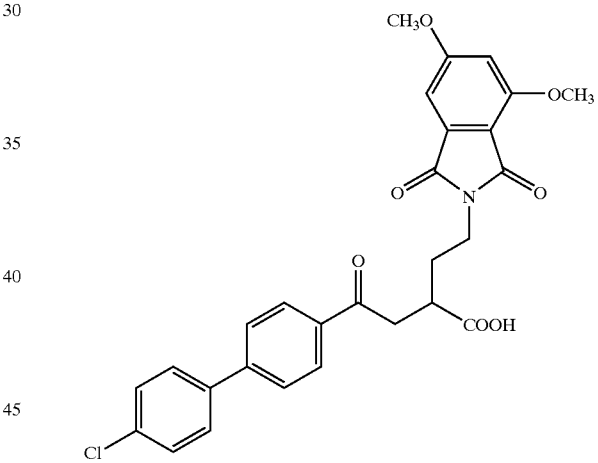

Intermediate 7C (1.5 g, 2.2 mmol) was dissolved at 0° C. in a mixture of dichloromethane (10 ml) and trifluoroacetic acid (10 ml). After stirring at room temperature for 45 min, 10 ml of toluene were added, and the reaction mixture was evaporated.

The residue was dried under vacuum, then redissolved in 20 ml of dioxane, and the solution heated under reflux for 6 h. The mixture was evaporated to dryness, the residue triturated with diethyl ether, filtered, and the remaining solid dried under vacuum to give the final product.

Yield: 1.07 g (92.1%) of an off-white solid.

$^1$H-NMR (DMSO-$d_6$): δ=1.89 (m, 2H), 2.84 (m, 1H), 3.39 (m, 2H), 3.63 (tr, 2H), 3.92 (s, 6H), 6.88 (d, 1H), 6.97 (d, 1H), 7.5w (d, 2H), 7.82 (m, 4H), 8.07 (d, 2H), 12.30 (br s, 1H).

Examples 8 and 9

(+)- and (−)-4-(4'-Bromo[1,1'-biphenyl]-4-yl)-2-[2-(1,3-dioxo-1,3-dihydro-2H-isoindol2-yl)ethyl]-4-oxobutanoic acid

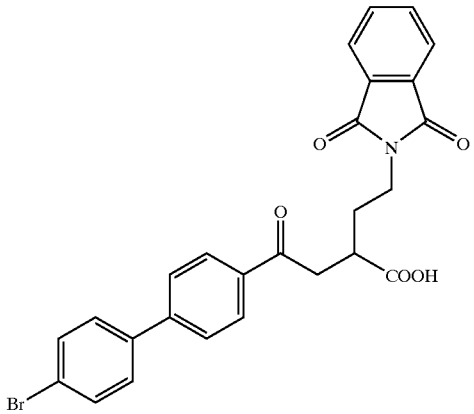

Racemic 4-(4'-Bromo[1,1'-biphenyl]-4-yl)-2-[2-(1,3-dioxo-1,3-dihydro-2H-isoindol-2-yl)-ethyl]-4-oxobutanoic acid was prepared essentially as described in the indicated reference WO 96/15096.

$^1$H-NMR (DMSO-$d_6$): δ=1.95 (m, 2H), 2.88 (m, 1H), 3.38 (m, 2H), 3.72 (tr, 2H), 7.72 (m, 4H), 7.85 (m, 6H), 8.08 (d, 2H), 12.33 (br s, 1H).

1.0 g (1.97 mmol) of this material was separated into pure enantiomers by chiral HPLC using a commercially available 5 μm Kromasil KR 100-5-CHI-DMB phase. A solvent mixture consisting of 40% iso-hexane and 60% of a tert-butylmethyl ether/dichloromethane/glacial acetic acid mixture (480:40:1) was employed at a constant flow rate of 25 ml/min.

Example 8

First eluting enantiomer A:

Yield: 309 mg (31%).

$[α]_D^{20}$=+3.87° (c=0.458 g/100 ml, THF).

Example 9

Second eluting enantiomer B:

Yield: 240 mg (24%).

$[α]_D^{20}$=−5.98° (c=0.482 g/100 ml, THF).

Examples 10 and 11

(+)- and (−)-4-(4'-Chloro[1,1'-bipenyl]-4-yl)-2-[2-(5,7-dioxo-5,7-dihydro-6H-[1,3]-dioxolo[4,5-f]isoindol-6-yl)ethyl]-4-oxobutanoic acid

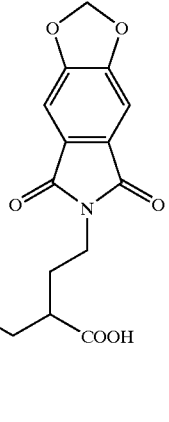

Racemic 4-(4'-Chloro[1,1'-bipenyl]-4-yl)-2-[2-(5,7-dioxo-5,7-dihydro-6H-[1,3]-dioxolo[4,5-f]isoindol-6-yl)ethyl]-4-oxobutanoic acid was prepared essentially as described in the indicated reference WO 96/15096.

$^1$H-NMR (DMSO-$d_6$): δ=1.91 (m, 2H), 2.85 (m, 1H), 3.38 (m, 2H), 3.66 (tr, 2H), 6.26 (s, 2H), 7.39 (s, 2H), 7.58 (d, 2H), 7.82 (m, 4H), 8.06 (d, 2H), 12.31 (br s, 1H).

0.70 g (1.38 mmol) of this material was separated into pure enantiomers by chiral HPLC using a commercially available 1 μm Kromasil KR 100-5-CHI-MDB phase. A solvent mixture consisting of 40% isohexane and 60% of a tert-butylmethyl ether/dichloromethane/glacial acetic acid mixture (480:40:1) was employed at a constant flow rate of 25 ml/min.

Example 10

First eluting enantiomer A:

Yield: 261 mg (37.3%).

$[α]_D^{20}$=+13.99° (c=0.955 ml, THF).

Example 11

Second eluting enantiomer B:

Yield: 228 mg (32.6%).

$[α]_D^{20}$=−15.15° (c=0.991 g/100 ml, THF).

Example 12

4-(4'-Cyano[1,1'-biphenyl]-4-yl)-4-oxo-2-{2-[4-oxo-1,2,3-benzotriazin-3(4H)-yl]ethyl}butanoic acid Intermediate 12A 4'-(2-Bromoacetyl)[1,1'-biphenyl]-4-carbonitrile

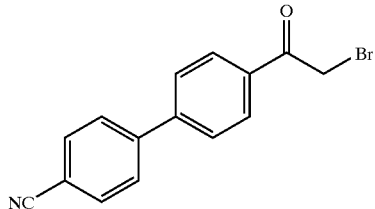

4.68 g aluminium chloride (35.15 mmol) are dissolved in 45 ml dichloromethane and treated dropwise with 3.38 g (16.74 mmol) bromoacetyl bromide at 0° C. After 30 min 3 g (16.74 mmol) 4-cyanobiphenyl, dissolved in 15 ml dichloromethane, are added dropwise. The reaction mixture is stirred overnight at ambient temperature, added to ice-water and extracted 2 times with dichloromethane. The organic phase is washed with water and brine, dried and evaporated. The residue is triturated with petrol ether, filtered and dried. Yield: 4.24 g (83%).

200 MHz $^1$H-NMR (CDCl$_3$): 4.49, s, 2H; 7.73, m, 6H; 8.11, d, 2H.

Intermediate 12B

Di(tert-butyl)-2-[2-(4'-cyano[1,1'-biphenyl]-4-yl)-2-oxoethyl]-2-(2-[4-oxo-1,2,3-benzo-triazin-3(4H)-yl]ethyl)malonate

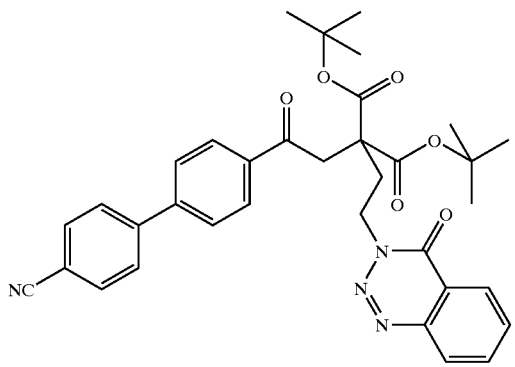

A solution of 2.59 g (6.67 mmol) of Intermediate 13C in 20 ml DMF is added dropwise to a suspension of 0.333 g NaH (60% in mineral oil) in 20 ml DMF. The mixture is stirred for 30 min and a solution of 2 g (6.67 mmol) of Intermediate 12A in 20 ml DMF is added. The mixture is stirred for 2.5 h at RT, poured onto 150 ml NH$_4$Cl solution and extracted with ethyl acetate. The organic phase is washed with water and brine, dried over MgSO$_4$ and evaporated. The residue is purified by chromatography to give 0.62 g (15%).

200 MHz $^1$H-NMR (CDCl$_3$): 2.71, s, 2H; 3.81, s, 2H; 4.53, m, 2H; 7.75, m, 7H; 7.91, m, 1H; 8.10, m, 3H; 8.30, m, 1H.

Example 12

4-(4'-Cyano[1,1'-biphenyl]-4-yl)-4-oxo-2-{2-[4-oxo-1,2,3-benzotriazin-3(4H)-yl]-ethyl}butanoic acid

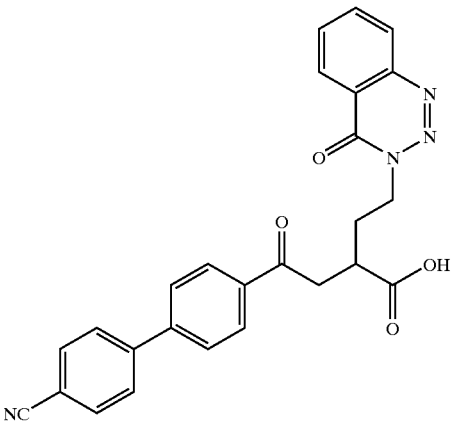

0.61 g (1 mmol) of Intermediate 12B is dissolved in 10 ml dichloro-methane/trifluoroacetic acid (1:1) at 0° C. and the mixture is stirred for 2 h at RT. After adding toluene the reaction mixture is evaporated to dryness and the residue taken into 10 ml dioxane. The solution is stirred under reflux for 6 h and at RT overnight. The solvent is removed in vacuo and the residue purified by HPLC to yield 96 mg (21%).

200 MHz $^1$H-NMR (CDCl$_3$): 2.28, m, 2H; 2.49, m, 2H; 3.26, m, 1H; 4.58, m, 2H, 7.72, m, 10H; 8.18, m, 1H; 8.38, m, 1H.

Example 13

4-Oxo-2-{2-[4-oxo-1,2,3-benzotriazin-3(4H)-yl]ethyl}-4-[4'-(trifluoromethoxy)[1,1'-biphenyl]-4-yl]butanoic acid Intermediate 13A 1-[4-(Trifluoromethoxy)[1,1'-biphenyl]-4-yl-]-1-ethanone

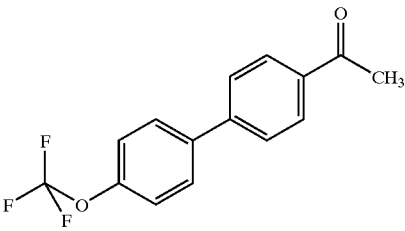

To a mixture of 30 g (126 mmol) 4-(trifluoromethoxy)-1,1'-biphenyl and 21 g aluminium trichloride (157 mmol) in 120 ml nitrobenzene are added at a temperature below 20° C. 9.87 g (126 mmol) acetyl chloride. The reaction mixture is stirred for 2 h at 0° C., added to 240 ml ice-water and 42 ml conc. HCl and extracted with ethyl acetate. The organic phase is washed with water and brine and the solvents removed in vacuo. The residue is triturated with petrol ether, filtrated and dried. From the filtrate another batch can be obtained after crystallizing at 4° C. to give overall 23.5 g (66%).

200 MHz $^1$H-NMR (CDCl$_3$): 2.65, s, 3H; 7.33, d, 2H; 7.58, m, 4H; 8.06, d, 2H.

Intermediate 13B

2-Bromo-1-[4'-(trifluoromethoxy)[1,1'-biphenyl]-4-yl]-1-ethanone

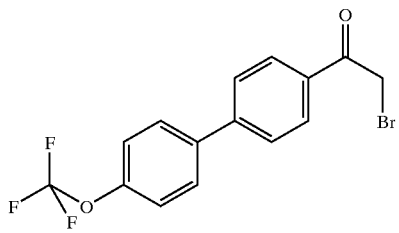

12.27 g (43.8 mmol) of Intermediate 13A are dissolved in a mixture of 150 ml methanol, 150 ml ethanol and 50 ml ether with gentle heating. 5.914 g (56.9 mmol) boronic acid trimethylester are added at RT and 7.35 g (45.9 mmol) bromine are added dropwise. The reaction mixture is stirred until disappearance of the red-brown colour. Solvents are removed in vacuo and the residue is purified by chromatography (cyclohexane/ethyl acetate) to give 6.2 g (39%).

200 MHz $^1$H-NMR (CDCl$_3$): 4.49, s, 2H; 7.33, d, 2H; 7.68, dd, 4H; 8.10, d, 2H.

Intermediate 13C

Di(tert-butyl) 2-{2-[4-oxo-1,2,3-benzotriazin-3(4H)-yl]ethyl}malonate

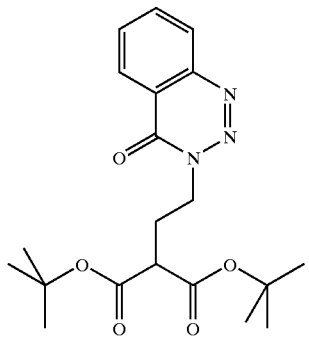

46.2 g (177 mmol) of Intermediate 5E are dissolved in 600 ml THF. 69.8 g (266 mmol) triphenylphosphin und 39.2 g (266 mmol) 1,2,3-benzotriazin-4(3H)-one are added. 46.4 g (266 mmol) DEAD are added dropwise. The reaction mixture was stirred overnight at roomtemperature. The solvent is removed in vacuo and the product obtained by chromatography (cyclohexan/ethylacetate 6:1).

Yield: 51.8 g (63%).

200 MHz $^1$H-NMR (CDCl$_3$): 1.43, s, 18H; 2.43, quar., 2H; 3.30, t, 1H; 4.57, t, 2H; 7.80, m, 1H; 7.94, m, 1H; 8.16, dd, 1H; 8.36, dd, 1H.

Intermediate 13D

Di(tert-butyl)-2-{2-[4-oxo-1,2,3-benzotriazin-3(4H)-yl]ethyl}-2-{2-oxo-2-[4'-(trifluoromethoxy)[1,1'-biphenyl]-4-yl]ethyl}malonate

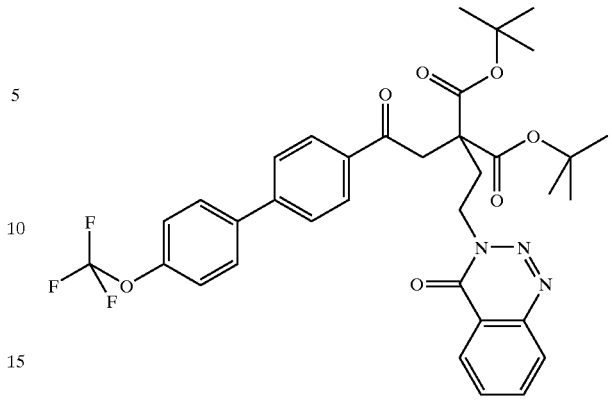

To a suspension of 0.52 g (12.9 mmol) sodium hydride (60% suspension in mineral oil) in 20 ml DMF is added a solution of 4.04 g (10.37 mmol) of Intermediate 13C in 30 ml DMF dropwise. After stirring for 30 min at RT a solution of 3.73 g (10.37 mmol) of Intermediate 13B in 30 ml DMF is added dropwise and the reaction mixture is stirred for 2 h at RT. The reaction mixture is poured onto NH$_4$Cl solution, extracted with ethyl acetate and the organic phase is washed with water and brine. After drying and evaporation of the solvents the product is purified by chromatography to give 2.09 g (30%).

200 MHz $^1$H-NMR (CDCl$_3$): 2.70, m, 2H; 3.82, s, 2H; 4.54, m, 2H; 7.32, d, 2H; 7.62, m, 5H; 8.07, m, 4H; 8.30, m, 1H.

Example 13

4-Oxo-2-{2-[4-oxo-1,2,3-benzotriazin-3(4H)-yl]ethyl}-4-[4'-(trifluoromethoxy)[1,1'-biphenyl]-4-yl]butanoic acid

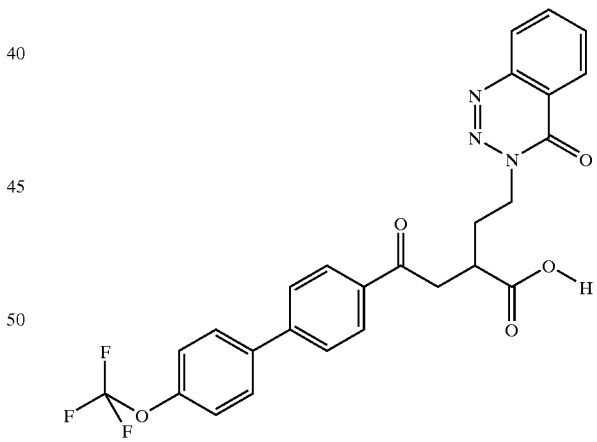

A solution of 2.09 g (3.13 mmol) of Intermediate 13C in 15 ml dichloromethane and 15 ml trifluoroacetic acid is stirred at RT for 2 h. After adding toluene the solvents are removed in vacuo. The residue is dissolved in 30 ml dioxane, the solution is refluxed for 6 h and stirred at RT overnight. Solvents are removed in vacuo, the residue is triturated with ether, the precipitate is collected by filtration and dried to give 0.51 g (32%).

200 MHz $^1$H-NMR (DMSO-d$_6$): 2.18, m, 2H; 2.98, m, 1H; 3.51, m, 2H; 4.52, m, 2H; 7.52, d, 2H; 7.89, m, 5H; 8.10, m, 3H; 8.24, m, 2H; 12.39, s, 1H.

Examples 14 and 15

(+)- and (−)-(1S*,2S*,5R*)-2-[(4'-Chloro[1,1'-biphenyl]-4-yl)carbonyl]-5-[(1,3-dioxo1,3-dihydro-2H-isoindol-2-yl)methyl]cyclopentanecarboxylic acid

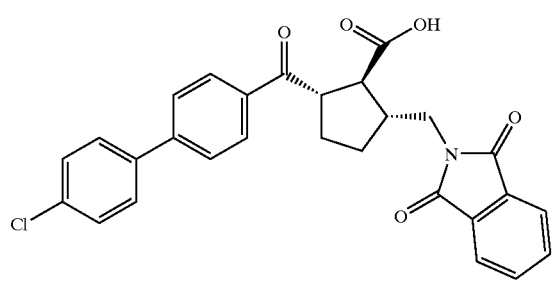

The racemic compound was prepared essentially following the procedure for Example 360 of WO 96/15096.

4.20 g (8.61 mmol) of this material was separated into pure enantiomers by chiral HPLC using a commercially available 5 μm Kromasil KR 100-5-CHI-MDB phase A solvent mixture consisting of 30% iso-hexane and 70% of a tert-butylmethyl ether/dichloromethane/glacial acetic acid mixture (480:40:1) was employed at a constant flow rate of 25 ml/min.

Example 14

First eluting enantiomer A:

Yield: 1.72 g (41.0%).

$[\alpha]_D^{21}$=+44.26° (c=0.464 g/100 ml, THF).

Example 15

Second eluting enantiomer B:

Yield: 1.59 g (37.9%).

$[\alpha]_D^{21}$=−43.70° (c=0.575 g/100 ml, THF).

We claim:
1. Compounds of the general formula (I')

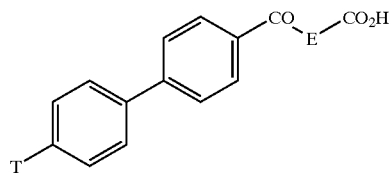

(I')

wherein CO—E—CO$_2$H represents a 3-carboxyl-5-R$^7$-pentan-1-on-1-yl-residue and the substituents T and R$^7$ have the meaning indicated in the following table:

| T | R$^7$ | racemate, (+)- or (−)-enantiomer | |
|---|---|---|---|
| OAc | ![phthalimide] | rac | ; |
| OH | ![phthalimide] | rac | ; |
| Cl | ![dimethoxy phthalimide] | rac | ; |
| CN | ![triazinone] | rac | or |
| OCF$_3$ | ![triazinone] | rac | . |

2. A pharmaceutical composition comprising a compound according to claim 1 and a pharmaceutically acceptable carrier.

3. A method of treating acute and chronic inflammatory processes, comprising administering to a mammal an effective amount of a compound according to claim 1.

4. A method of treating a respiratory disease, comprising administering to a mammal an effective amount of a compound having matrix metalloprotease inhibitory activity and the generalized formula:

$$(T)_xA\text{---}B\text{---}D\text{---}E\text{---}CO_2H$$

wherein
(a) (T)$_x$A represents;

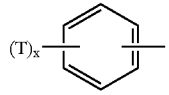

wherein
each T represents a substituent group, independently selected from the group consisting of:
the halogens —F, —Cl, —Br, and —I;
alkyl of 1–10 carbons;

haloalkyl of 1–10 carbons;
haloalkoxy of 1–10 carbons;
alkenyl of 2–10 carbons;
alkynyl of 2–10 carbons;
—(CH$_2$)$_p$Q, wherein
  p is 0 or an integer 1–4,
-alkenyl-Q, wherein
  said alkenyl moiety comprises 2–4 carbons, and
-alkynyl-Q, wherein
  said alkynyl moiety comprises 2–7 carbons; and
  Q is selected from the group consisting of aryl of
    6–10 carbons, heteroaryl comprising 4–9 carbons
    and at least one N, O, or S heteroatom, —CN,
    —CHO, —NO$_2$, —CO$_2$R$^2$, —OCOR$^2$, —SOR$^3$,
    —SO$_2$R$^3$, —CON(R$^4$)$_2$, —SO$_2$N(R$^4$)$_2$, —C(O)
    R$^2$, —N(R$^4$)$_2$, —N(R$^2$)COR$^2$, —N(R$^2$)CO$_2$R$^3$,
    —N(R$^2$)CON(R$^4$)$_2$, —CHN$_4$, —OR$^4$, and —SR$^4$;
  wherein
    R$^2$ represents H;
      alkyl of 1–6 carbons;
      aryl of 6–10 carbons;
      heteroaryl comprising 4–9 carbons and at least
        one N, O, or S heteroatom; or
      arylalkyl in which the aryl portion contains
        6–10 carbons and the alkyl portion contains
        1–4 carbons; or
      heteroaryl-alkyl in which the heteroaryl portion comprises 4–9 carbons and at least one N,
        O, or S heteroatom and the alkyl portion contains 1–4 carbons;
    R$^3$ represents alkyl of 1–4 carbons;
      aryl of 6–10 carbons;
      heteroaryl comprising 4–9 carbons and at least
        one N, O, or S heteroatom; or
      arylalkyl in which the aryl portion contains
        6–10 carbons and the alkyl portion contains
        1–4 carbons; or
      heteroaryl-alkyl in which the heteroaryl portion comprises 4–9 carbons and at least one N,
        O, or S heteroatom and the alkyl portion contains 1–4 carbons;
    R$^4$ represents H;
      alkyl of 1–12 carbons;
      aryl of 6–10 carbons;
      heteroaryl comprising 4–9 carbons and at least
        one N, O, or S heteroatom;
      arylalkyl in which the aryl portion contains
        6–10 carbons and the alkyl portion contains
        1–4 carbons;
      heteroaryl-alkyl in which the heteroaryl portion comprises 4–9 carbons and at least one N,
        O, or S heteroatom and the alkyl portion contains 1–4 carbons;
      alkenyl of 2–12 carbons;
      alkynyl of 2–12 carbons;
      —(C$_q$H$_{2q}$O)$_r$R$^5$ wherein q is 1–3; r is 1–3; and
        R$^5$ is H provided q is greater than 1, or alkyl of
        1–4 carbons, or phenyl;
      alkylenethio terminated with H, alkyl of 1–4
        Carbons, or phenyl;
      alkyleneamino terminated with H, alkyl of 1–4
        carbons, or phenyl;
      —(CH$_2$)$_s$X wherein s is 1–3 and X is halogen;
      —C(O)OR$^2$; or
      —C(O)R$^2$;
    and with the provisos that a) when two R$^4$ groups
      are situated on a nitrogen, they may be joined by a bond to form a heterocycle, and b) unsaturation in a moiety which is attached to Q or
      which is part of Q is separated from any N, O,
      or S of Q by at least one carbon atom, and
    x is 0, 1, or 2;
(b) B represents an optionally substituted p-phenylene ring
    containing 0–2 substituents T, which substituents T may
    independently have the meaning specified under (a);
(c) D represents

(d) E represents a chain of n carbon atoms bearing m
    substituents R$^6$, wherein said R$^6$ groups are independent
    substituents, or constitute spiro or nonspiro rings in which
    a) two groups R$^6$ are joined, and taken together with the
    chain atom(s) to which said two R$^6$ group(s) are attached,
    and any intervening chain atoms, constitute a 3–7 membered ring, or b) one group R$^6$ is joined to the chain on
    which said one group R$^6$ resides, and taken together with
    the chain atom(s) to which said R$^6$ group is attached, and
    any intervening chain atoms, constitutes a 3–7 membered
    ring; and wherein
  n is 2 or 3;
  m is an integer of 1–3;
  each group R$^6$ is independently selected from the group
    consisting of;
    fluorine;
    hydroxyl, with the proviso that a single carbon may
      bear no more than one hydroxyl substituent
    alkyl of 1–10 carbons;
    aryl of 6–10 carbons;
    heteroaryl comprising 4–9 carbons and at least one N,
      O, or S heteroatom;
    arylalkyl wherein the aryl portion contains 6–10 carbons and the alkyl portion contains 1–8 carbons;
    heteroaryl-alkyl wherein the heteroaryl portion comprises 4–9 carbons and at least one N, O, or S
      heteroatom, and the alkyl portion contains 1–8 carbons;
    alkenyl of 2–10 carbons;
    aryl-alkenyl wherein the aryl portion contains 6–10
      carbons and the alkenyl portion contains 2–5 carbons;
    heteroaryl-alkenyl wherein the heteroaryl portion comprises 4–9 carbons and at least one N, O, or S
      heteroatom and the alkenyl portion contains 2–5
      carbons;
    alkynyl of 2–10 carbons;
    aryl-alkynyl wherein the aryl portion contains 6–10
      carbons and the alkynyl portion contains 2–5 carbons;
    heteroaryl-alkynyl wherein the heteroaryl portion comprises 4–9 carbons and at least one N, O, or S
      heteroatom and the alkynyl portion contains 2–5
      carbons;
    —(CH$_2$)$_t$R$^7$ wherein
      t is 0 or an integer of 1–5; and R[7] is selected from the group consisting of

[structures shown]

and corresponding heteroaryl moieties in which the aryl portion of an aryl-containing R[7] group comprises 4–9 carbons and at least one N, O, or S heteroatom;
wherein
  Y represents O or S;
  R[1], R[2], and R[3] are as defined above; and
  u is 0, 1, or 2; and
—(CH$_2$)$_v$ZR[8] wherein
  v is 0 or an integer of 1 to 4; and
  Z represents

[structures shown]

R[8] is selected from the group consisting of:
  alkyl of 1 to 12 carbons;
  aryl of 6 to 10 carbons;
  heteroaryl comprising 4–9 carbons and at least one N, O, or S heteroatom;
  arylalkyl wherein the aryl portion contains 6 to 12 carbons and the alkyl portion contains 1 to 4 carbons;
  heteroaryl-alkyl wherein the aryl portion comprises 4–9 carbons and at least one N, O, or S heteroatom and the alkyl portion contains 1–4 carbons;
  —C(O)R[9] wherein R[9] represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons;

and with the provisos that
when $R^8$ is —C(O)$R^9$, Z is S or O;
when Z is O, $R^8$ may also be —(C$_q$H$_{2q}$O)$_r$R$^5$ wherein q, r, and $R^5$ are as defined above; and
—(CH$_2$)$_w$SiR$^{10}$$_3$ wherein
w is an integer of 1 to 3; and
$R^{10}$ represents alkyl of 1 to 2 carbons;
and with the proviso that
aryl or heteroaryl portions of any of said T or $R^6$ groups optionally may bear up to two substituents selected from the group consisting of —(CH$_2$)$_y$C(R$^4$)(R$^3$)OH, —(CH$_2$)$_y$OR$^4$, —(CH$_2$)$_y$SR$^4$, —(CH$_2$)$_y$S(O)R$^4$, —(CH$_2$)$_y$S(O)$_2$R$^4$, —(CH$_2$)$_y$SO$_2$N(R$^4$)$_2$, —(CH$_2$)$_y$N(R$^4$)$_2$, —(CH$_2$)$_y$N(R$^4$)COR$^3$, —OC(R$^4$)$_2$O— in which both oxygen atoms are connected to the aryl ring, —(CH$_2$)$_y$COR$^4$, —(CH$_2$)$_y$CON(R$^4$)$_2$, —(CH$_2$)$_y$CO$_2$R$^4$, —(CH$_2$)$_y$OCOR$^4$, -halogen, —CHO, —CF$_3$, —NO$_2$, —CN, and —R$^3$, wherein
y is 0–4; and
$R^3$ and $R^4$ are defined as above; and any two $R^4$ which are attached to one nitrogen may be joined to form a heterocycle;
or a an pharmaceutically acceptable salt thereof.

5. The method of claim 1, wherein
(a) (T)$_x$A represents:

wherein
each T represents a substituent group, independently selected from the group consisting of:
the halogens —F, —Cl, —Br, and —I;
alkyl of 1–10 carbons;
haloalkyl of 1–10 carbons;
alkenyl of 2–10 carbons;
alkynyl of 2–10 carbons;
—(CH$_2$)$_p$Q, wherein
p is 0 or an integer 1–4,
-alkenyl-Q, wherein
said alkenyl moiety comprises 2–4 carbons, and
-alkynyl-Q, wherein
said alkynyl moiety comprises 2–7 carbons; and
Q is selected from the group consisting of —OR$^4$ and —SR$^4$;
wherein
$R^4$ represents H;
alkyl of 1–12 carbons;
aryl of 6–10 carbons;
heteroaryl comprising 4–9 carbons and at least one N, O, or S heteroatom;
arylalkyl in which the aryl portion contains 6–10 carbons and the alkyl portion contains 1–4 carbons;
heteroaryl-alkyl in which the heteroaryl portion comprises 4–9 carbons and at least one N, O, or S heteroatom and the alkyl portion contains 1–4 carbons;
—C(O)OR$^2$; or
—C(O)R$^2$;
and with the proviso that unsaturation in a moiety which is attached to Q or which is part of Q is separated from any N, O, or S of Q by at least one carbon atom, and
x is 0, 1, or 2;

(b) B represents an optionally substituted phenyl ring containing 0–2 substituents T, which substituents T may independently have the meaning specified under (a);

(c) D represents $$\diagdown_{C=O}^{\diagup}$$

(d) E represents a chain of n carbon atoms bearing m substituents $R^6$, wherein said $R^6$ groups are independent substituents, or constitute nonspiro rings in which two groups $R^6$ are joined, and taken together with the chain atom(s) to which said two $R^6$ group(s) are attached, and any intervening chain atoms, constitute a 5 or 6-membered ring; and wherein
n is 2 or 3;
m is an integer of 1 or 2;
each group $R^6$ is independently selected from the group consisting of:
arylalkyl wherein the aryl portion contains 6–10 carbons and the alkyl portion contains 1–8 carbons;
—(CH$_2$)$_t$R$^7$ wherein
t is 0 or an integer of 1–5; and
$R^7$ is selected from the group consisting of , wherein $R^2$ is independently selected from the group consisting of: H; aryl of 6–10 carbons
—(CH$_2$)$_v$ZR$^8$ wherein
v is 0 or an integer of 1 to 4; and
Z represents

—S—, , , —O—,

95

-continued

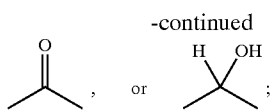

R$^8$ is selected from the group consisting of:
  alkyl of 1 to 12 carbons;
  aryl of 6 to 10 carbons;
  heteroaryl comprising 4–9 carbons and at least one N, O, or S heteroatom;
  arylalkyl wherein the aryl portion contains 6 to 12 carbons and the alkyl portion contains 1 to 4 carbons;
  heteroaryl-alkyl wherein the aryl portion comprises 4–9 carbons and at least one N, O, or S heteroatom and the alkyl portion contains 1–4 carbons;
  —C(O)R$^9$ wherein R$^9$ represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons;

96 and with the provisos that
  when R$^8$ is —C(O)R$^9$, Z is S or O;
  when Z is O, R$^8$ may also be —(C$_q$H$_{2q}$O)$_r$R$^5$ wherein q, r, and R$^5$ are as defined above; and
  —(CH$_2$)$_w$SiR$^{10}$$_3$ wherein
  w is an integer of 1 to 3; and
  R$^{10}$ represents alkyl of 1 to 2 carbons;
and with the proviso that
  aryl or heteroaryl portions of any of said T or R$^6$ groups optionally may bear up to two substituents selected from the group consisting of OR$^4$, N(R$^4$)$_2$, —OC(R$^4$)$_2$O— in which both oxygen atoms are connected to the aryl ring, CON(R$^4$)$_2$, OCOR$^4$, -halogen, —NO$_2$, and alkyl with up to 6 carbon atome
wherein
  R$^4$ is defined as above;
or a pharmaceutically acceptable salt thereof.

6. The method of claim 4 or 5, wherein at least one of the units T and R$^6$ comprises a heteroaromatic ring.

7. The method of claim 4 or 5, wherein in said E unit, n is 2 and m is 1.

8. The method of claim 4 or 5, wherein the compound is selected from the following group:

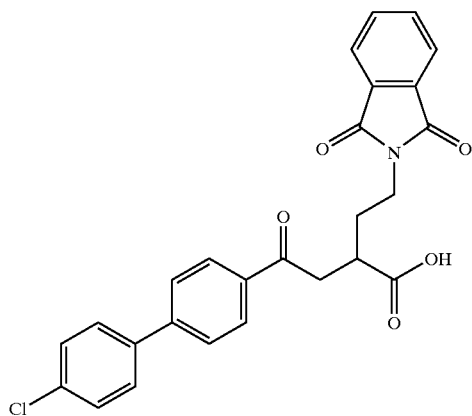

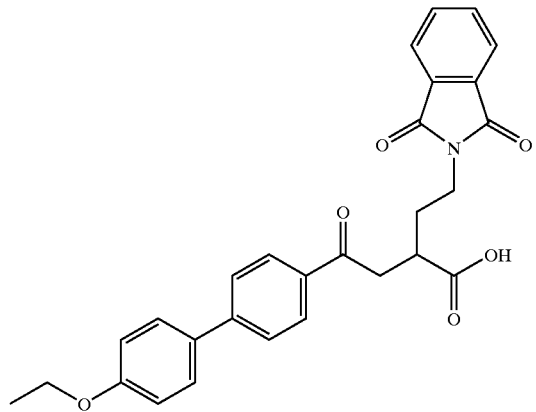

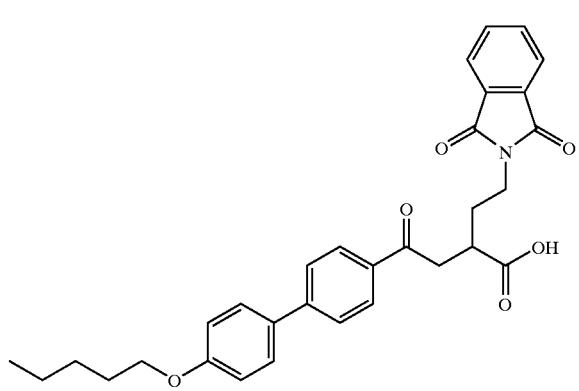

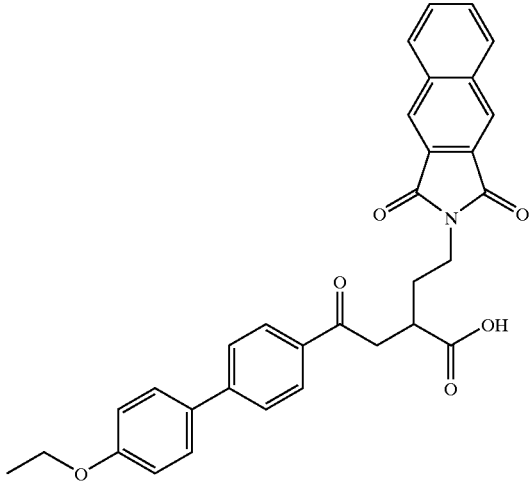

97 98
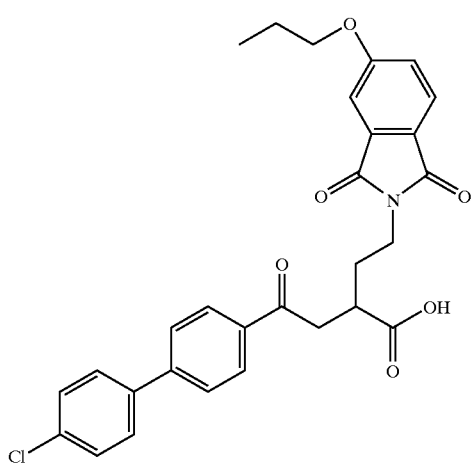
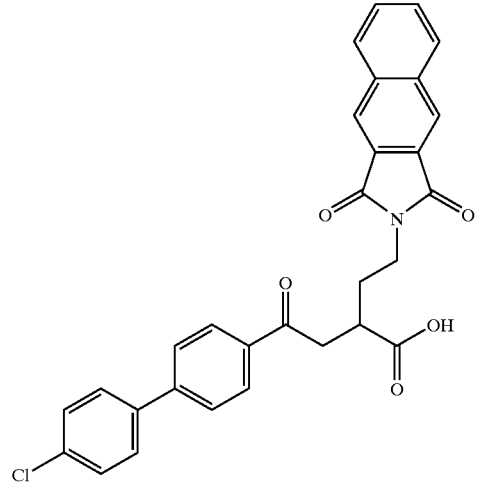
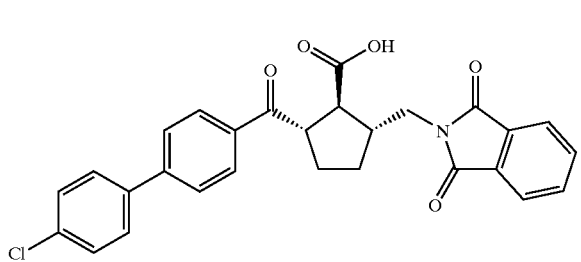
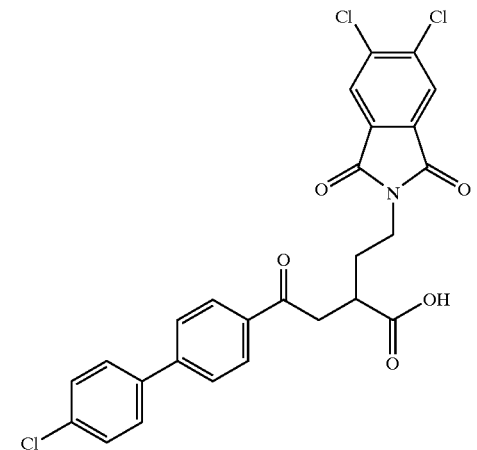
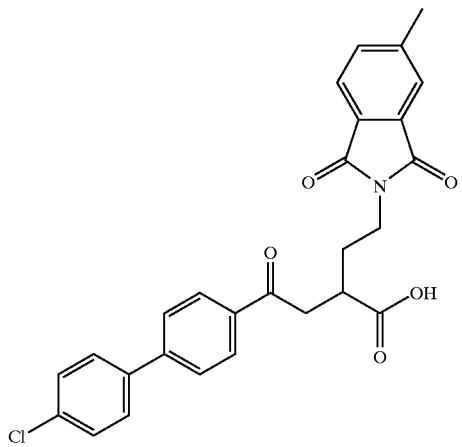
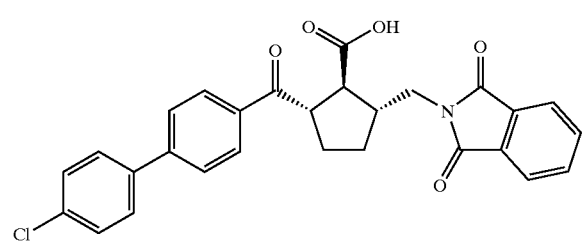
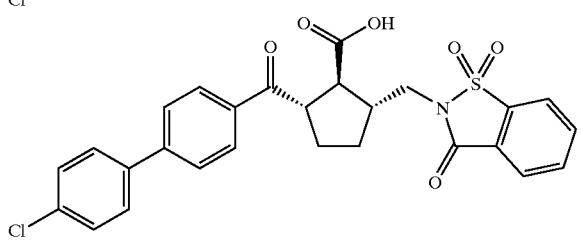
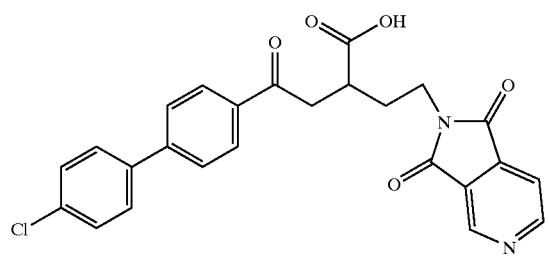

99
-continued
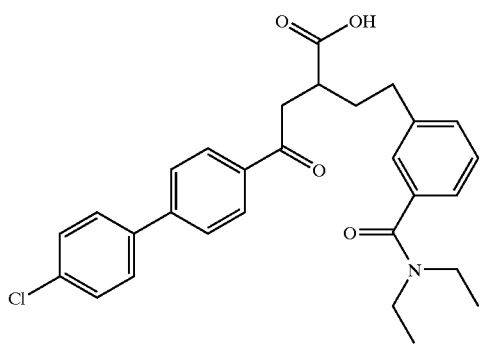
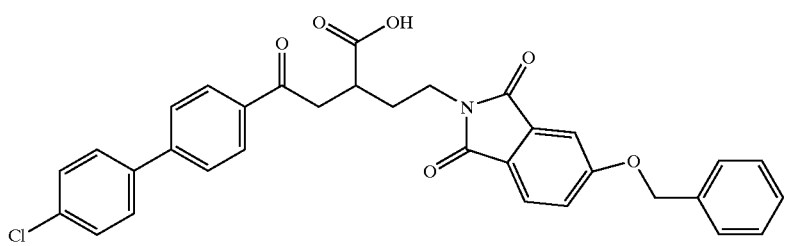
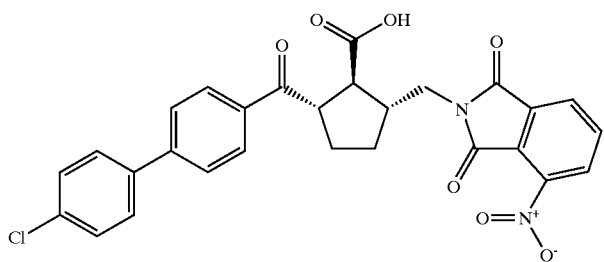
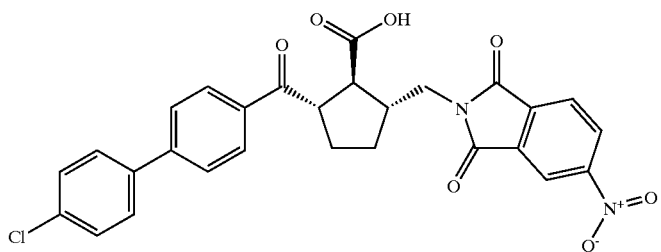
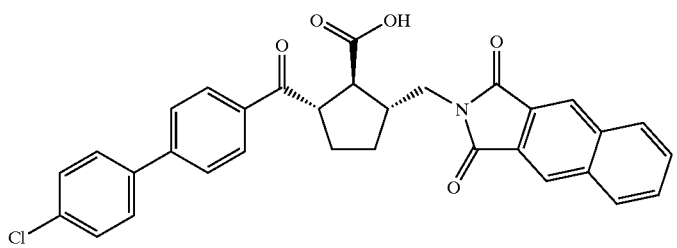
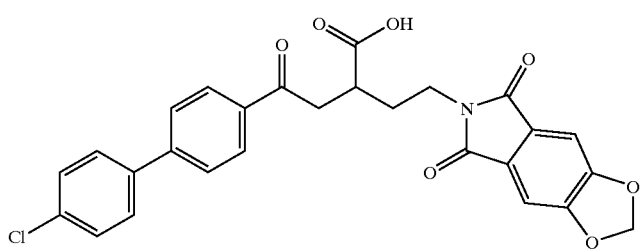
100
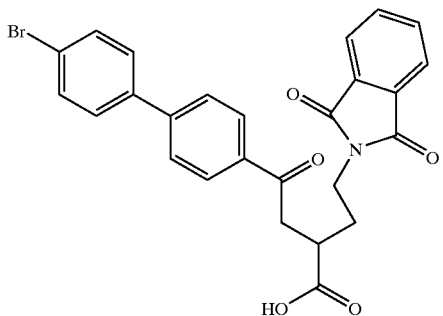

-continued
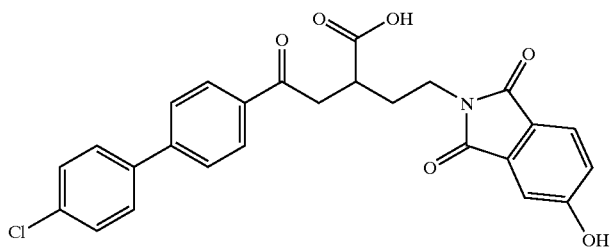
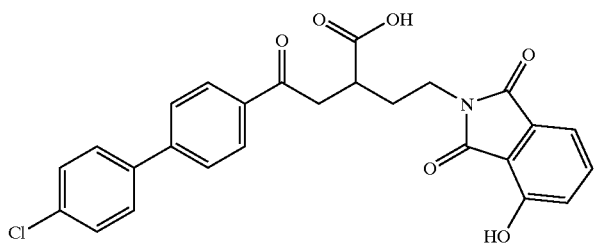
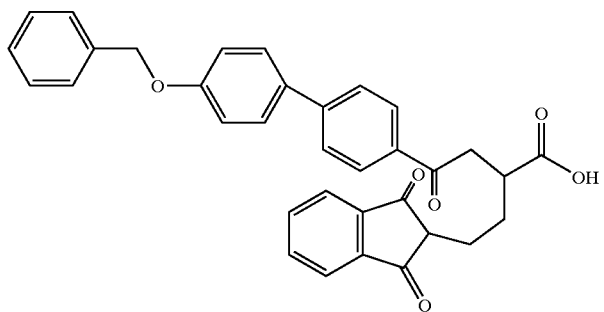
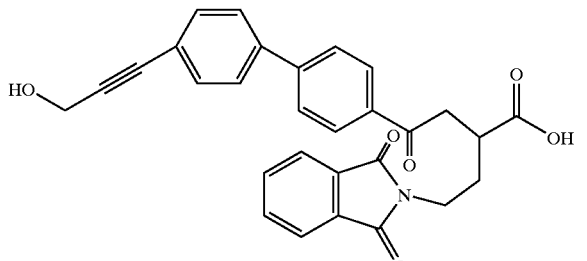
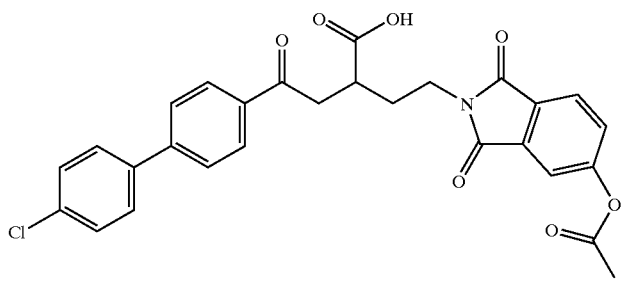
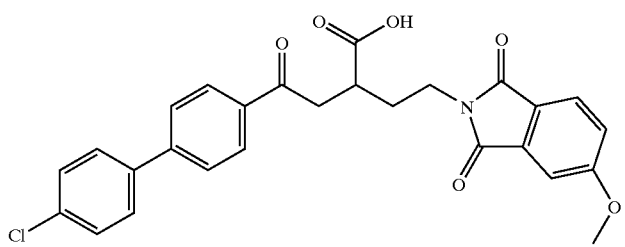

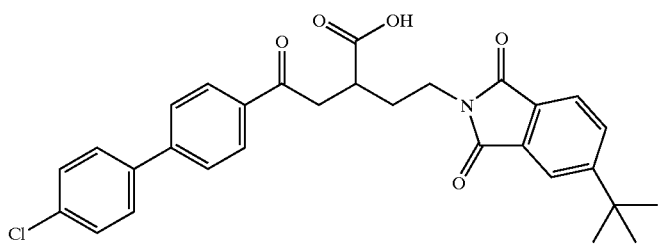
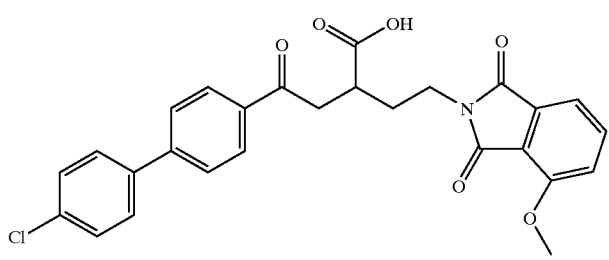
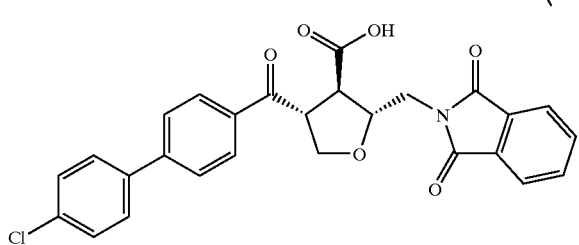
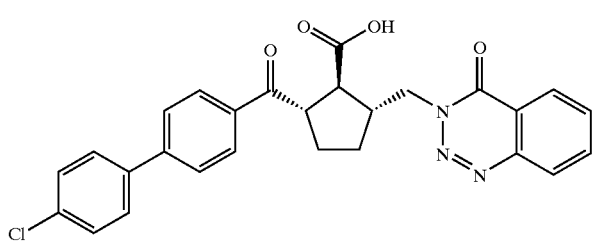
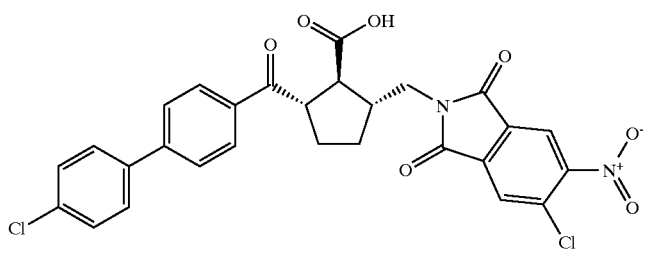
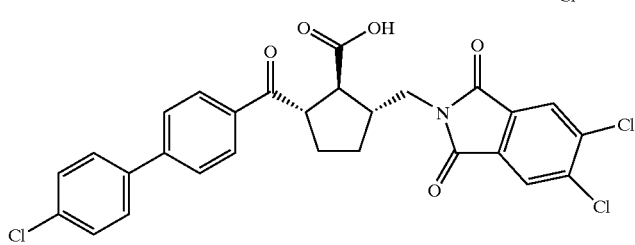
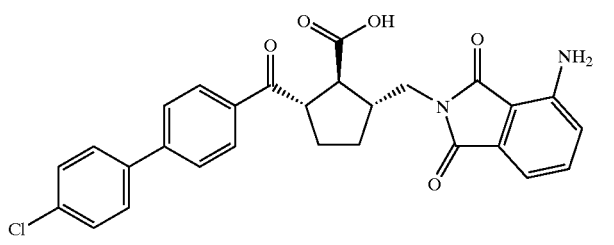

105
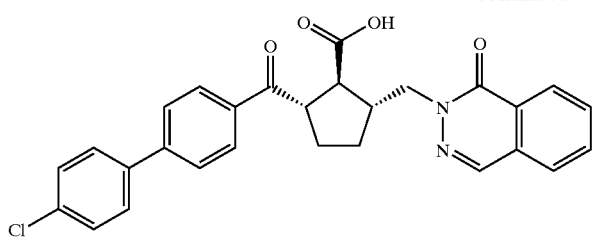
106
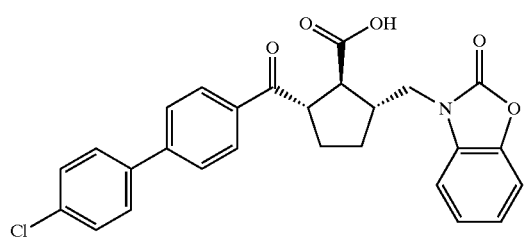
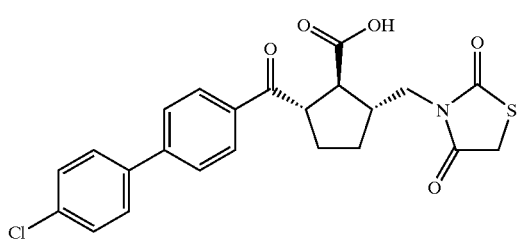
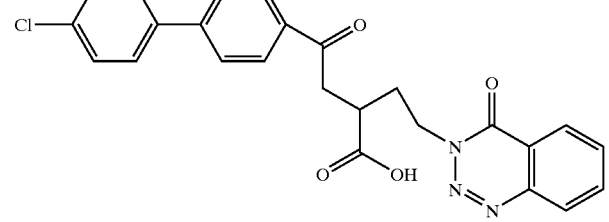
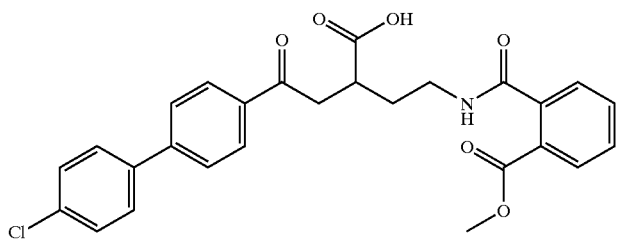
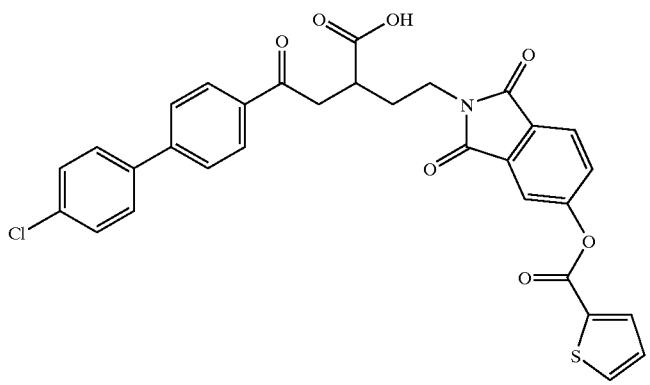
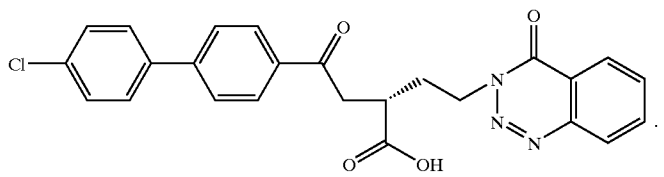

9. A method of treating a respiratory disease, comprising administering to a mammal an effective amount of a compound of the general formula (I')

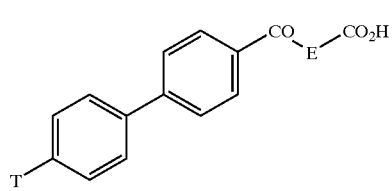

wherein

T is $(C_1-C_4)$-alkoxy, chloride, bromide, fluoride, acetoxy, hydroxy, cyano, trifluoromethyl or trifluoromethoxy, CO—E—$CO_2$H represents a 3-carboxyl-5-$R^7$-pentan-1-on-1-yl- or a 2-carboxyl-3-($R^7$-methyl)-cyclopentan-1-yl)carbonyl-residue, and $R^7$ represents a group of the formula

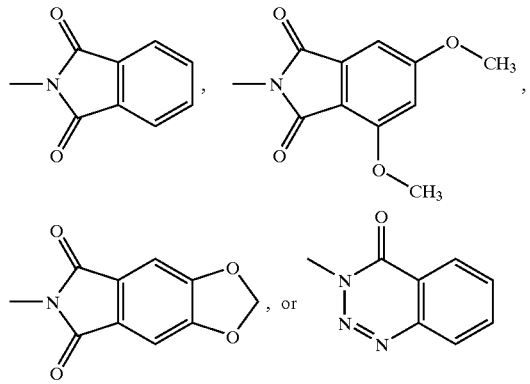

or its salt.

10. A method of treating a respiratory disease, comprising administering to a mammal an effective amount of the compound (+)-2-[2-(1,3-dioxo-1,3-dihydro-2H-isoindol-2-yl)ethyl]4-(4'-ethoxy[1,1'-biphenyl]-4-yl)-4-oxobutanoic acid,

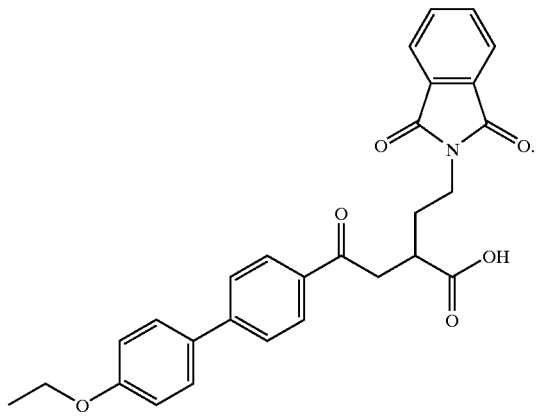

11. A method of treating a respiratory disease, comprising administering to a mammal an effective amount of the compound (+)-4-(4'-chloro[1,1'-biphenyl]-4-yl)-2-[2-(1,3-dioxo-1,3-dihydro-2H-isoindol-2-yl)ethyl]-4-oxobutanoic acid

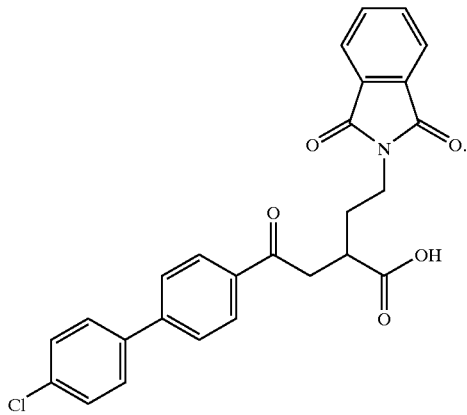

12. The method of claim 4, 9, 10 or 11, wherein said respiratory disease is selected from the group consisting of asthma; chronic obstructive pulmonary diseases including chronic bronchitis and emphysema; cystic fibrosis; bronchiectasis; adult respiratory distress syndrome (ARDS); allergic respiratory disease including allergic rhinitis; diseases linked to $TNF_\alpha$ production including acute pulmonary fibrotic diseases, pulmonary sarcoidosis, silicosis, coal worker's pneumoconiosis, alveolar injury in mammals, such as human, a farm animal or a domestic pet.

* * * * *